United States Patent [19]

Morishita et al.

[11] Patent Number: 5,160,487
[45] Date of Patent: Nov. 3, 1992

[54] ELECTROPHOTOGRAPHIC MEMBER

[75] Inventors: Yoshii Morishita; Yasushi Sugimoto; Shigeru Hayashida, all of Hitachi; Hiroko Ishikawa, Katsuta; Yoshiaki Noda, Ichikawa; Shigeru Murakami, Tokyo; Munehiro Sato; Yoshinori Saito, both of Ichikawa; Naoji Kurata, Nishinomiya; Yoshio Sugita, Chiba, all of Japan

[73] Assignee: Hitachi Chemical Company, Ltd., Tokyo, Japan

[21] Appl. No.: 754,657

[22] Filed: Sep. 4, 1991

[30] Foreign Application Priority Data

Sep. 4, 1990 [JP] Japan ..................... 2-233899
Sep. 4, 1990 [JP] Japan ..................... 2-234031
Sep. 4, 1990 [JP] Japan ..................... 2-234032

[51] Int. Cl.$^5$ .................. G03G 5/06; G03G 5/047
[52] U.S. Cl. ........................... 430/59; 430/76; 430/77; 430/96
[58] Field of Search ............... 430/59, 58, 73, 76, 430/96

[56] References Cited

U.S. PATENT DOCUMENTS 3,935,230 1/1976 Yale ........................ 260/268 R
4,933,245 6/1990 Akasaki et al. ................ 430/59

Primary Examiner—John L. Goodrow
Attorney, Agent, or Firm—Antonelli, Terry, Stout & Kraus

[57] ABSTRACT

Disclosed is an electrophotographic member containing as a charge transport material a fluorine-containing N,N,N',N'-tetraarylbenzidine derivative which is remarkably excellent in solubility in an organic solvent and/or a binder such as polycarbonate resin, etc., can show very excellent electrophotographic properties such as high sensitivity, low residual potential and high durability. Further, a fluorine-containing N,N,N',N'-tetraarylbenzidine derivative usable as a charge transport material, and a process for producing the same are disclosed. Furthermore, a fluorine-containing diarylamine usable for producing the fluorine-containing N,N,N',N'-tetraarylbenzidine derivative, and a process for producing the same are disclosed.

14 Claims, 22 Drawing Sheets

ELECTROPHOTOGRAPHIC MEMBER

BACKGROUND OF THE INVENTION

This invention relates to an electrophotographic member and a fluorine-containing N,N,N',N'-tetraarylbenzidine derivative usable as a charge transport material in the electrophotographic member.

Heretofore, electrophotographic members containing inorganic materials such as Se, CdS, etc. have been used mainly, but recently electrophotographic members using organic materials are noticed from the viewpoints of safety in handling and advantage in price. Electrophotographic members can be divided into a single layer type wherein a charge generation material and a charge transport material are present in a single layer, and a laminated type wherein a charge generation layer and a charge transport layer are laminated.

As charge transport materials, there are known charge transport materials having electron transport ability such as a mixture of polyvinyl carbazol and trinitrofluorenone (1:1 by mole), and charge transport materials having hole transport ability such as hydrazones, enamines, benzidine derivatives (Japanese Patent Examined Publication Nos. 55-42380 and 59-9049, Japanese Patent Unexamined Publication Nos. 62-237458, 55-79450, and 61-295558, U.S. Pat. Nos. 4,265,990; 4,306,008 and 4,588,666).

As the benzidine derivatives, there are known N,N,N',N'-tetraphenylbenzidine, N,N'-diphenyl-N,N'-bis(3-methylphenyl)-benzidine, N,N,N',N'-tetrakis(4-methylphenyl)-benzidine, N,N'-diphenyl-N,N'-bis(4-methoxyphenyl)-benzidine, etc. But, these benzidine derivatives are low in solubility in organic solvents and/or easily oxidized. Since these benzidine derivatives are low in solubility in organic solvents and/or binders, it is difficult to prepare a coating solution for forming a charge transport layer, and crystals of the benzidine derivatives are undesirably deposited at the time of forming the coating film. Further, even if a good charge transport layer can be formed, since resistance to oxidation of the benzidine derivatives are poor, there are defects in that charging characteristics, dark decay, sensitivity and image quality are lowered when used repeatedly.

As binders used in combination with these benzidine derivatives, there are known bisphenol A type polycarbonates (Japanese Patent Examined Publication No. 59-9049), poly(4,4'-cyclohexylidenediphenylenecarbonate) (Japanese Patent Unexamined Publication No. 63-278065), etc. But since these benzidine derivatives are poor in resistance to oxidation, there are defects in that charging characteristics, dark decay, sensitivity and image quality are remarkably lowered when used repeatedly. As charge generation materials used in combination with these benzidine derivatives, there are known chloroindium phthalocyanine (Japanese Patent Unexamined Publication No. 61-84655), vanadyl phthalocyanine (Japanese Patent Unexamined Publication No. 61-295558), but not sufficient in practical use in sensitivity.

SUMMARY OF THE INVENTION

It is an object of the present invention to provide an electrophotographic member high in sensitivity and not deteriorated in charging characteristics, dark decay, sensitivity and image quality even if repeatedly used using as a charge transport material a fluorine-containing N,N,N',N'-tetraarylbenzidine derivative excellent in solubility in organic solvents and excellent in compatibility with binders such as polycarbonate resins, improving the disadvantages mentioned above.

It is another object of the present invention to provide a fluorine-containing N,N,N',N'-tetraarylbenzidine derivative usable as a charge transport material, and a process for producing the same.

It is a further object of the present invention to provide a fluorine-containing diarylamine usable for producing the fluorine-containing N,N,N',N'-tetraarylbenzidine derivative, and a process for producing the same.

The present invention provides an electrophotographic member characterized by using as a charge transport material a fluorine-containing N,N,N',N'-tetraarylbenzidine derivative of the formula:

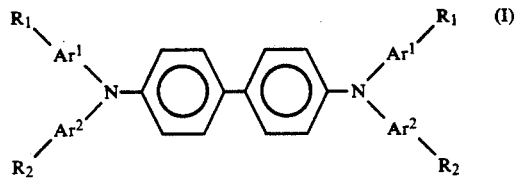

wherein $R_1$ and $R_2$ are independently a hydrogen atom, an alkyl group, an alkoxy group, a fluoroalkyl group or a fluoroalkoxy group, and at least one of $R_1$ and $R_2$ is a fluoroalkyl group or a fluoroalkoxy group; and $Ar^1$ and $Ar^2$ are independently an aryl group which may have one or more substituents other than $R_1$ and $R_2$.

The present invention also provides a fluorine-containing N,N,N',N'-tetraarylbenzidine derivative of the formula:

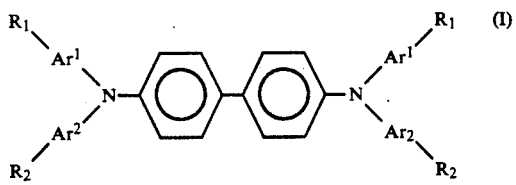

wherein $R_1$ and $R_2$ are independently a hydrogen atom, an alkyl group, an alkoxy group, a fluoroalkyl group or a fluoroalkoxy group, and at least one of $R_1$ and $R_2$ is a fluoroalkyl group or a fluoroalkoxy group; and $Ar^1$ and $Ar^2$ are independently an aryl group which may have one or more substituents other than $R_1$ and $R_2$, and a process for producing the same.

The present invention further provides a diarylamine compound represented by the formula:

wherein $R_1$, $R_2$, $Ar^1$ and $Ar^2$ are as defined above, and a process for producing the same.

DESCRIPTION OF THE PREFERRED EMBODIMENTS

Figure 1:
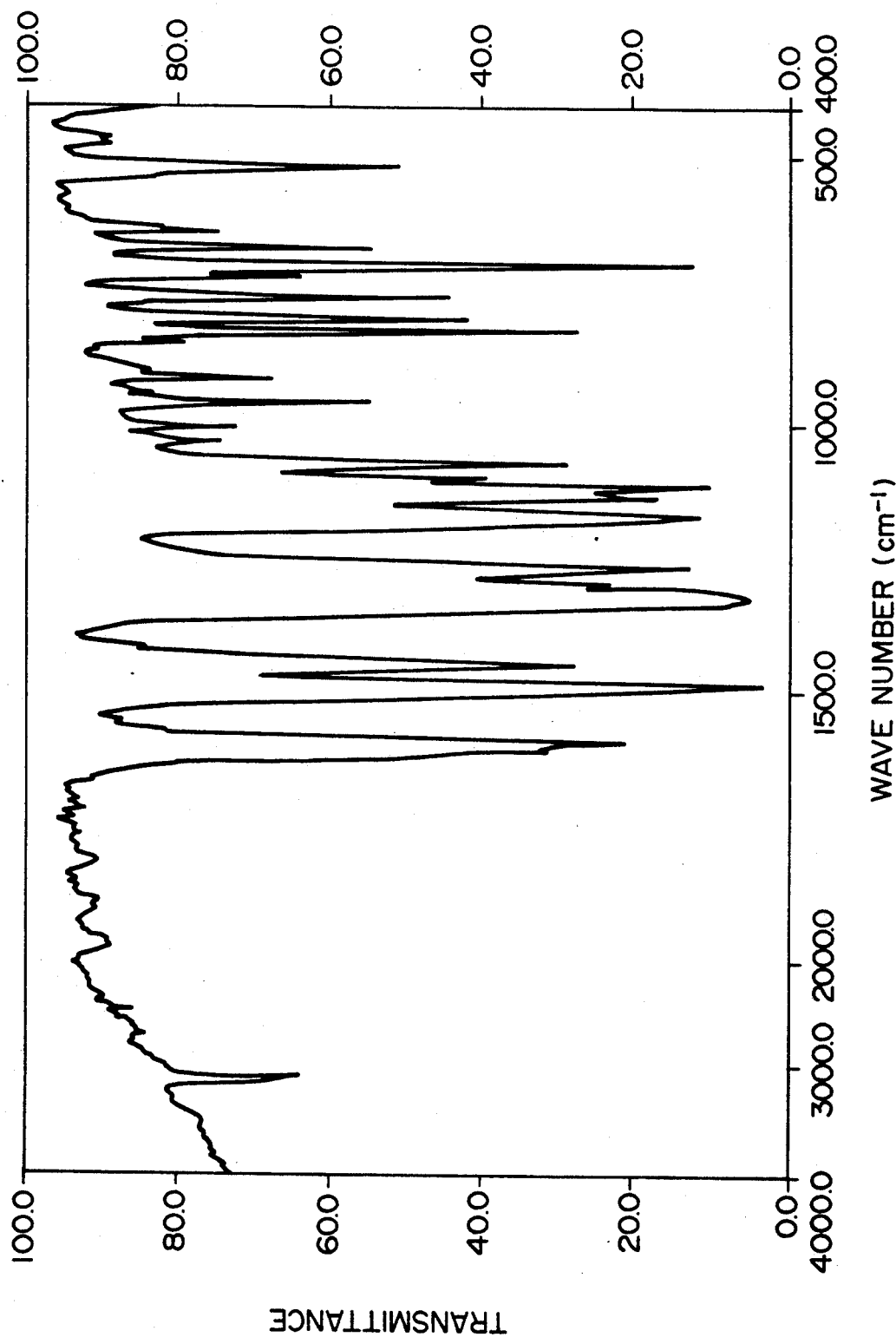
FIGS. 1 to 7 and 12 to 17 are infrared absorption spectra of fluorine-containing N,N,N',N'-tetraarylbenzidine derivatives of the present invention obtained in Synthesis Examples 1 to 7 and 11 to 16.
Figure 2:
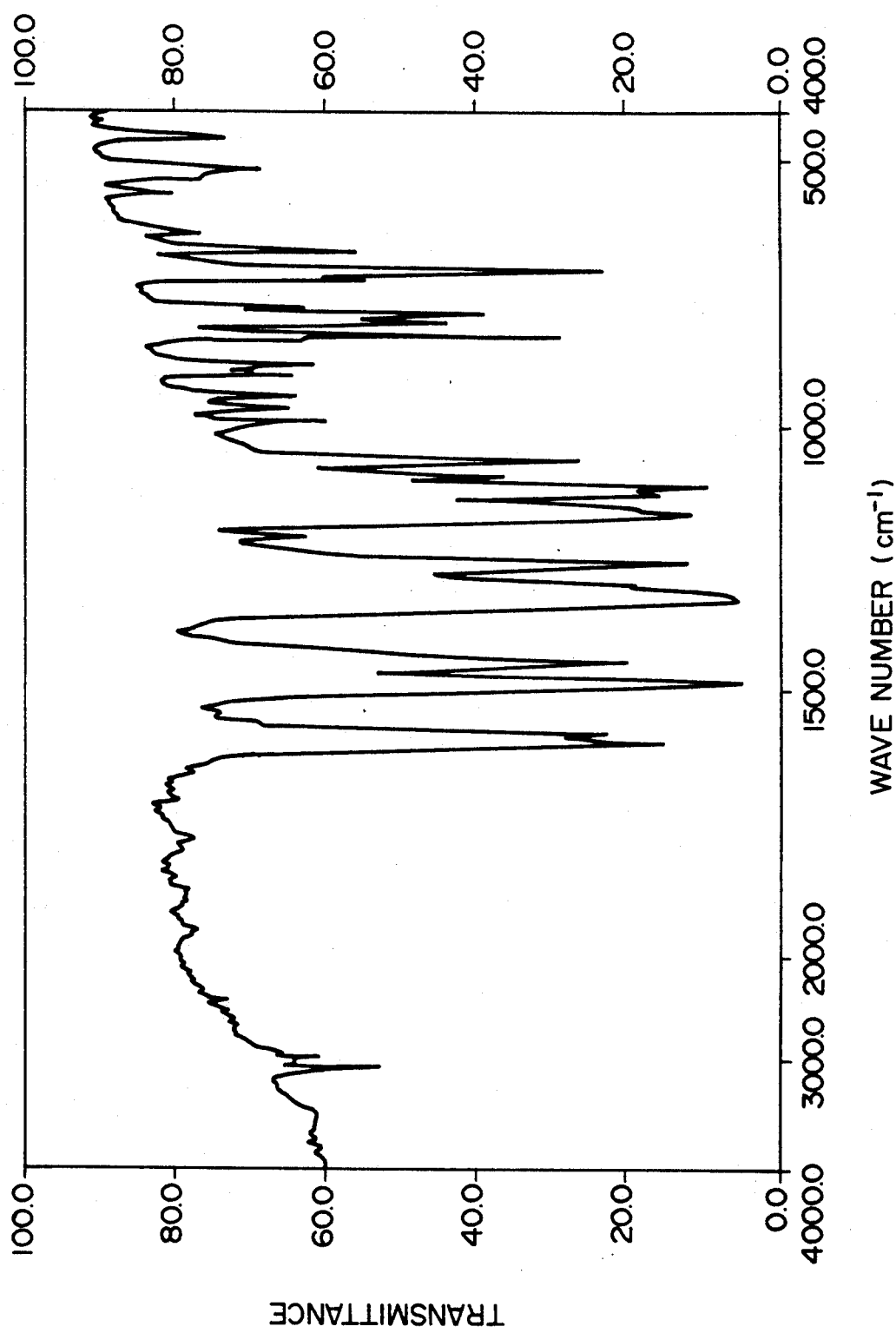
Figure 3:
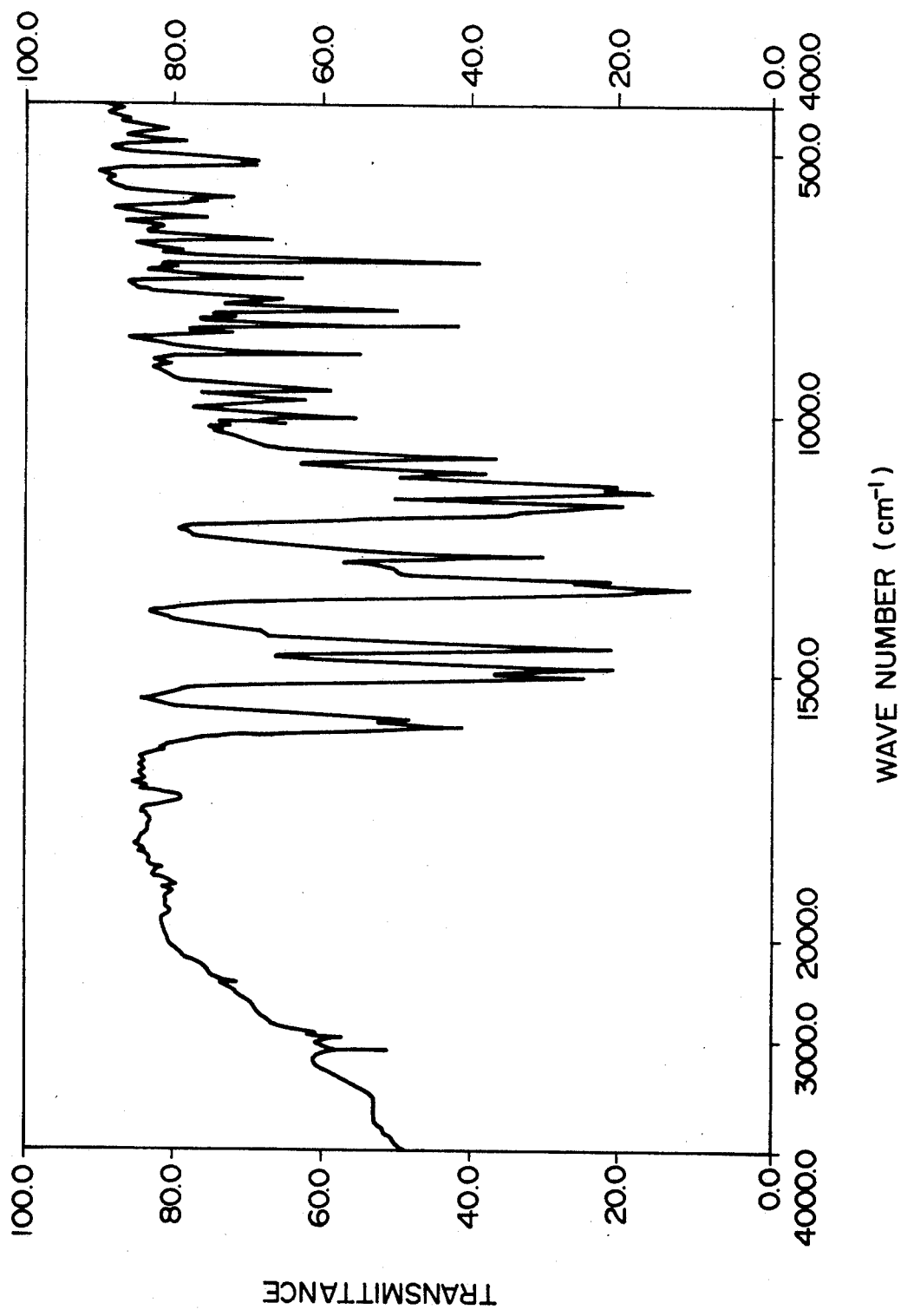
Figure 4:
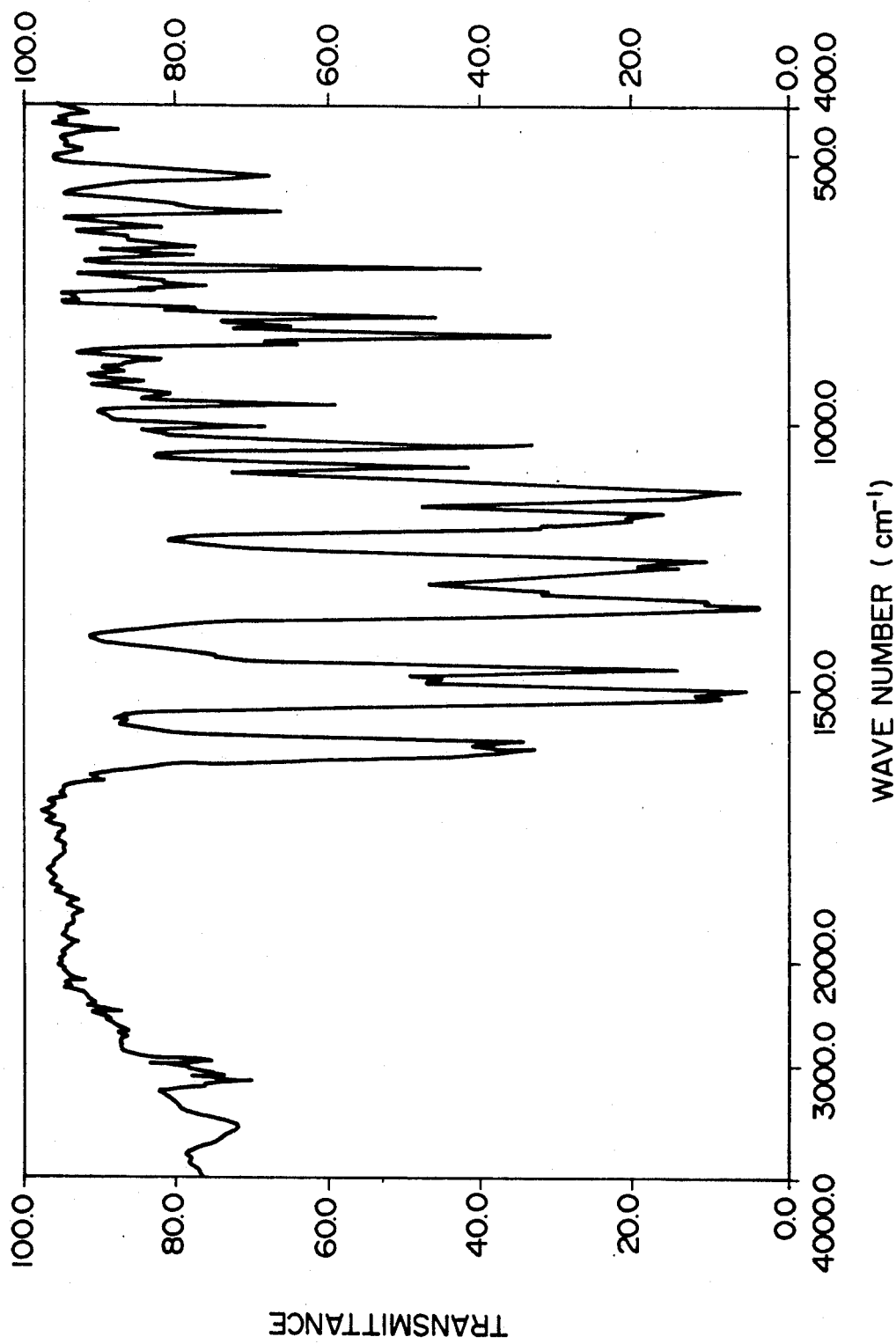
Figure 5:
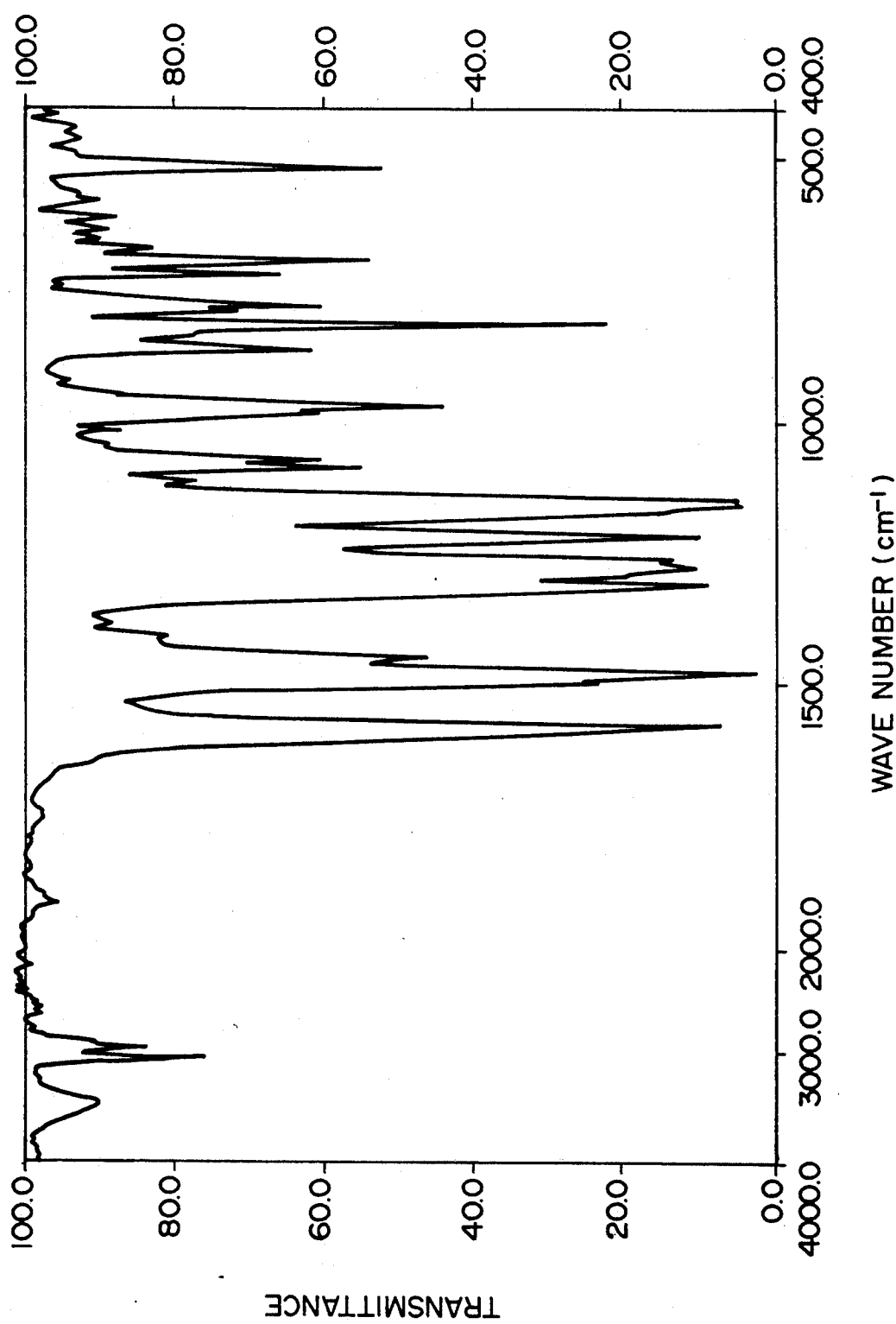
Figure 6:
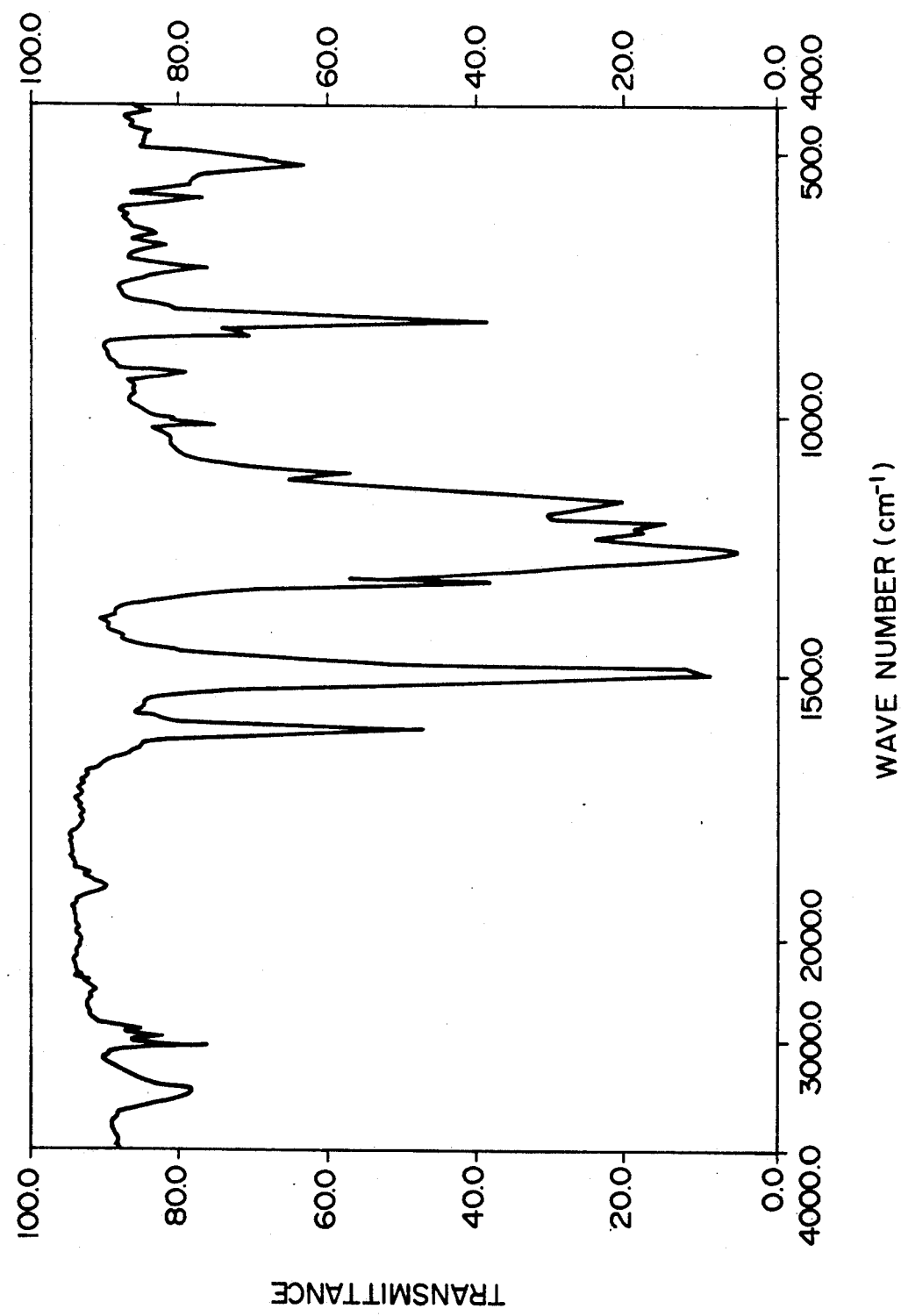
Figure 7:
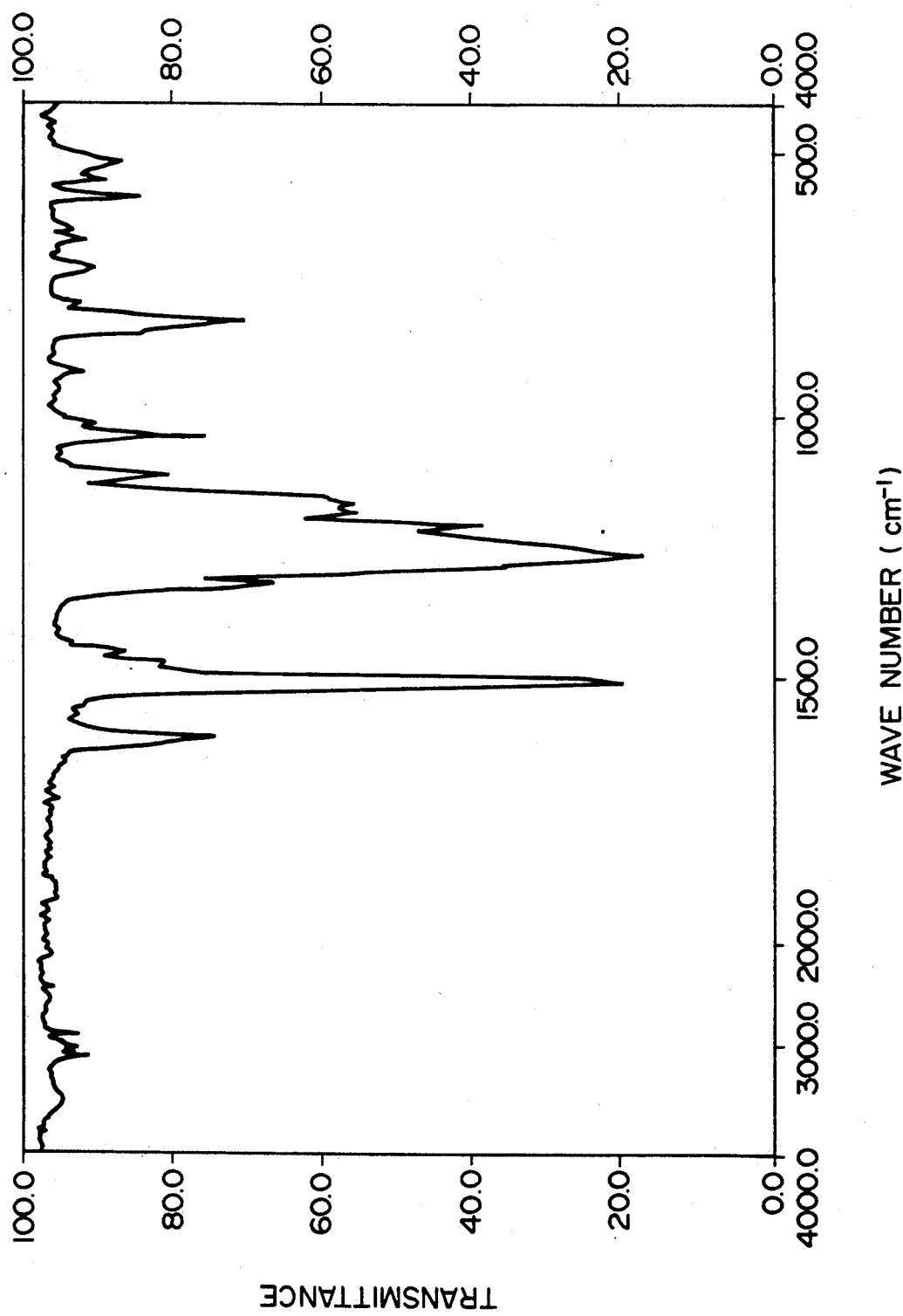

The electrophotographic member of the present invention is characterized by using as a charge transport material a fluorine-containing N,N,N',N'-tetraarylbenzidine derivative of the formula:

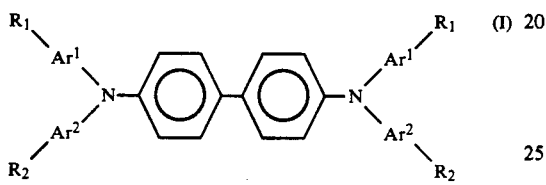

wherein $R_1$ and $R_2$ are independently a hydrogen atom, an alkyl group, an alkoxy group, a fluoroalkyl group or a fluoroalkoxy group, and at least one of $R_1$ and $R_2$ is a fluoroalkyl group or a fluoroalkoxy group; and $Ar^1$ and $Ar^2$ are independently an aryl group which may have one or more substituents other than $R_1$ and $R_2$.

The compound of the formula (I) can be produced by reacting a halogenated biphenyl derivative of the formula:

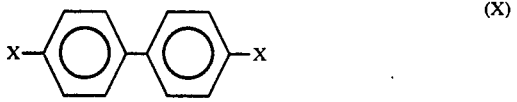

wherein X is iodine or bromine, with a diarylamine compound represented by the formula:

wherein $R_1$, $R_2$, $Ar^1$ and $Ar^2$ are as defined above, in the presence of a copper catalyst (e.g. a copper powder, copper oxide, copper halide, etc.) and a basic compound (e.g. carbonates or hydroxides of alkali metals such as potassium carbonate, sodium carbonate, potassium hydroxide, sodium hydroxide, etc.) in the absence of a solvent or in an organic solvent (e.g. nitrobenzene, dichlorobenzene, quinoline, dimethylsulfoxide, 1,3-dimethyl-2-imidazolidinone, N,N-dimethylformamide, N-methyl-2-pyrrolidone, sulfolane, etc. alone or as a mixture thereof at 120° to 280° C. for 2 to 48 hours with heating and stirring, dissolving the reaction mixture in an organic solvent such as methylene chloride, toluent, or the like, separating insoluble substances, removing the solvent by evaporation, purifying the residue with an alumina column, etc. and recrystallizing from hexane, cyclohexane, or the like to yield the fluorine-containing N,N,N',N'-tetraarylbenzidine derivative of the formula (I).

More concretely, a fluorine-containing N,N,N',N'-tetraarylbenzidine derivative of the formula:

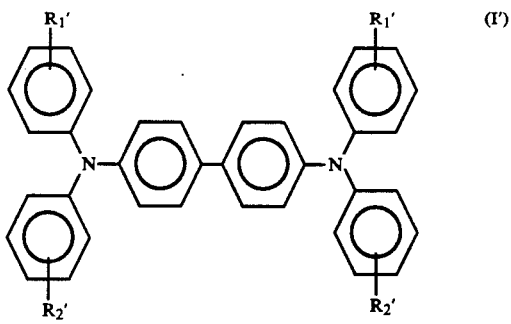

wherein $R_1'$ and $R_2'$ are independently a hydrogen atom, an alkyl group, a fluoroalkyl group, an alkoxy group or a fluoroalkoxy group, each group having 1 to 3 carbon atoms, an aryl group having 6 to 20 carbon atoms, and at least one of $R_1'$ and $R_2'$ is a fluoroalkyl group having 1 to 3 carbon atoms or a fluoroalkoxy group having 1 to 3 carbon atoms, can be produced by reacting a halogenated biphenyl derivative of the formula:

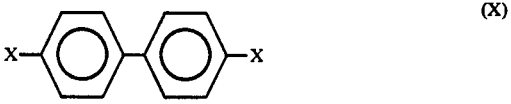

wherein X is as defined above, with a diarylamine compound of the formula:

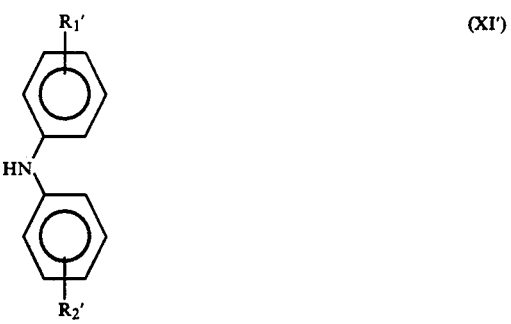

wherein $R_1'$ and $R_2'$ are as defined above, in the presence of a copper catalyst and a basic compound.

Examples of the compound of the formula (X) are 4,4'-diiodobiphenyl, 4,4'-dibromobiphenyl, etc. Among them, the use of 4,4'-diiodobiphenyl is preferable.

Examples of the compound of the formula (XI') are N-trifluoromethylphenylanilines, N-trifluoromethyltoluidines, N-trifluoromethylphenylanisidines, N-trifluoromethylphenylxylidines, N-(trifluoromethylphenyl)phenylanilines, N-trifluoromethoxyanilines, N-trifluoroethoxyanilines, N-trifluoromethoxyphenyltoluidines, N-trifluoroethoxyphenyltoluidines, N-trifluoromethoxyanisidines, N-trifluoroethoxyanisidines, N-trifluoromethoxyphenylxylidines, N-trifluoroethoxyphenylxylidines, N-(trifluoromethoxyphenyl)- phenylanilines, N-(trifluoroethoxyphenyl)phenylanilines, etc.

The diarylamine compound is used in an amount of preferably 0.4 to 20 moles, more preferably 1 to 6 moles, per mole of the halogenated biphenyl derivative.

Example of the copper catalyst are a copper powder, copper oxide and copper halide. Preferable examples of them are a copper powder, copper (I) oxide, copper (II) oxide and copper (I) iodide. The copper catalyst is used in an amount of preferably 0.2 to 10 moles, more preferably 0.5 to 3 moles, per mole of the halogenated biphenyl derivative.

Examples of the basic compound used as a catalyst are hydroxides or carbonates of alkali metals. Preferable examples of them are sodium hydroxide, potassium hydroxide, sodium carbonate and potassium carbonate. Among them, the use of potassium hydroxide or potassium carbonate is preferable. The basic compound is used in an amount of preferably 0.2 to 10 moles, more preferably 0.5 to 3 moles, per mole of the halogenated biphenyl derivative.

Above reaction can be carried out, if necessary, in an organic solvent. Examples of the organic solvent are nitrobenzene, dichlorobenzene, quinoline, N,N-dimethylformamide, dimethylsulfoxide, N-methyl-2-pyrrolidone, 1,3-dimethyl-2-imidazolidinone, sulfolane, etc., alone or as a mixture thereof. The organic solvent is preferably used in an amount of 0.2 to 10 parts by weight, more preferably 0.5 to 5 parts by weight, per part by weight of the halogenated biphenyl derivative.

The reaction of the halogenated biphenyl derivative with the diarylamine compound can be carried out at preferably 120° to 280° C., more preferably 150° to 250° C., for 2 to 48 hours.

The diarylamine compound of the formula (XI) can be produced by reacting a fluorine-containing aniline of the formula:

$$H_2N-Ar^1-R_1 \quad (XII)$$

wherein $Ar^1$ and $R_1$ are as defined above, with acetic anhydride to yield an acetanilide compound, which is then reacted with a halogenated benzene compound of the formula:

$$R_2-Ar^2-X \quad (XIII)$$

wherein $R_2$, $Ar^2$, and X are as defined above, in the presence of a copper catalyst and a basic compound, followed by hydrolysis in an alkaline aqueous solution.

More concretely, a diarylamine compound of the formula:

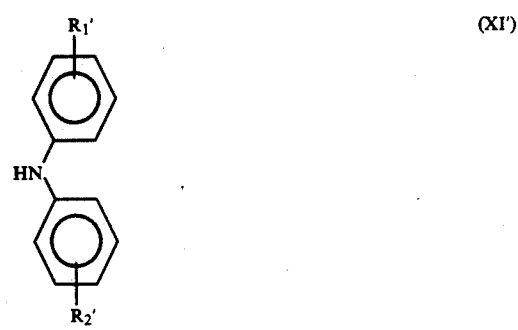

(XI')

wherein $R_1'$ and $R_2'$ are as defined above, can be produced by reacting a fluorinated alkoxy-substituted aniline of the formula:

(XII')

wherein $R_1'$ is a fluoroalkoxy group having 1 to 3 carbon atoms, with acetic anhydride (acetylation reaction) to yield an acetanilide compound, which is then reacted with a halogenated benzene compound of the formula:

(XIII')

wherein $R_2'$ is a hydrogen atom, an alkyl group having 1 to 3 carbon atoms, a fluoroalkyl group having 1 to 3 carbon atoms, an alkoxy group having 1 to 3 carbon atoms, or a fluoroalkoxy group having 1 to 3 carbon atoms, or an aryl group having 6 to 20 carbon atoms; and X is an iodine atom or a bromine atom, in the presence of a copper catalyst and a basic compound (condensation reaction), followed by hydrolysis in an alkaline aqueous solution.

Examples of the fluorinated alkoxy-substituted aniline are trifluoromethoxyanilines such as N-(3-trifluoromethoxy)aniline, N-(4-trifluoromethoxy)aniline, etc.; trifluoroethoxyanilines such as N-3-(2,2,2-trifluoroethoxy)aniline, N-4-(2,2,2-trifluoroethoxy)aniline, etc.

The acetic anhydride is used preferably in an amount of 1 to 2 moles per mole of the fluorinated alkoxy-substituted aniline.

The acetylation reaction can be carried out, if necessary, in an organic solvent such as inert aliphatic hydrocarbons having 6 to 18 carbon atoms; aromatic hydrocarbons such as benzene, toluene, xylene, etc.; aliphatic organic acids having 1 to 12 carbon atoms and esters thereof; organic bases such as pyridine, picoline, etc. The organic solvent can preferably be used in an amount of 0.5 to 5 parts by weight per part by weight of the fluorinated alkoxy-substituted aniline.

The acetylation reaction can be preferably carried out at 50° to 120° C. for 1 to 10 hours to yield an acetanilide compound.

Examples of the halogenated benzene compound are iodotoluenes such as iodobenzene; iodotoluenes such as 3- or 4-iodotoluene; iodoxylidines; iodoanisoles such as 3-iodoanisole, 4-iodoanisole; iodobiphenyls such as 4-iodobiphenyl, 4'-methyl-4-iodobiphenyl, etc.

The acetanilide compound is preferably used in an amount of 0.1 to 10 moles, more preferably 0.3 to 3 moles, per mole of the halogenated benzene compound.

As the copper catalyst, there can be used a copper powder, copper oxide, copper halide, etc. Among them, the use of a copper powder, copper (I) oxide, copper (II) oxide, copper (I) iodide is preferable. The copper catalyst is used in an amount of preferably 0.05 to 5 moles, more preferably 0.1 to 2 moles, per mole of the halogenated benzene compound.

As the basic compound used as a catalyst, there can be used hydroxides or carbonates of alkali metals such as sodium hydroxide, potassium hydroxide, sodium carbonate, potassium carbonate, etc. Among them, the use of potassium hydroxide or potassium carbonate is preferable. The basic compound is used in an amount of preferably 0.1 to 10 moles, more preferably 0.3 to 3 moles, per mole of the halogenated benzene compound.

The condensation reaction can be carried out, if necessary, in an organic solvent. Examples of the solvent are nitrobenzene, dichlorobenzene, quinoline, N,N-dimethylformamide, dimethylsulfoxide, N-methyl-2-pyrrolidone, 1,3-dimethyl-2-imidazolidinone, etc., alone or as a mixture thereof. The organic solvent is preferably used in an amount of 0.2 to 10 parts by weight, more preferably 0.5 to 5 parts by weight, per part by weight of the halogenated benzene compound.

The condensation reaction can be carried out at preferably 120° to 280° C., more preferably 150° to 250° C., for 2 to 48 hours.

The hydrolysis of the condensation reaction product is preferably carried out in a 1 to 80% alkaline aqueous solution, and if necessary, together with a water-soluble organic solvent inert to the reaction system such as ethanol, methanol, acetone, acetonitrile, tetrahydrofuran, dimethylsulfoxide, etc., at 50° to 150° C. for 2 to 12 hours.

Examples of hydroxides of alkali metals used for preparing the alkaline aqueous solution are potassium hydroxide, sodium hydroxide, etc. and those of carbonates of alkali metals are potassium carbonate, sodium carbonate, etc. Among them, the use of potassium hydroxide or potassium carbonate is preferable.

The hydrolysis reaction product is subjected to extraction, filtration, washing and recrystallization or distillation under reduced pressure to yield the desired diarylamine compound.

Concrete examples of the diarylamine compound of the formula:

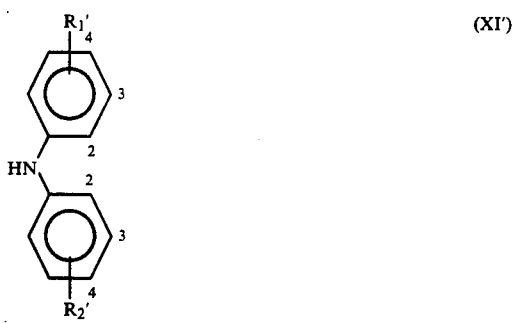 (XI')

are listed in Table 1.

TABLE 1

| Compound No. | R1 | R2 |
| --- | --- | --- |
| XI-1 | 4-OCF₃ | H |
| XI-2 | 4-OCF₃ | 3-CH₃ |
| XI-3 | 4-OCF₃ | 4-CH₃ |
| XI-4 | 4-OCF₃ | 3-OCH₃ |
| XI-5 | 4-OCF₃ | 4-OCH₃ |
| XI-6 | 4-OCF₃ | 3-CF₃ |
| XI-7 | 3-OCF₃ | H |
| XI-8 | 3-OCF₃ | 3-CH₃ |
| XI-9 | 3-OCF₃ | 4-CH₃ |
| XI-10 | 3-OCF₃ | 3-OCH₃ |
| XI-11 | 3-OCF₃ | 4-OCH₃ |
| XI-12 | 3-OCF₃ | 3-CF₃ |
| XI-13 | 4-OCH₂F₃ | H |

TABLE 1-continued

| Compound No. | R1 | R2 |
| --- | --- | --- |
| XI-14 | 4-OCH₂F₃ | 3-CH₃ |
| XI-15 | 4-OCH₂F₃ | 4-CH₃ |
| XI-16 | 3-OCH₂F₃ | H |
| XI-17 | 3-OCH₂F₃ | 3-CH₃ |
| XI-18 | 3-OCH₂F₃ | 4-CH₃ |
| XI-19 | 4-OCH₂F₃ | 3-OCH₃ |
| XI-20 | 4-OCH₂F₃ | 4-OCH₃ |
| XI-21 | 4-OCH₂F₃ | 3-OC₂H₅ |
| XI-22 | 4-OCH₂F₃ | 4-OC₂H₅ |
| XI-23 | 4-OCH₂F₃ | 4-Ph |
| XI-24 | 4-OCH₂F₃ | 4-(4'-CH₃ Ph) |
| XI-25 | 4-OCH₂F₃ | 4-(4'-C₂H₅ Ph) |
| XI-26 | 4-OCH₂F₃ | 3-CH₃, 4-CH₃ |
| XI-27 | 3-OCH₂F₃ | 3-OCH₃ |
| XI-28 | 3-OCH₂F₃ | 4-OCH₃ |
| XI-29 | 3-OCH₂F₃ | 3-OC₂H₅ |
| XI-30 | 3-OCH₂F₃ | 4-OC₂H₅ |
| XI-31 | 3-OCH₂F₃ | 4-Ph |
| XI-32 | 3-OCH₂F₃ | 4-(4'-CH₃ Ph) |
| XI-33 | 3-OCH₂F₃ | 4-(4'-C₂H₅ Ph) |
| XI-34 | 3-OCH₂F₃ | 3-CH₃, 4-CH₃ |

Ph = phenyl

The fluorine-containing N,N,N'-N'-tetraarylbenzidine derivative of the formula (I) thus produced can take independently as $R_1$ and $R_2$ a hydrogen atom; an alkyl group preferably having 1 to 6 carbon atoms such as methyl, ethyl, n-propyl, isopropyl, n-butyl, tert-butyl, etc.; an alkoxy group preferably having 1 to 6 carbon atoms such as methoxy, ethoxy, n-propoxy, isopropoxy, etc.; a fluoroalkyl group preferably having 1 to 6 carbon atoms such as trifluoromethyl, trifluoroethyl, trifluoropropyl, etc.; a fluoroalkoxy group preferably having 1 to 6 carbon atoms such as trifluoromethoxy, 2,2-difluoroethoxy, 2,2,2-trifluoroethoxy, 1H,1H-pentafluoropropoxy, hexafluoroisopropoxy, 1H,1H-heptafluorobutoxy, 2,2,3,4,4,4-hexafluorobutoxy, 4,4,4-trifluorobutoxy, etc.; and at least one of $R_1$ and $R_2$ being a fluoroalkyl group or a fluoroalkoxy group; and as $Ar^1$ and $Ar^2$ an aryl group such as a phenyl group, a biphenyl group, a terphenyl group, a naphthyl group, etc., said aryl group being able to have one or more substituents other than $R_1$ and $R_2$.

Examples of the substituent other than $R_1$ and $R_2$ are a halogen atom such as chlorine, fluorine, etc.; an alkyl group such as methyl, ethyl, n-propyl, isopropyl, n-butyl, tert-butyl, etc.; an alkoxy group such as methoxy, ethoxy, n-propoxy, isopropoxy, etc.; an aryl group such as phenyl, tolyl, etc.

Preferable examples of the fluorine-containing N,N,N',N'-tetraarylbenzidine derivative of the formula (I) are as follows.

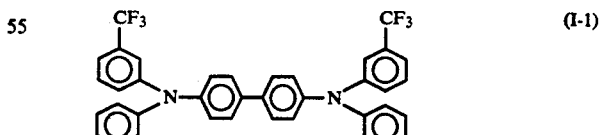 (I-1)

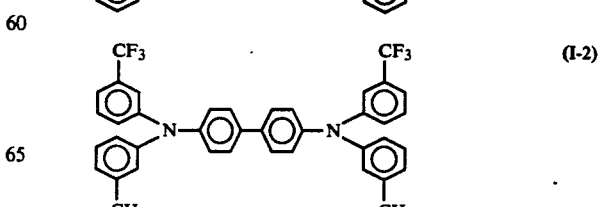 (I-2)

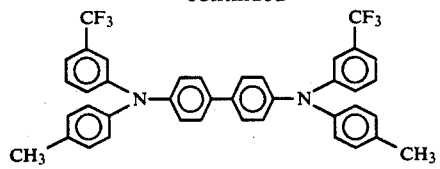 (I-3)
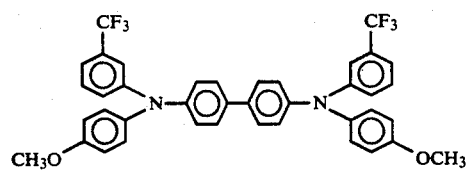 (I-4)
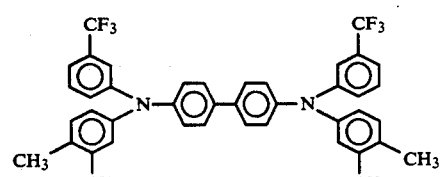 (I-5)
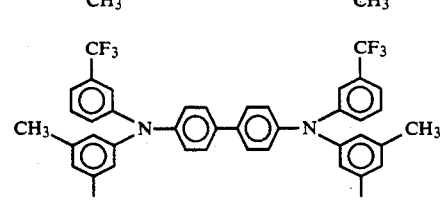 (I-6)
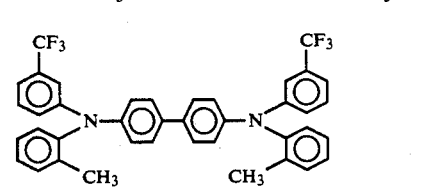 (I-7)
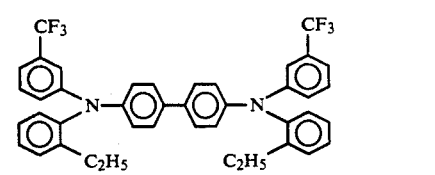 (I-8)
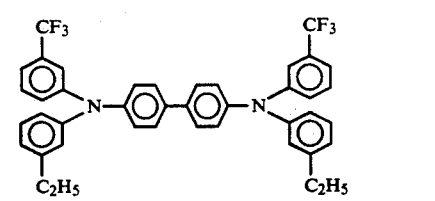 (I-9)
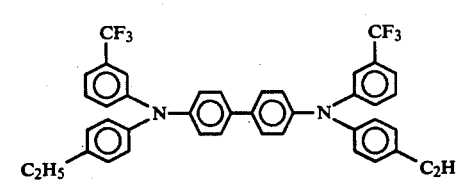 (I-10)
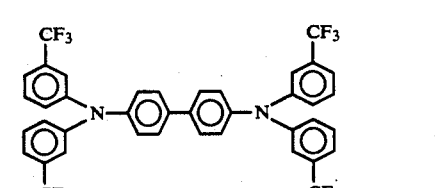 (I-11)
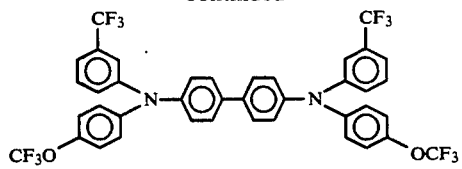 (I-12)
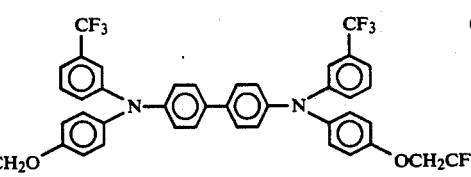 (I-13)
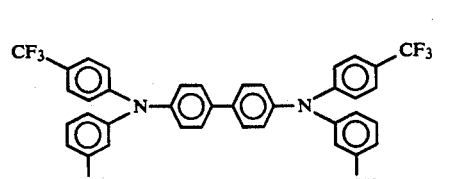 (I-14)
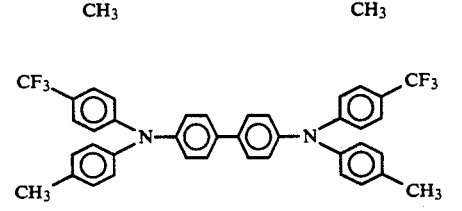 (I-15)
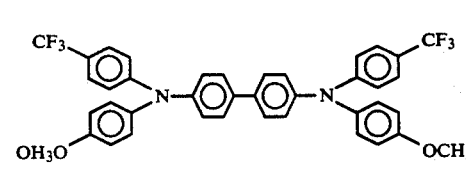 (I-16)
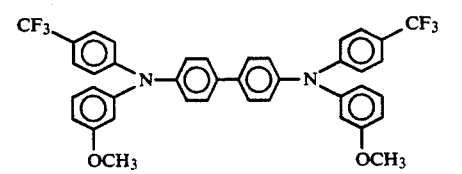 (I-17)
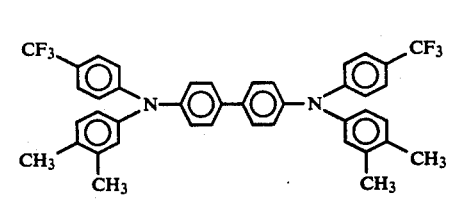 (I-18)
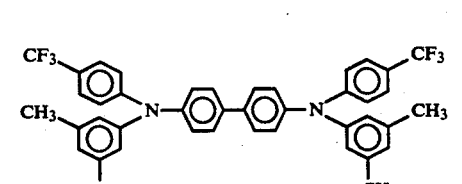 (I-19)
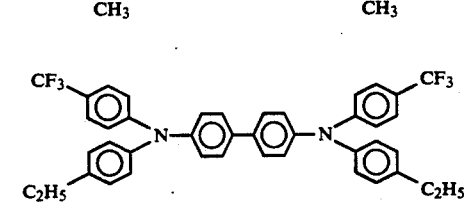 (I-20)

-continued (I-21)
(I-22)
(I-23)
(I-24)
(I-25)
(I-26)
(I-27)
(I-28)
(I-29)
(I-30)
(I-31)
(I-32)
(I-33)
(I-34)
(I-35)
(I-36)
(I-37)
(I-38)

-continued

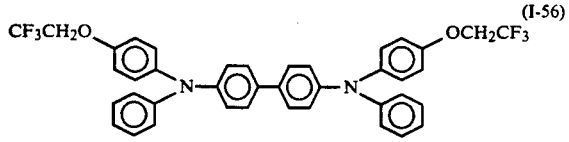

(I-56)

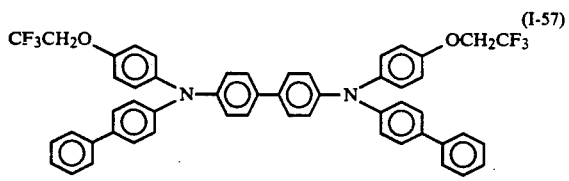

(I-57)

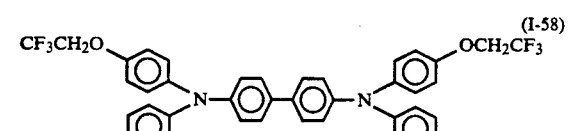

(I-58)

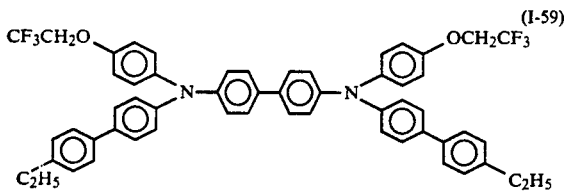

(I-59)

The fluorine-containing N,N,N',N'-tetraarylbenzidine derivative of the formula (I) can be used as a charge transport material in an electrophotographic member.

The electrophotographic member can take a single layer type comprising an electroconductive support and formed thereon a photoconductive layer containing a charge generation material, a fluorine-containing N,N,N',N'-tetraarylbenzidine derivative of the formula (I) as a charge transport material and a binder. The electrophotographic member can take a laminated type comprising a charge generation layer containing a charge generation material and a charge transport layer containing a fluorine-containing N,N,N',N'-tetraarylbenzidine derivative of the formula (I) and a binder formed on an electroconductive support. If necessary, an undercoating layer can be present between the electroconductive support and the photoconductive layer.

In the photoconductive layer, there can be used conventionally used additives such as a binder, a plasticizer, a fluidity imparting agent, a pinhole inhibitor, etc.

As the binder, there can be used styreneacrylonitrile copolymers, acrylate resins, polystyrene resins, unsaturated polyester resins, polyester carbonate resins, polycarbonate resins, polycarbonate copolymers, polyvinyl acetal resins, polyvinyl butyral resins, vinyl chloride-acrylic ester copolymers, vinyl chloride-vinyl acetate copolymers, polyketone resins, silicone resins, polyurethane resins, poly-N-vinyl carbazole, poly(p-vinylphenyl)anthracene, polyamide resins, polyvinyl pyrene, polyvinyl acridine, polyvinyl pyrazoline, epoxy resins, phenol resins, polyether resins, polyformal resins, poly(2,6-dimethylphenylene oxide), etc.

Among these binders, polyester resins, polyester carbonate resins, polycarbonate resins, polycarbonate copolymers, polyvinyl acetal resins, polyvinyl butyral resins, silicone resins, polyformal resins, and poly(2,6-dimethylphenylene oxide) are preferred. Further, polyester resins, polyester carbonate resins, polycarbonate resins, polycarbonate copolymers and polyvinyl acetal resins are particularly preferred.

Preferable examples of the polycarbonate resins are those having a weight average molecular weight of 20,000 to 150,000 and represented by the formulae:

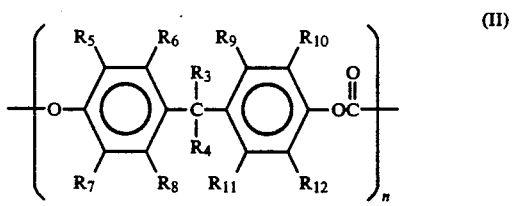

(II)

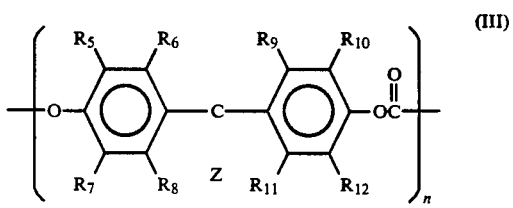

(III)

wherein $R_3$ and $R_4$ are independently hydrogen, halogen, an alkyl group or an aryl group, e.g. chlorine, fluorine, bromine, methyl, ethyl, phenyl, naphthyl, etc., $R_5$, $R_6$, $R_7$, $R_8$, $R_9$, $R_{10}$, $R_{11}$, and $R_{12}$ are independently a hydrogen atom, a halogen atom, an alkyl group or an aryl group as defined above; Z is a residue for forming a carbon ring which may have one or more substituents such as a hydrogen atom, a halogen atom, an alkyl group, an acyl group, a carboxylic ester group or an aryl group, e.g. chlorine, fluorine, bromine, methyl, ethyl, acetyl, carboxylic butyl ester, phenyl, naphthyl, etc.; or a heterocyclic ring such as

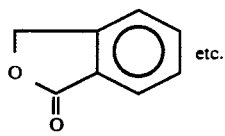 etc.

which may have one or more substituents such as a hydrogen atom, a halogen atom, an alkyl group, an acyl group, a carboxylic ester group or an aryl group such as defined above: and n is an integer for obtaining the desired molecular weight. In the formulae (II) and (III), the terminal groups change depending on the materials used and usually are a phenolic hydroxyl group, an alkyloxy group,

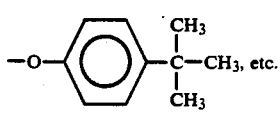, etc.

Concrete preferable examples of the polycarbonate resins of the formulae (II) and (III) are as follows:

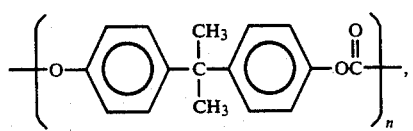
(II-1)

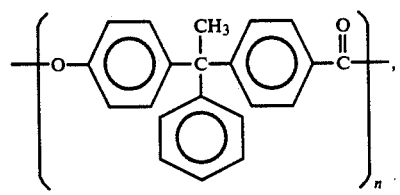
(II-2)

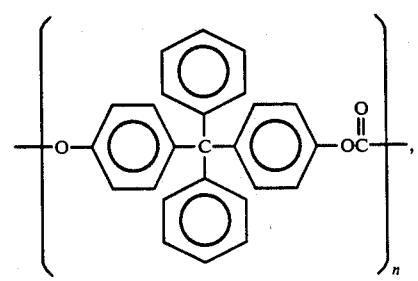
(II-3)

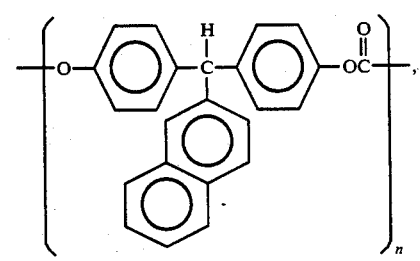
(II-4)

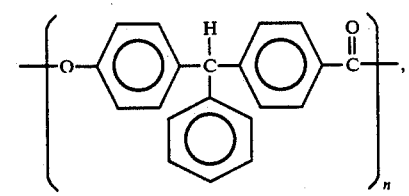
(II-5)

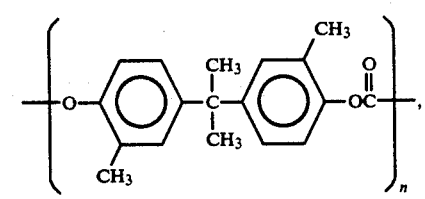
(II-6)

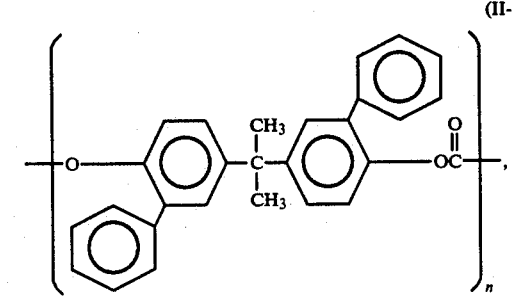
(II-7)

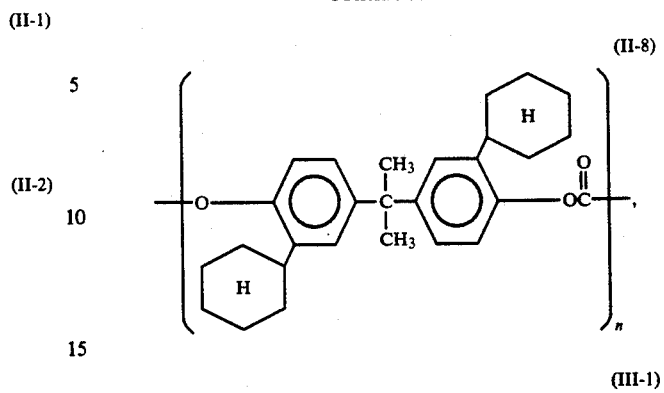
(II-8)

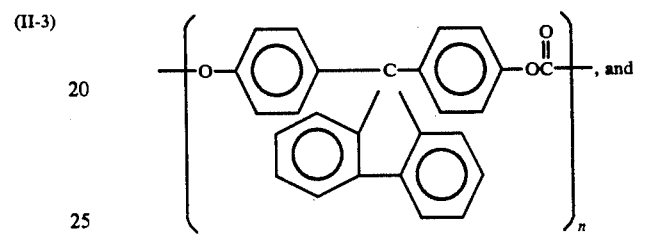
(III-1), and

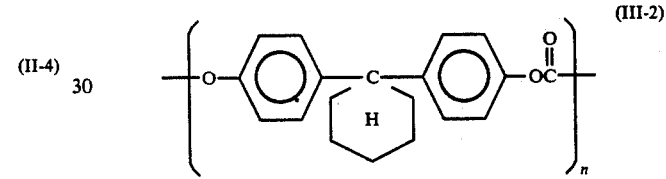
(III-2)

Among them, these polycarbonates represented by the formulae (II-2), (II-3), (II-5) and (II-7) are preferred.

Preferable examples of the polycarbonate copolymers are those having a weight average molecular weight of 20,000 to 120,000 and represented by the formula:

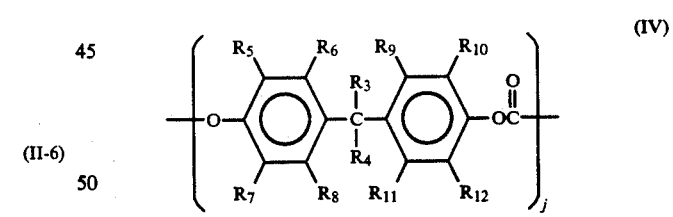
(IV)

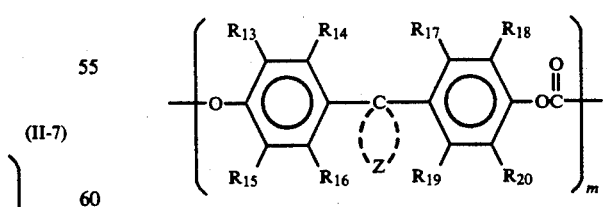

wherein $R_3$ through $R_{12}$ and Z are as defined above; $R_{13}$ through $R_{20}$ are independently a hydrogen atom, a halogen atom, an alkyl group or an aryl group; and a copolymerization ratio j/m is 1/10 to 10/1.

Concrete preferable examples of the polycarbonate copolymers of the formula (IV) are as follows:

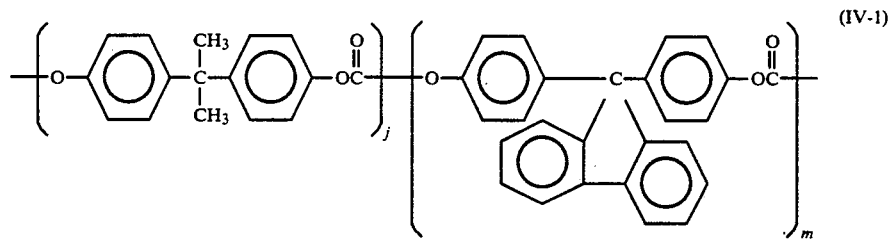
(IV-1)
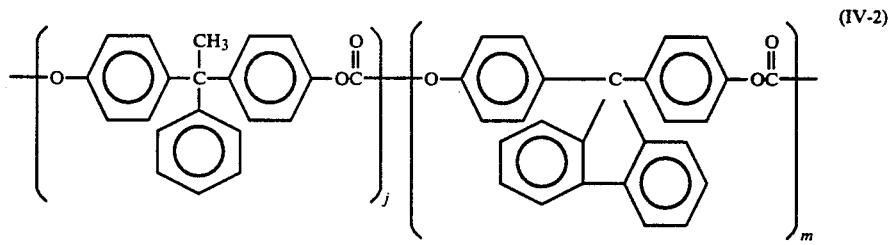
(IV-2)
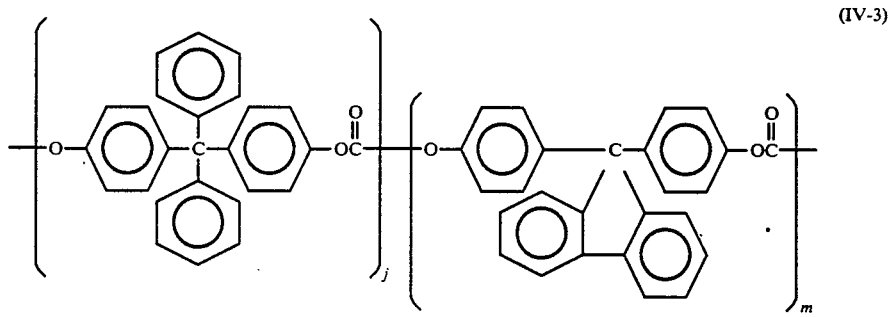
(IV-3)
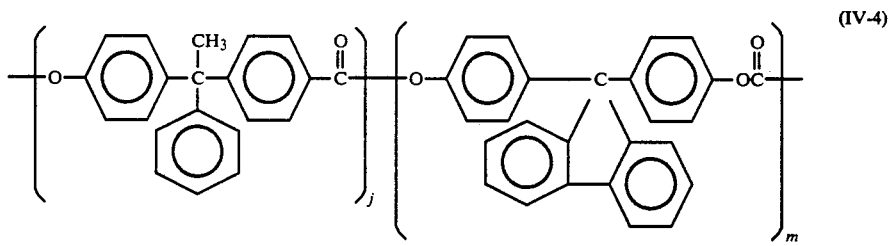
(IV-4)
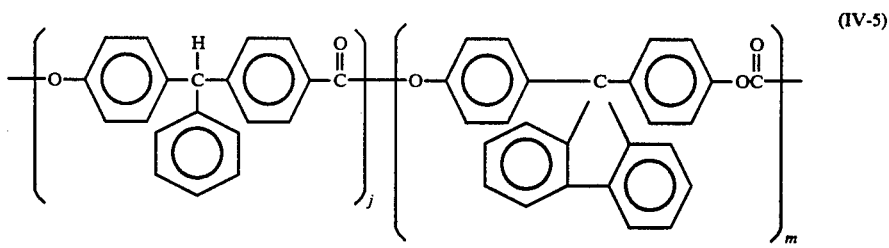
(IV-5)
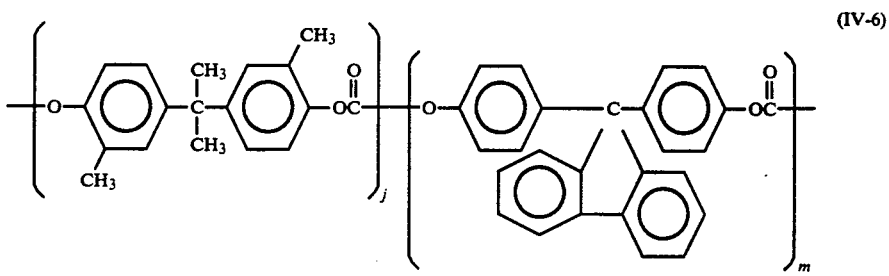
(IV-6)
In the formulae (IV-1) through (IV-8), j:m=1:1 to 9:1.

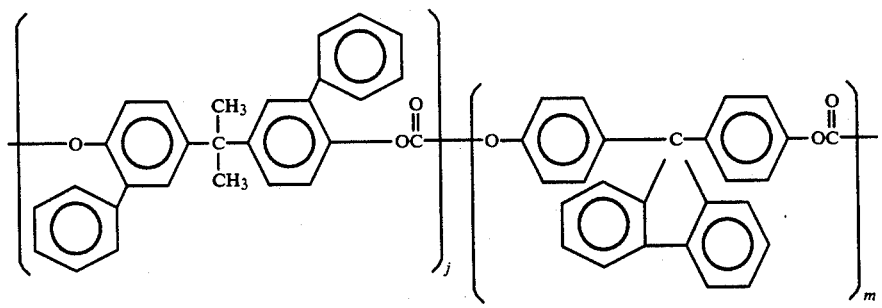
(IV-7)
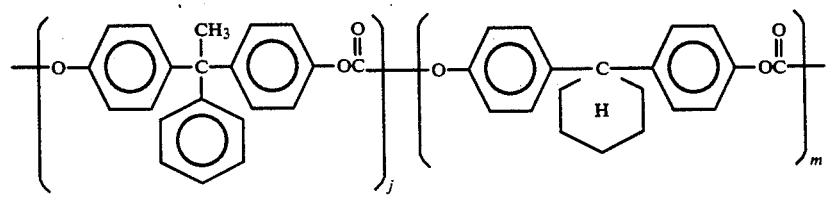
(IV-8)
Preferable examples of the polyester carbonate resins are those having a molecular weight of 20,000 to 120,000 (weight average) and represented by the formulae:
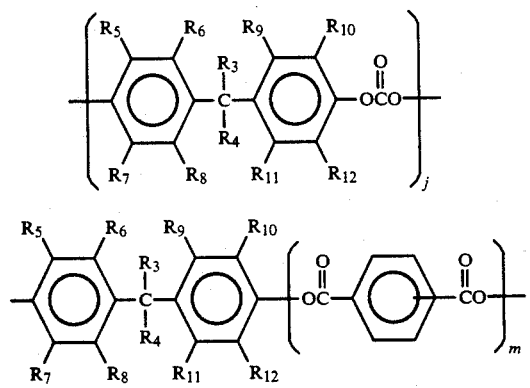
(V)
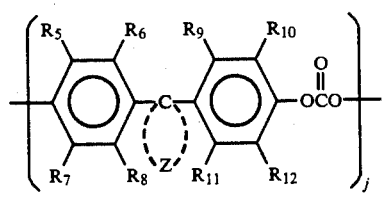
(VI)
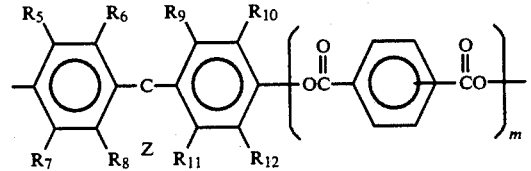
wherein $R_3$ through $R_{12}$, and z are as defined above; and a copolymerization ratio j/m is 1/1 to 10/1.
Concrete preferable examples of the polyester carbonate resins of the formulae (V) and (VI) are as follows:
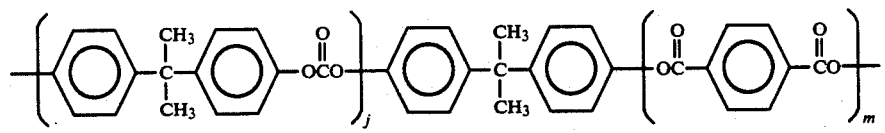
(V-1)
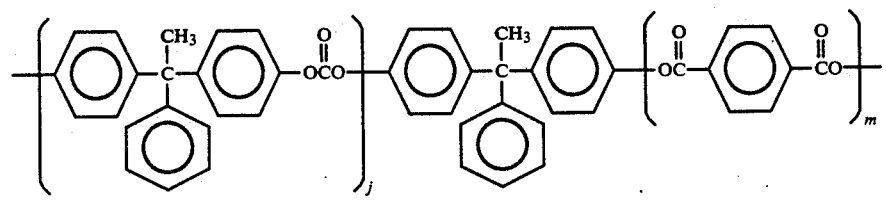
(V-2)

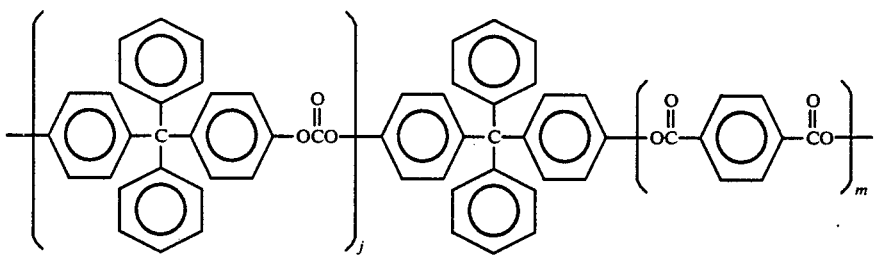
(V-3)

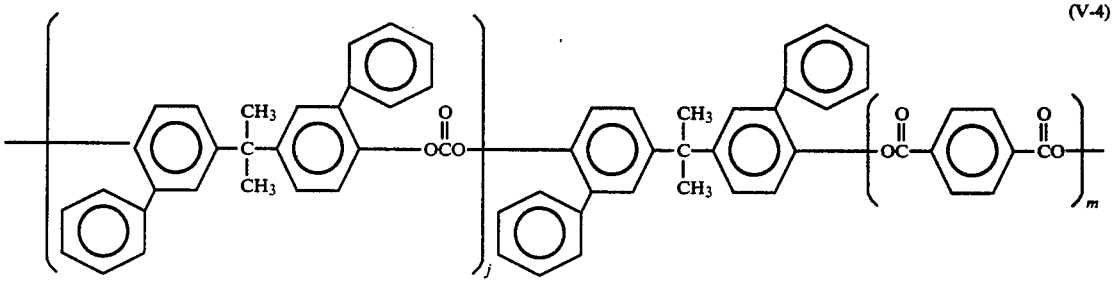
(V-4)

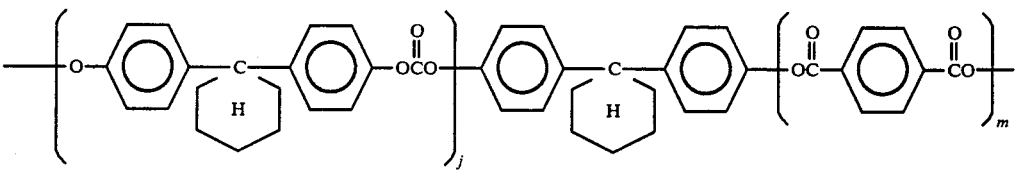
(VI-1)

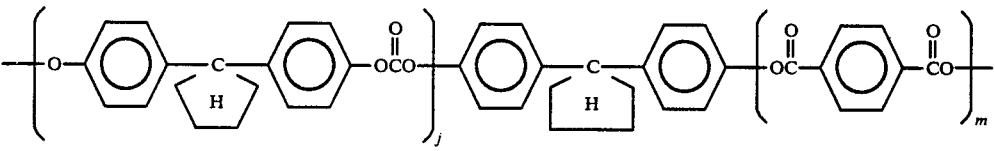
(VI-2)

As the binder, it is also possible to use thermosetting or photocurable resins which can be crosslinked by heat and/or light, has insulating properties and film forming properties.

Examples of the plasticizer are biphenyl, 3,3', 4,4'-tetramethyl-1,1-biphenyl, 3,3", 4,4"-tetramethyhl-p-terphenyl, 3,3",4,4"-tetramethyl-m-terphenyl, halogenated paraffins, dimethyl naphthalene, dibutyl phthalate, etc.

As the fluidity imparting agent, there can be used Modaflow (a trade name, mfd. by Monsanto Chemical Co.); Akulonal 4F (a trade name, mfd. by BASF AG.), DC3PA (a trade name, mfd. by Toray Silicone Co.); FC-170C, FC-430, FC-431 (trade names, mfd. by 3M Co.) etc.

As the pinhole inhibitor, there can be used benzoine, dimethyl terephthalate, etc.

In the present invention, since the fluorine-containing N,N,N',N'-tetraarylbenzidine derivative of the formula (I) is used as a charge transfer material, the electrophotographic member is high in sensitivity and is not deteriorated in charging characteristics, dark decay, sensitivity and image quality with the lapse of time even if repeatedly used.

If necessary, it is possible to use one or more other charge transport materials than the fluorine-containing N,N,N',N'-tetraarylbenzidine of the formula (I) so far as not lowering the above-mentioned electrophotographic properties.

Examples of co-usable other charge transport materials are as follows:
(i) Polymeric compounds:
poly-N-vinyl carbazole,
halogenated poly-N-vinyl carbazole,
polyvinyl pyrene,
polyvinyl indroquinoxaline,
polyvinyl benzothiophene,
polyvinyl anthracene,
polyvinyl acridine,
polyvinyl pyrazoline, etc.
(ii) Low molecular weight compounds:
fluorene,
fluorenone,
2,7-dinitro-9-fluorenone,
2,4,7-trinitro-9-fluorenone,
4H-indeno(1,2,6)thiophen-4-one,
3,7-dinitro-dibenzothiophenone-5-oxide,
1-bromopyrene,
2-phenylpyrene,
carbazole,
3-phenylcarbazole
2-phenylindole,
2-phenylnaphthalene,
oxadiazole,
triazole,
1-phenyl-3-(4-diethylaminostyryl)-5-(4-diethylaminophenyl)pyrazoline,
2-phenyl-4-(4-diethylaminophenyl)-5-phenyloxazole, triphenylamine,
imidazole,
chrysene,
tetraphene, acridine,
4-N',N'-diphenylaminobenzaldehyde-N,N-diphenylhydrazone,
4-N',N'-ditolylaminobenzaldehyde-N,N-diphenylhydrazone,
4-N',N'-diphenylamino-2-methylbenzaldehyde-N,N-diphenylhydrazone,
4-N',N'-dibenzylaminobenzaldehyde-N,N-diphenylhydrazone,
1,1-bis(p-diethylaminophenyl)-4,4-diphenyl-1,3-butadiene,
N,N,N',N'-tetraphenylbenzidine,
N,N'-diphenyl-N,N'-bis(3-methylphenyl)benzidine,
N,N'-di-2-naphthyl-N,N'-bis(3-methyphenyl)benzidine,
N,N,N',N'-tetrakis(4-methylphenyl)benzidine,
N,N'-diphenyl-N,N'-bis(4-methoxyphenyl)benzidine,
N,N,N',N'-tetrakis(4-methylphenyl)tolidine, etc.

Other charge transport material can be used preferably 1 part by weight or less, more preferably 0.25 part by weight or less per part by weight of the fluorine-containing N,N,N',N'-tetraarylbenzidine derivative of the formula (I) in order to not damage the improvement in electrophotographic properties due to the fluorine-containing N,N,N',N'-tetraarylbenzidine derivative of the formula (I).

As the charge generation material, there can be used Si, Se, $As_2S_3$, $Sb_2S_3$, $Sb_2Se_3$, CdS, CdSe, CdTe, ZnO, α-form, β-form, γ-form, and χ-form crystalline type non-metallic phthalocyanines, metal phthalocyanines such as copper phthalocyanine, aluminum phthalocyanine, zinc phthalocyanine, titanyl phthalocyanine, cobalt phthalocyanine, and naphthalocyanine pigments, azo pigments, indigoid pigments, quinacridone pigments, perylene pigments, mult-ring quinone pigments, squaric acid methine pigments, azulene pigments, pyrrolopyrrole pigments, etc. It is also possible to use other pigments disclosed in, for example, Japanese Patent Unexamined Publication Nos. 47-37453, 47-37544, 47-18543, 47-18544, 48-43942, 48-70538, 49-1231, 49-105536, 50-75214, 50-92738, 61-162555, 63-20365, 1-45474, 2-175763, etc. Among them, non-metal phthalocyanines and titanyl phthalocyanines are preferable.

It is further possible to use phthalocyanines represented by the formula:

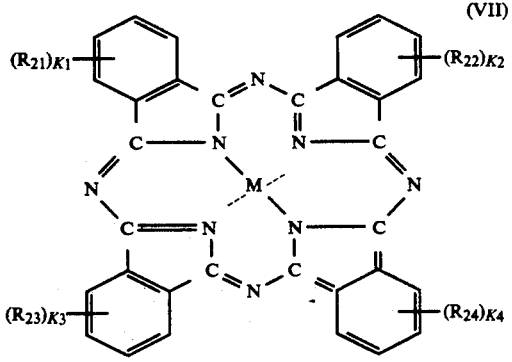

(VII)

wherein M is $H_2$ and/or TiO; $R_{21}$, $R_{22}$, $R_{23}$ and $R_{24}$ are independently a hydrogen atom, a halogen atom, an alkyl group or an alkoxy group; and $K_1$, $K_2$, $K_3$ and $K_4$ are independently an integer of 1 to 4.

Preferable examples of the phthalocyanines of the formula (VII) are τ-form non-metal phthalocyanine, χ-form non-metal phthalocyanine, α-form titanyl phthalocyanine, β-form titanyl phthalocyanine, titanyl phthalocyanine showing a strong diffraction peak at Bragg angle $2\theta = 27.3° \pm 0.2°$ in X-ray diffraction pattern (Japanese Patent Unexamined Publication No. 63-20365), alone or as a mixture thereof. Among them, β-form titanyl phthalocyanine which shows strong diffraction peaks at Bragg angles ($2\theta \pm 0.2°$) of 9.3°, 10.6°, 13.2°, 15.1°, 15.7°, 16.1°, 20.8°, 23.3°, 26.3° and 27.1° in X-ray diffraction pattern is particularly preferable.

In the single layer type photoconductive layer, preferably 1 to 10 parts by weight, more preferably 1 to 5 parts by weight of charge transport material per part by weight of the charge generation material is used.

The binder is used in an amount of 1 to 3 parts by weight per part by weight of the charge generation material. When the amount is more than 3 parts by weight, there is a tendency to lower electrophotographic properties. Further, it is possible to contain several percents by weight or less of plasticizer and the like additives based on the weight of the charge generation material.

The thickness of the photoconductive layer is preferably 5 to 100 μm, and is determined finally so as not to damage photo sensitivity, that is, charging characteristics.

On the other hand, in the laminated type photoconductive layers comprising a charge generation layer and a charge transport layer, the charge generation layer can be formed either by vacuum deposition of the charge generation material, or by coating a coating solution containing a charge generation material and a binder, followed by drying.

As the binder used in the charge generation layer together with the charge generation material, there can be preferably used, among the binders mentioned above, polyester resins, polyvinyl acetal resins, polyvinyl butyral resins, vinyl chloride-acrylic ester copolymers, vinyl chloride-vinyl acetate copolymers, silicone resins, and phenol resins. Among them, polyester resins and polyvinyl acetal resins are particularly preferable.

Concrete examples of the polyester resins used in the charge generation layer are Vylon 200, Vylon 290 (trade names, mfd. by Toyobo Co., Ltd.)

Concrete examples of the polyvinyl acetal resins used in the charge generation layer are Eslex BL-S, Eslex BM-1, Eslex BM-2, Eslex BM-S, Eslex BH-3, Ezlex BH-S, Eslex KS-1, Eslex KS-5 (trade names, mfd. by Sekisui Chemical Co., Ltd.).

It is also possible to use thermosetting or photocurable resins which are crosslinked by heat or light as a binder in the charge generation layer.

The amount of the binder in the charge generation layer is preferably 0.5 to 3 parts by weight per part by weight of the charge generation material. When the amount is more than 3 parts by weight, there is a tendency to lower electrophotographic properties.

Further, it is possible to use several percents by weight or less of plasticizer and the like additives based on the weight of the charge generation material.

In the charge transport layer, since the fluorine-containing N,N,N',N'-tetraarylbenzidine derivative of the formula (I) is excellent in solubility in the binder, when such a compound of the formula (I) is used alone as a charge transport material, the binder is used in an amount of 0.5 to 3 parts by weight per part by weight of the charge transport material. When other charge transport material is used together, no binder can be used when a polymeric compound is used as the charge transport material, but it is possible to use a binder in an amount of 3 parts by weight or less per part by weight of the polymeric compound. When the amount is more than 3 parts by weight, there is a tendency to lower electrophotographic properties.

On the other hand, when a low molecular weight compound is used as a charge transport material together with the fluorine-containing N,N,N',N'-tetraarylbenzidine derivative of the formula (I), the binder is preferably used in an amount of 0.5 to 3 parts by weight per part by weight of the total of the low molecular weight compound and the fluorine-containing N,N,N',N'-tetraarylbenzidine derivative of the formula (I). When the amount is less than 0.5 part by weight, the formation of charge transport layer becomes difficult, while when the amount is more than 3 parts by weight, there is a tendency to lower electrophotographic properties.

The charge transport layer may further contain a plasticizer and the like additives in amounts of 0.05 part by weight or less per part by weight of the charge transport material.

The thickness of the charge generation layer is usually 0.01 to 10 µm, preferably 0.1 to 5 µm. When the thickness is less than 0.01 µm, it is difficult to form the charge generation layer uniformly. When the thickness is more than 10 µm, there is a tendency to lower electrophotographic properties.

The thickness of the charge transport layer is usually 5 to 50 µm, preferably 10 to 35 µm. When the thickness is less than 5 µm, there is a tendency to lower initial potential, while when the thickness is more than 50 µm, there is a tendency to lower the sensitivity.

In either case, the thickness is determined finally so as not to damage the photo sensitivity, that is, charging properties. When the thickness of photoconductive layer is too thick, a care should be taken since there is a tendency to lower flexibility of the layer per se.

When the electrophotographic member of the present invention takes the laminated type, it is preferable to form the charge generation layer on the electroconductive support, followed by formation of the charge transport layer on the charge generation layer from the viewpoint of electrophotographic properties. But the order of the charge generation layer and the charge generation layer can be reversible.

As the electroconductive support, there can be used a metal plate made of aluminum, brass, copper, gold, etc., and metal-deposited Mylar film, etc.

In the case of forming a single layer containing a charge generation material and a charge transport material, or forming a charge generation layer and a charge transport layer, on the electroconductive support, the components of each layer are dissolved or dispersed uniformly in a solvent, and coated on an electroconductive support, followed by drying. As the solvent, there can be used ketones such as acetone, methyl ethyl ketone, etc.; ethers such as tetrahydrofuran, etc.; halogenated hydrocarbons such as methylene chloride, 1,2-dichloroethane, 1,1,2-trichloroethane, etc.; aromatic hydrocarbons such as toluene, xylene, etc. When the laminated type is employed, a charge generation layer or a charge transport layer is formed first, followed by formation of a charge transport layer or a charge generation layer thereon and drying.

The coating and drying can be carried out by a coating method using an applicator, a dipping method, a coating method using a doctor blade, etc., to form a layer with the desired thickness, and natural drying for 15 minutes and heating at 50° to 150° C. for 30 to 90 minutes.

The electrophotographic member of the present invention may have an undercoating layer between the electroconductive support and the photoconductor layer in the case of single layer type, or between the electroconductive support and the charge generation layer or the charge transport layer in the case of laminated type.

As the undercoating layer, it is preferable to use a thermoplastic resin. Preferable examples of the thermoplastic resin include polyamide resins, polyurethane resins, polyvinyl butyral resins, melamine resins, casein, phenol resins, epoxy resins, ethylenevinyl acetate copolymer, ethylene-acrylic acid copolymer, etc. Among them, the polyamide resins are preferable.

Concrete examples of polyamide resins are Toresin MF30, Toresin F30, Toresin EF30T (trade names, mfd. by Teikoku Kagaku Sangyo K.K.), M-1276 (a trade name, mfd. by Nihon Rilsan K.K.), etc.

These resins can be used alone or as a mixture thereof in the undercoating layer.

When a polyamide resin is used for forming the undercoating layer, it is preferable to use one or more thermosetting resins and a curing agent together with the polyamide resin. By the co-use of the thermosetting resin and the curing agent, solvent resistance and film strength of the undercoating layer can be improved so as to lessen damages caused by a solvent and the like contained in the solution for forming the photoconductive layer on the undercoating layer.

As the thermosetting resin, there can be used any thermosetting resins which have a film forming ability at normal state, e.g. melamine resins, benzoguanamine resins, polyurethane resins, epoxy resins, silicone resins, polyester resins, acrylic resins, urea resins, etc. It is preferable to use the thermosetting resin in an amount of 300% of weight or less based on the weight of the thermoplastic resin.

As the curing agent, there can be used trimellitic acid, pyromellitic acid, and the like carboxylic acids, and oligomers of amides having carboxylic acid moiety, etc. It is preferable to use the curing agent in an amount of 20% by weight or less based on the weight of the thermosetting resin.

The undercoating layer can be formed by uniformly dissolving a thermoplastic resin, and if necessary, a thermosetting resin and a curing agent, etc. in a mixed solvent of an alcohol (e.g. methanol, ethanol, isopropanol, etc.) and a halogenated hydrocarbon (e.g. methylene chloride, 1,1,2-trichloroethane, etc.), coating the resulting solution on an electroconductive support by a dipping method, a spraying method, a roll coating method, an applicator coating method, a wire bar coating method, etc., followed by drying.

The thickness of the undercoating layer is preferably 0.01 µm to 5.0 µm, more preferably 0.05 µm to 2.0 µm. When the thickness is too small, no uniform charge generation layer is formed and there is a tendency to form small white stains and small black stains. On the other hand, when the thickness is too large, there is a tendency to lower printed letter density with an increase of printed sheets.

A conventional copying method can be applied to the electrophotographic member of the present invention, wherein the surface of the electrophotographic member is subjected to charging and exposure to light, development, and transferring an image on plain paper, followed by fixing.

The present invention is illustrated by way of the following examples, in which all parts and percents are by weight, unless otherwise specified.

SYNTHESIS EXAMPLES (1) Fluorine-containing N,N,N',N'-tetraarylbenzidine derivatives of the formula:

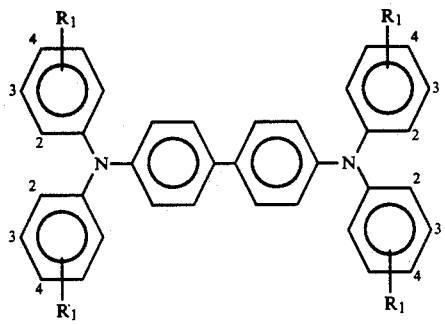

wherein $R_1$ and $R_2$ are as listed in Table 2 were synthesized.

TABLE 2

| Synthesis Example No. | $R_1$ | $R_2$ |
| --- | --- | --- |
| 1 | 3-$CF_3$ | H |
| 2 | 3-$CF_3$ | 3-$CH_3$ |
| 3 | 3-$CF_3$ | 4-$CH_3$ |
| 4 | 3-$CF_3$ | 4-$OCH_3$ |
| 5 | 3-$OCH_2CF_3$ | 4-$CH_3$ |
| 6 | 4-$OCF_3$ | 4-$CH_3$ |
| 7 | 4-$OCF_3$ | 4-$OCH_3$ |

SYNTHESIS EXAMPLE 1

Synthesis of N,N'-bis(3-trifluoromethylphenyl)-N,N'-diphenyl-[1,1'-biphenyl]-4,4'-diamine (Compound (I-1) used in Example 1)

In a 300-ml round bottom glass flask equipped with a thermometer, a condenser attaching a water separator and a stirrer, 100 mmole of 98.6% 4,4'-diiodobiphenyl, 300 mmole of 99.4% N-(3-trifluoromethylphenyl)aniline, 20.7 g of potassium carbonate and 8 g of a copper powder were placed and heated at 210° C. for 5 hours. The water generated by the reaction was taken out of the reaction system by the water separator.

After the reaction, the contents were diluted with 350 ml of toluene and insoluble materials were filtered off. The resulting toluene solution was concentrated under reduced pressure to give a brown oily material.

The brown oily material was purified by column chromatography (alumina/toluene) to obtain a pale yellow oily material, which was recrystallized from n-hexane to give white crystals of N,N'-bis(3-trifluoromethylphenyl)-N,N'-diphenyl-[1,1'-biphenyl]-4,4'-diamine in purity of 99.7% in an amount of 34.3 g (yield 54.9%), and having a m.p. 150.1° C.

Elementary analysis (for $C_{38}H_{26}F_6N_2$).

| | C (%) | H (%) | F (%) | N (%) |
| --- | --- | --- | --- | --- |
| Calcd. | 73.07 | 4.20 | 18.25 | 4.48 |
| Found | 73.26 | 4.15 | 19.18 | 4.50 |

FIG. 1 shows infrared absorption spectrum of N,N'-bis(3-trifluoromethylphenyl)-N,N'-diphenyl-[1,1'-biphenyl]-4,4'-diamine.

SYNTHESIS EXAMPLES 2 to 7

In place of N-(3-trifluoromethylphenyl)aniline used in Synthesis Example 1, the following diarylamine compounds shown in Table 3 were used and reacted at 200° to 220° C. for 24 to 48 hours.

TABLE 3

| Synthesis Example No. | Diarylamine |
| --- | --- |
| 2 | N-(3-trifluoromethylphenyl)-m-toluidine |
| 3 | N-(3-trifluoromethylphenyl)-p-toluidine |
| 4 | N-(3-trifluoromethylphenyl)-p-anisidine |
| 5 | N-3(2,2,2-trifluoroethoxyphenyl)-p-toluidine |
| 6 | N-(4-trifluoromethoxyphenyl)-p-toluidine |
| 7 | N-(4-trifluoromethoxyphenyl)-p-anisidine |

After the reaction, the contents were diluted with 350 ml of toluene and filtered to remove insoluble materials to give a toluene solution, which was concentrated under reduced pressure to give a brown oily material.

The brown oily material was treated with active carbon in a solvent and purified by column chromatography and recrystallization to yield a fluorine-containing N,N,N',N'-tetraarylbenzidine derivative as shown in Table 4 in purity of 99.6% or more.

FIGS. 2 to 7 show infrared absorption spectra of the fluorine-containing N,N,N',N'-tetraarylbenzidine derivatives obtained in Synthesis Examples 2 to 7 (KBr tablet method).

Properties, elementary analysis results, etc. of the obtained products are shown in Table 4.

TABLE 4

| Synthesis Example No. | Yield (%) | Melting point (°C.) | Elementary analysis Empirical formula Calcd. (%)/ Found. (%) | | | |
| --- | --- | --- | --- | --- | --- | --- |
| | | | C (%) | H (%) | F (%) | N (%) |
| | | | $C_{40}H_{30}F_6N_2$ | | | |
| 2 | 25.6 | 157.7 | 73.61 | 4.63 | 17.46 | 4.29 |
| | | | 73.62 | 4.59 | 17.95 | 4.32 |
| | | | $C_{40}H_{30}F_6N_2$ | | | |
| 3 | 30.2 | 142.1 | 73.61 | 4.63 | 17.46 | 4.29 |
| | | | 73.60 | 4.62 | 18.80 | 4.30 |
| | | | $C_{40}H_{30}F_6N_2O_2$ | | | |
| 4 | 51.2 | 133.7 | 70.17 | 4.42 | 16.65 | 4.09 |
| | | | 70.13 | 4.33 | 18.20 | 4.14 |
| | | | $C_{42}H_{34}F_6N_2O_2$ | | | |
| 5 | 47.0 | 165.0 | 70.78 | 4.81 | 15.99 | 3.93 |
| | | | 70.75 | 4.77 | 16.49 | 4.10 |
| | | | $C_{40}H_{30}F_6N_2O_2$ | | | |
| 6 | 33.0 | 63.5 | 70.17 | 4.42 | 16.65 | 4.09 |
| | | | 70.20 | 4.35 | 16.08 | 4.17 |
| | | | $C_{40}H_{30}F_6N_2O_4$ | | | |
| 7 | 57.4 | 168.0 | 67.04 | 4.19 | 15.92 | 3.91 |
| | | | 67.15 | 4.09 | 16.39 | 4.00 |

(2) Secondary fluorinated alkoxy-substituted diphenylamines of the formula:

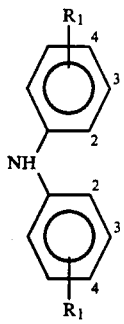

wherein $R_1$ is 4-OCF$_3$ and $R_2$ is 4-CH$_3$ (Synthesis Example 8) and $R_1$ is 4-OCF$_3$ and $R_2$ is 4-OCH$_3$ (Synthesis Example 9), were synthesized.

SYNTHESIS EXAMPLE 8

In a 500-ml round bottom glass flask equipped with a thermometer, a condenser and a stirrer, 180.7 g of p-trifluoromethoxyaniline in purity of 99.4% and 250 ml of glacial acetic acid were placed and heated to 55° C. in the liquid temperature. Then, 105 ml of acetic anhydride was added dropwise for 2 hours, then the temperature was maintained at 70° C. for 80 minutes.

After the reaction, the contents were concentrated under reduced pressure and dried to give white crystals of p-trifluoromethoxyacetanilide in purity of 100% in an amount of 219.0 g (yield 99.9%), having a melting point of 113.4° C.

In the next place, in a 500-ml round bottom glass flask equipped with a thermometer, a condenser attaching a water separator and a stirrer, 109.5 g of p-trifluoromethoxyacetanilide, 163.6 g of p-iodotoluene in purity of 99.8%, 103.7 g of potassium carbonate and 15 g of a copper powder were placed and maintained at 180° to 205° C. for 9 hours. The water generated by the reaction was taken out of the reaction system by the water separator.

After the reaction, the contents were cooled and added with 100 ml of dimethylsulfoxide and 100 ml of 40% aqueous solution of potassium hydroxide, followed by gradual heating to 70° to 125° C. for 6 hours.

After the reaction, the contents were diluted with 500 ml of toluene and extracted, and filtered to remove insoluble materials. The resulting toluene layer was washed with a 10% aqueous solution of sodium sulfate and water in this order.

Finally, the toluene was removed by evaporation under reduced pressure to recover a fraction of 134–6° C./3 Torr by vacuum distillation. As a result, white crystals of N-(4-trifluoromethoxyphenyl)-p-toluidine in purity of 99.6% were obtained in an amount of 87.5 g (yield 65.6%). Melting point was 43.7° C.

Elementary analysis (for $C_{14}H_{12}F_3NO$).

|  | C (%) | H (%) | F (%) | N (%) |
|---|---|---|---|---|
| Calcd. | 62.92 | 4.53 | 21.33 | 5.24 |
| Found | 63.08 | 4.40 | 21.80 | 5.29 |

Figure 8:
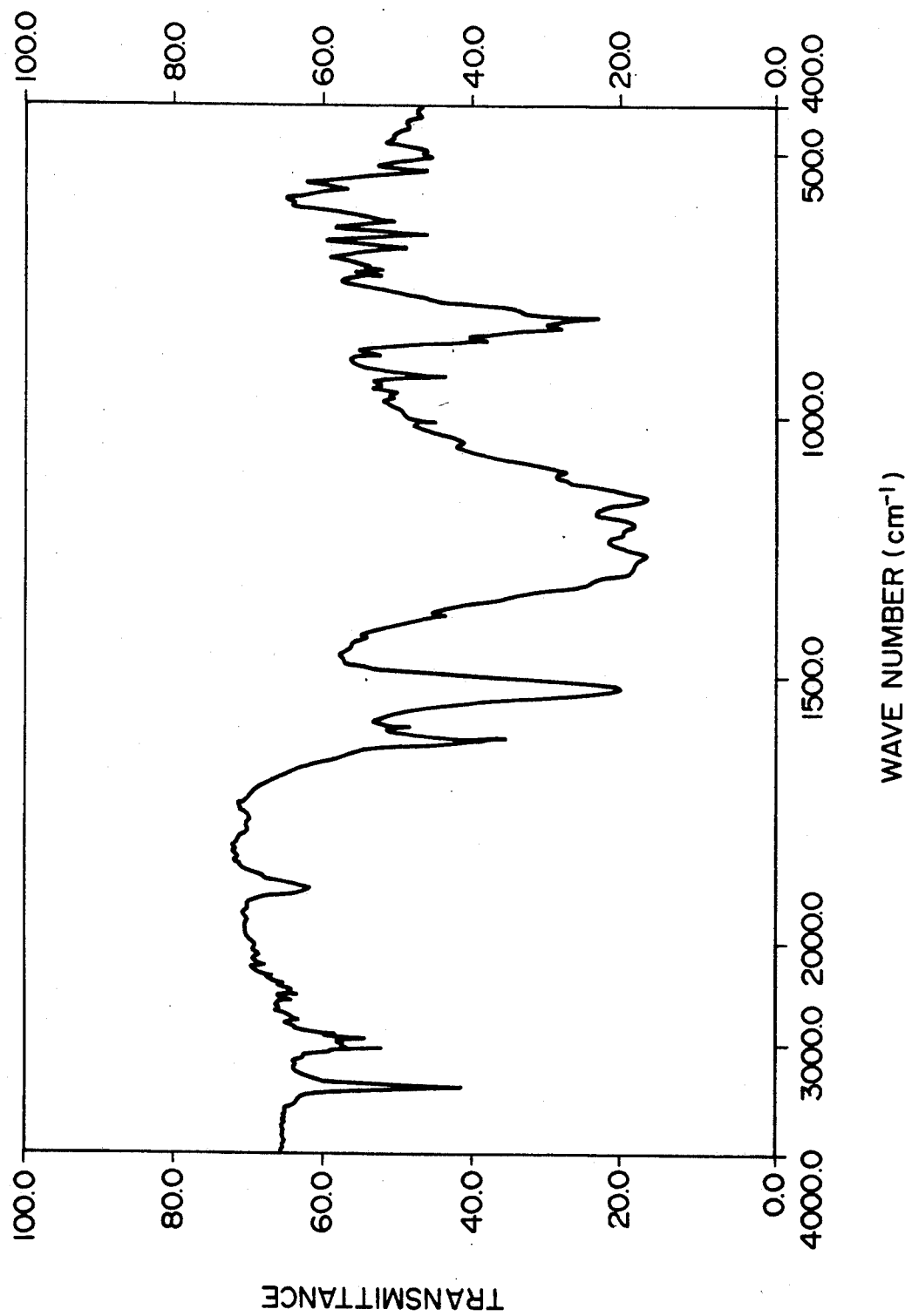
FIGS. 8, 9 and 18 to 22 are infrared absorption spectra of secondary fluorinated alkoxy-substituted diphenylamines obtained in Synthesis Examples 8, 9 and 17 to 21.

FIG. 8 shows an infrared absorption spectrum of N-(4-trifluoromethoxyphenyl)-p-toluidine (KBr tablet method).

SYNTHESIS EXAMPLE 9

The process of Synthesis Example 8 was repeated except for using 175.6 g of p-iodoanisole in purity of 100% in place of p-iodotoluene, and condensation reacting at 180° to 200° C. for 20 hours.

The hydrolysis and aftertreatment were conducted in the same manner as described in Synthesis Example 8. After removing the toluene by evaporation under reduced pressure, a fraction of 143° C./4 Torr was recovered by vacuum distillation to give a yellow liquid of N-(4-trifluoromethoxyphenyl)-p-anisidine in purity of 99.4% in an amount of 95.8 g (yield 67.3%).

Elementary analysis (for $C_{14}H_{12}F_3NO_2$).

|  | C (%) | H (%) | F (%) | N (%) |
|---|---|---|---|---|
| Calcd. | 59.37 | 4.27 | 20.12 | 4.94 |
| Found | 59.30 | 4.21 | 20.95 | 4.62 |

Figure 9:
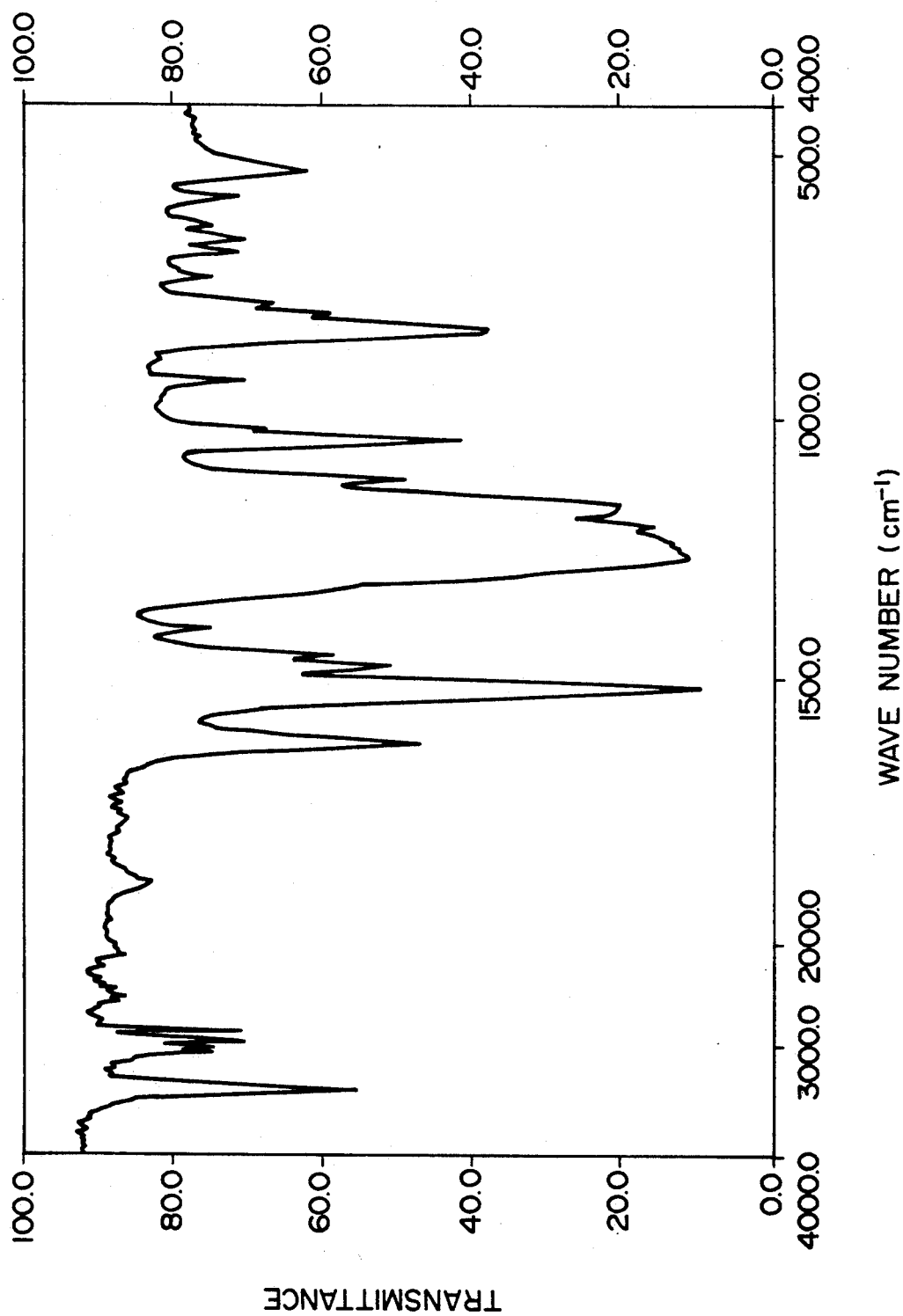

FIG. 9 shows an infrared absorption spectrum of N-(4-trifluoromethoxyphenyl)-p-anisidine.

EXAMPLES 1 TO 5

A mixture was obtained from 1 part of τ-form nonmetal phthalocyanine (mfd. by Toyo Ink Mfg. Co., Ltd.), 6.7 parts of silicone resin (KR-5240, a trade name, mfd. by Shin-Etsu Chemical Co., Ltd., solid content 15%) and 38.1 part of tetrahydrofuran. The resulting mixed solution was kneaded in a ball mill (a pot having a diameter of about 9 cm, mfd. by Nippon Kagaku Togyo Co., Ltd.) for 8 hours. The resulting dispersion was coated on an aluminum plate (100 mm × 700 mm and 0.1 mm thick) using an applicator and dried at 120° C. for 30 minutes to form a charge generation layer of 0.5 μm thick.

Then, 1.2 parts of a fluorine-containing N,N,N',N'-tetraarylbenzidine derivative of the formula (I) listed in Table 5 and 1.8 parts of bisphenol Z type polycarbonate resin (Z-200, a trade name, mfd. by Mitsubishi Gas Chemical Co., Ltd.) were dissolved in 17 g of 1,2-dichloroethane to give a coating solution, which was coated on the charge generation layer using an applicator, dried at 90° C. for 30 minutes to form a charge transport layer of 18 μm thick. As a result, a electrophotographic member was obtained.

The thus obtained electrophotographic member was subjected to measurement of electrophotographic properties using an electrostatic recording analyzer (SP-428, mfd. by Kawaguchi Electric Works Co., Ltd.). The results are shown in Table 5.

In Table 5, the potential $V_0$ (−V) means a charging potential when the electrophotographic member was subjected to corona discharge of −5 KV for 10 seconds in the dynamic measurement.

The dark decay ($V_K$) means a potential maintaining ratio from the potential ($V_{30}$) when allowed to stand in the dark for 30 seconds thereafter [($V_{30}/V_0$) × 100%].

The half decay exposure amount ($E_{50}$) means a light amount until the potential becomes half of $V_{30}$ when exposed to white light of 10 lux.

The residual potential ($V_R$) means a surface potential after exposed to white light of 10 lux for 30 seconds.

TABLE 5

| Example No. | Charge transport material | $V_0$ (−V) | $V_K$ (%) | $E_{50}$ (lux·sec) | $V_R$ (−V) |
|---|---|---|---|---|---|
| 1 | (CF₃-phenyl)(phenyl)N—biphenyl—N(phenyl)(CF₃-phenyl) | 980 | 77.6 | 1.2 | 0 |
| 2 | (CF₃-phenyl)(3-CH₃-phenyl)N—biphenyl—N(3-CH₃-phenyl)(CF₃-phenyl) | 1090 | 82.1 | 1.2 | 0 |
| 3 | (CF₃-phenyl)(4-CH₃-phenyl)N—biphenyl—N(4-CH₃-phenyl)(CF₃-phenyl) | 1140 | 82.5 | 1.2 | 0 |
| 4 | (CF₃-phenyl)(4-CH₃O-phenyl)N—biphenyl—N(4-CH₃O-phenyl)(CF₃-phenyl) | 1030 | 83.0 | 1.0 | 0 |
| 5 | (4-CF₃O-phenyl)(4-CH₃O-phenyl)N—biphenyl—N(4-CH₃O-phenyl)(4-OCF₃-phenyl) | 1035 | 79.2 | 1.2 | 0 |

COMPARATIVE EXAMPLE 1

An electrophotographic member was prepared in the same manner as described in Example 1 except for using the following compound in place of the benzidine derivative used in Example 1.

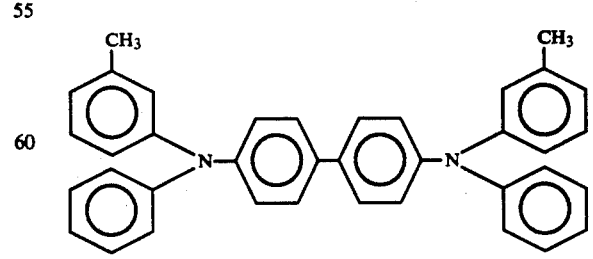

The above-mentioned compound was not dissolved in 1,2-dichloroethane completely, resulting in failing to obtain a coating solution.

EXAMPLES 6 AND 7

After forming a charge generation layer in the same manner as described in Example 1, a coating solution obtained by dissolving 1.2 parts of the benzidine derivative as listed in Table 6 and and 1.8 parts of bisphenol A type polycarbonate resin (Lexan 141, a trade name, mfd. by General Electric Co.) in a mixed solvent of 9 parts of methylene chloride and 8 parts of 1,1,2-trichloroethane was coated on the charge generation layer and dried at 120° C. for 30 minutes to form a charge transport layer in thickness of 18 μm. As a result, an electrophotographic member was obtained.

Electrophotographic properties of these electrophotographic members were measured in the same manner as described in Example 1 and listed in Table 6.

EXAMPLES 8 TO 10

Electrophotographic members were prepared in the same manner as described in Example 6 except for changing the mixing ratio of the benzidien derivative (1.2 parts) and Lexan 141 (1.8 parts) used in Example 6 as shown in Table 7.

Electrophotographic properties of these electrophotographic members were measured and listed in Table 7.

TABLE 7

| Example No. | Charge transport material | Mixing ratio* | $V_0$ (−V) | $V_K$ (%) | $E_{50}$ (lux · sec) | $V_R$ (−V) |
|---|---|---|---|---|---|---|
| 8 | [structure: benzidine derivative with CF₃ and OCH₃ substituents] | 0.9/2.1 | 985 | 83.2 | 1.2 | 0 |
| 9 | " | 1.2/1.8 | 990 | 82.8 | 1.0 | 0 |
| 10 | " | 1.5/1.5 | 980 | 79.6 | 1.0 | 0 |

Note)
*mixing ratio = charge transport material/polycarbonate (Lexan 141) (parts/parts)

COMPARATIVE EXAMPLES 2 TO 4

Electrophotographic members were prepared in the same manner as described in Examples 8 to 10 except for using the benzidine derivatives listed in Table 8 in place of the benzidine derivatives used in Examples 8 to 10.

Electrophotographic properties of the resulting electrophotographic members were measured and listed in Table 8.

TABLE 6

| Example No. | Charge transport material | $V_0$ (−V) | $V_K$ (%) | $E_{50}$ (lux · sec) | $V_R$ (−V) |
|---|---|---|---|---|---|
| 6 | [structure: benzidine derivative with CF₃ and OCH₃ substituents] | 990 | 82.8 | 1.0 | 0 |
| 7 | [structure: benzidine derivative with CF₃O and CH₃ substituents] | 1005 | 80.6 | 1.2 | 0 |

TABLE 8

| Comparative Example No. | Charge transport material | Mixing ratio* | $V_0$ (−V) | $V_K$ (%) | $E_{50}$ (lux·sec) | $V_R$ (−V) |
| --- | --- | --- | --- | --- | --- | --- |
| 2 | [structure: bis(3-methylphenyl-phenylamino)biphenyl] | 0.9/2.1 | 930 | 80.1 | 1.4 | 0 |
| 3 | " | 1.2/1.8 | 890 | 78.6 | 1.3 | 0 |
| 4 | " | 1.5/1.5 | 900 | 76.1 | 1.5 | 10 |

Note)
*mixing ratio = charge transport material/polycarbonate (Lexan 141) (parts/parts)

EXAMPLE 11 AND COMPARATIVE EXAMPLE 5

In order to measure changes of properties after repeated use of the electrophotographic members obtained in Example 9 and Comparative Example 3, these electrophotographic members were placed in a laser beam printer SL-2000 modified machine (mfd. by Hitachi, ltd.) and subjected to copying of 5000 sheets, followed by measurement of electrophotographic properties using the analyzer SP 428. Further, the resolution was also measured by copying a Test Chart No.=1-T provided by the Society of Electrophotography of Japan (1975 edition) at the initial time and after copying 5000 sheets.

The results are shown in Table 9.

EXAMPLES 12, 13 AND COMPARATIVE EXAMPLE 6

After forming a charge generation layer in the same manner as described in Example 1, a coating solution obtained by dissolving 1.2 parts of a benzidine derivative as listed in Table 10 and 1.8 parts of bisphenol Z type polycarbonate resin (Z-200, a trade name, mfd. by Mitsubishi Gas Chemical Co., Ltd.) in a mixed solvent of 9 parts of methylene chloride and 8 parts of 1,1,2-trichloroethane was coated thereon using an applicator. After drying at 120° C. for 30 minutes, an electrophotographic member having a charge transport layer in thickness of 18 μm was obtained.

In order to measure changes of properties after repeated use, the resulting electrophotographic members

TABLE 9

| Example No. | Charge transport material | Initial time | | | | | After copying 5,000 sheets | | | | |
| --- | --- | --- | --- | --- | --- | --- | --- | --- | --- | --- | --- |
| | | $V_0$ | $V_K$ | $E_{50}$ | $V_R$ | Resolution | $V_0$ | $V_K$ | $E_{50}$ | $V_R$ | Resolution |
| Example 11 | [structure: bis(3-CF$_3$-4-methoxyphenyl-phenylamino)biphenyl] | 990 | 82.8 | 1.0 | 0 | 16.0 | 985 | 81.7 | 1.0 | 0 | 16.0 |
| Comparative Example 5 | [structure: bis(3-methylphenyl-phenylamino)biphenyl] | 890 | 78.6 | 1.3 | 0 | 16.0 | 780 | 52.6 | 1.5 | 10 | 2.0 |

Note)
$V_0$ (−V), $V_K$ (%), $E_{50}$ (lux·sec), $V_R$ (−V), Resolution (lines/mm)
charge transport material/polycarbonate (Lexan 1414) = 1.2/1.8 (parts/parts)

were subjected to the same tests as in Example 11 and Comparative Example 5.

The results are shown in Table 10.

TABLE 10

| Example No. | Charge transport material | Initial time | | | | | After copying 5,000 sheets | | | | |
| --- | --- | --- | --- | --- | --- | --- | --- | --- | --- | --- | --- |
| | | $V_0$ | $V_K$ | $E_{50}$ | $V_R$ | Resolution | $V_0$ | $V_K$ | $E_{50}$ | $V_R$ | Resolution |
| Example 12 | [structure: bis(3-CF$_3$-phenyl-phenylamino)biphenyl] | 1010 | 79.2 | 1.2 | 0 | 16.0 | 995 | 79.1 | 1.2 | 0 | 16.0 |

TABLE 10-continued

| Example No. | Charge transport material | Initial time | | | | | After copying 5,000 sheets | | | | |
|---|---|---|---|---|---|---|---|---|---|---|---|
| | | $V_0$ | $V_K$ | $E_{50}$ | $V_R$ | Resolution | $V_0$ | $V_K$ | $E_{50}$ | $V_R$ | Resolution |
| Example 13 | (benzidine derivative with CF$_3$ and OCH$_3$ substituents) | 1025 | 83.4 | 1.0 | 0 | 16.0 | 1015 | 82.8 | 1.0 | 0 | 16.0 |
| Comparative Example 6 | (benzidine derivative with CH$_3$ substituents) | 1000 | 77.5 | 1.3 | 0 | 16.0 | 795 | 61.4 | 1.5 | 15 | 2.0 |

$V_0$ (−V), $V_K$ (%), $E_{50}$ (lux · sec), $V_R$ (−V), Resolution (lines/mm)
Charge transport material/polycarbonate (Z-200) = 1.2/1.8 (parts/parts)

EXAMPLES 14 TO 19

After forming a charge generation layer in the same manner as described in Example 1, a coating solution obtained by dissolving 1.2 parts of a benzidine derivative listed in Table 11 and 1.8 parts of bisphenol A type polycarbonate-resin (Lexan 141, mfd. by General Electric Co.) in a mixed solvent of 8.5 parts of methylene chloride and 8.5 parts of 1,2-dichloroethane was coated thereon using an applicator. After drying at 90° C. for 30 minutes, an electrophotographic member having a charge transport layer in thickness of 18 μm was obtained.

Electrophotographic properties of the resulting electrophotographic members were measured in the same manner as described in Example 1. Further, in order to measure changes of properties after repeated use, the same tests as in Example 11 and Comparative Example 5 were conducted.

The results are shown in Table 11.

TABLE 11

| Example No. | Charge transport material | Initial time | | | | | After copying 5,000 sheets | | | | |
|---|---|---|---|---|---|---|---|---|---|---|---|
| | | $V_0$ | $V_K$ | $E_{50}$ | $V_R$ | Resolution | $V_0$ | $V_K$ | $E_{50}$ | $V_R$ | Resolution |
| 14 | (benzidine derivative with CH$_3$ and OCH$_2$CF$_3$ substituents) | 1000 | 83.5 | 1.1 | 0 | 16.0 | 990 | 83.3 | 1.1 | 0 | 16.0 |
| 15 | (benzidine derivative with CH$_3$ and OCH$_2$CF$_3$ substituents) | 1005 | 83.8 | 0.9 | 0 | 12.5 | 1005 | 83.6 | 0.9 | 0 | 16.0 |
| 16 | (benzidine derivative with CH$_3$ and OCH$_2$CF$_3$ substituents) | 1100 | 84.1 | 0.9 | 0 | 16.0 | 1090 | 83.9 | 0.9 | 0 | 16.0 |
| 17 | (benzidine derivative with OCH$_2$CF$_3$ substituents) | 1005 | 84.1 | 0.9 | 0 | 16.0 | 995 | 83.9 | 0.9 | 0 | 16.0 |

TABLE 11-continued

| Example No. | Charge transport material | Initial time | | | | | After copying 5,000 sheets | | | | |
|---|---|---|---|---|---|---|---|---|---|---|---|
| | | $V_0$ | $V_K$ | $E_{50}$ | $V_R$ | Resolution | $V_0$ | $V_K$ | $E_{50}$ | $V_R$ | Resolution |
| 18 | 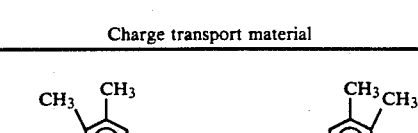 | 995 | 82.9 | 1.2 | 0 | 16.0 | 995 | 82.7 | 1.2 | 0 | 16.0 |
| 19 | 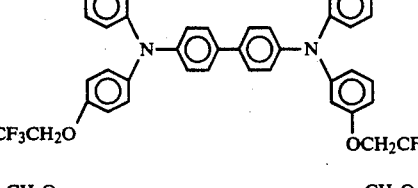 | 1020 | 83.3 | 0.9 | 0 | 12.5 | 1010 | 83.2 | 0.9 | 0 | 12.5 |

$V_0$ (—V), $V_K$ (%), $E_{50}$ (lux·sec), $V_R$ (—V), Resolution (lines/mm)
Charge transport material/polycarbonate (Lexan 141) = 1.2/1.8 (parts/parts)

EXAMPLE 20 AND COMPARATIVE EXAMPLE 7

After forming a charge generation layer in the same manner as described in Example 1, a coating solution obtained by dissolving 1.2 part of a benzidine derivative listed in Table 12 and 1.8 parts of saturated polyester resin (Vylon 290, a trade name, mfd. by Toyobo Co., Ltd.) in a mixed solvent of 8.5 parts of methylene chloride and 8.5 parts of 1,2-dichloroethane was coated thereon using an applicator. After drying at 90° C. for 30 minutes, an electrophotographic member having a charge transport layer in thickness of 18 μm was obtained.

In Comparative Example 7, since the benzidine derivative was precipitated at the time of forming a film of charge transport layer, no uniform (clear) coated film was obtained.

Electrophotographic properties of the resulting electrophotographic members were measured in the same manner as described in Example 1. Further, in order to measure changes of properties after repeated use, the same tests as in Example 11 and Comparative Example 5 were conducted.

The results are shown in Table 12.

TABLE 12

| Example No. | Charge transport material | Initial time | | | | | After copying 5,000 sheets | | | | |
|---|---|---|---|---|---|---|---|---|---|---|---|
| | | $V_0$ | $V_K$ | $E_{50}$ | $V_R$ | Resolution | $V_0$ | $V_K$ | $E_{50}$ | $V_R$ | Resolution |
| Example 20 | (structure with CH₃, CF₃CH₂O, OCH₂CF₃ groups) | 980 | 83.2 | 1.0 | 0 | 16.0 | 970 | 81.0 | 1.1 | 0 | 16.0 |
| Comparative Example 17 | (structure with CH₃ groups) | 865 | 76.4 | 1.4 | 15 | 8.0 | 645 | 48.9 | 2.4 | 50 | Not resolved. |

$V_0$ (−V),
$V_K$ (%),
$E_{50}$ (lux·sec),
$V_R$ (−V),
Resolution (lines/mm)
Charge transport material/polyester (Vylon 290) = 1.2/1.8 (parts/parts)

EXAMPLES 21 TO 24

A coating solution was prepared by dissolving 2.66 parts of alcohol-soluble polyamide resin (M 1276, a trade name, mfd. by Nihon Rilsan K.K.), 5.23 parts of melamine resin (ML 2000, a trade name, mfd. by Hitachi Chemical Co., Ltd., solid content 50%), and 0.28 part of trimellitic anhydride (mfd. by Wako Pure Chemical Industries, ltd.) in a mixed solvent of 62 parts of ethanol and 93 parts of 1,1,2-trichloroethane. The coating solution was coated on an aluminum plate (100 mm×100 mm and 0.1 mm thick) by a dipping method and dried at 140° C. for 30 minutes to form an undercoating layer in thickness of 0.3 μm.

Then, a mixture was prepared from 3.6 parts of τ-form non-metal phthalocyanine (mfd. by Toyo Ink Mfg. Co., Ltd.), 2.4 parts of polyvinyl acetal resin (KL-1, a trade name, mfd. by Sekisui Chemical Co., Ltd.), 35 parts of tetrahydrofuran and 35 parts of 1,2-dichloroethane. The mixture was kneaded in a ball mill having a hard glass made pot and zirconia balls (5 mm in diameter, mfd. by Nippon Kagaku Togyo Co., Ltd.) for 6 hours. To the resulting kneaded solution, 82 parts of tetrahydrofuran and 82 parts of 1,2-dichloroethane were added and dispersed by using ultrasonic wave for 8 hours. The resulting dispersion was coated on the undercoating layer by a dipping method and dried at 140° C. for 30 minutes to form a charge generation layer in thickness of 0.3 μm.

A coating solution was prepared by dissolving 8.4 parts of fluorine-containing N,N,N',N'-tetraarylbenzidine derivative as listed in Table 13 and 12.6 parts of tetraphenyl skeleton-containing polycarbonate TP-PC of the formula:

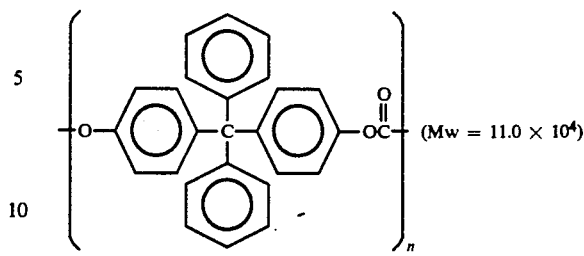

(mfd. by Idemitsu Kosan K.K.) in a mixed solvent of 65 parts of methylene chloride and 65 parts of 1,2-dichloroethane. The coating solution was coated on the charge generation layer by a dipping method, and dried at 90° C. for 30 minutes to form a charge transport layer in thickness of 18 μm. As a result, an electrophotographic plate was obtained.

Electrophotographic properties of the thus produced electrophotographic members were measured using a light decay measuring equipment (Cynthia 30, a trade name, mfd. by Midoriya Denki K.K.).

The results are shown in Table 13.

In Table 13, the dark decay (DDR5) means
a potential maintaining ratio from the potential ($V_5$) when allowed to stand in the dark for 5 seconds after charging at $-700$ V [($V_5/-700$)×100%].

The sensitivity means a exposure energy necessary for half decay of the surface potential ($-700$ V) after 0.2 second of light exposure, when irradiated with a monochromatic light of 780 nm in wavelength.

The residual potential ($V_R$) means a potential after 0.2 second of light exposure when exposed to pulse light of 780 nm in wavelength and having energy of 20 mJ/m² after charged at $-700$ V.

Further, in order to measure changes of properties after repeated use of the electrophotographic members, these members were placed in a laser beam printer SL 2000 modified machine (mfd. by Hitachi, Ltd.) and subjected to copying of 50,000 sheets, followed by measurement of charging potential ($V_0$), potential at exposed portion ($V_L$) and changing amounts of these potentials ($\Delta V_0$, $\Delta V_L$). Further, the resolution was also measured by copying a Test Chart No.=1−T provided by The Society of Electrophotography of Japan (1975 edition) at the initial time and after copying 50,000 sheets.

The results are shown in Table 13.

TABLE 13

| Example No. | Charge transport material | Electrophotographic properties* DDR5 (%) | Sensitivity (mJ/m²) | $V_R$ (−V) | Initial time** $V_0$ (−V) | $V_L$ (−V) | Resolution (lines/mm) | After copying 50,000 sheets** $V_0$ (−V) | $V_L$ (−V) | Resolution (lines/mm) | Changing amounts of potentials*** $\Delta V_0$ (V) | $\Delta V_0$ (V) |
|---|---|---|---|---|---|---|---|---|---|---|---|---|
| 21 | (structure with CH₃, CF₃CH₂O, CH₃, OCH₂CF₃ substituents) | 87.2 | 2.82 | 45 | 600 | 55 | 12.5 | 585 | 65 | 12.5 | −15 | +10 |
| 22 | (structure with CH₃, CF₃CH₂O, CH₃, OCH₂CF₃ substituents) | 86.3 | 2.88 | 50 | 595 | 60 | 16.0 | 585 | 65 | 16.0 | −10 | +5 |
| 23 | (structure with CF₃CH₂O, OCH₂CF₃ substituents) | 87.8 | 2.90 | 58 | 600 | 70 | 16.0 | 590 | 70 | 16.0 | −10 | 0 |
| 24 | (structure with CH₃O, CF₃CH₂O, OCH₃, OCH₂CF₃ substituents) | 87.1 | 2.92 | 46 | 600 | 55 | 12.5 | 575 | 70 | 12.5 | −25 | +15 |

Note)
*Measured results using Cynthia 30
**Measured results using SL 2000
***$\Delta V_0 = V_0$ (initial time) − $V_0$ (after copying 50,000 sheets)
$\Delta V_L = V_L$ (initial time) − $V_L$ (after copying 50,000 sheets)
(Measured results using SL 2000)
+: increase
−: decrease

COMPARATIVE EXAMPLE 8 AND 9

Electrophotographic members were produced in the same manner as described in Example 21 except for using the benzidine derivatives listed in Table 14 in place of the benzidine derivative used in Example 21.

Electrophotographic properties and changes of properties after repeated use of these electrophotographic members were measured in the same manner as described in Example 21.

The results are shown in Table 14.

coating the same dispersion as used in Example 21 except for using a mixture of saturated polyester resin (Vylon 290, a trade name, mfd. by Toyobo Co., Ltd.) and benzoguanamine resin (ML 351W, a trade name, mfd. by Hitachi Chemical Co., Ltd., solid content 60%) (solid content mixing ratio=9/1) in place of the polyvinyl acetal resin used in Example 21 as a binder by a dipping method and drying at 140° C. for 30 minutes.

Then, electrophotographic members were produced in the same manner as described in Example 21 using the benzidine derivatives shown in Table 15 in place of

TABLE 14

| Comparative Example No. | Charge transport material | Electrophotographic properties* | | | Initial time** | | |
|---|---|---|---|---|---|---|---|
| | | DDR5 (%) | Sensitivity (mJ/m$^2$) | $V_R$ (−V) | $V_0$ (−V) | $V_L$ (−V) | Resolution (lines/mm) |
| 8 | 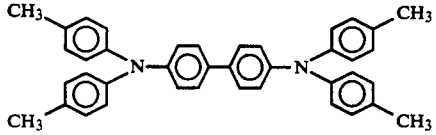 | 81.4 | 2.88 | 35 | 565 | 50 | 12.5 |
| 9 | 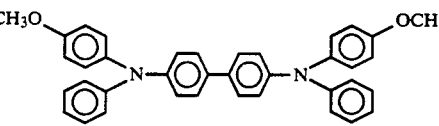 | 82.2 | 2.82 | 31 | 570 | 45 | 12.5 |

| Comparative Example No. | Charge transport material | After copying 50,000 sheets | | | Changing amounts of potentials* | |
|---|---|---|---|---|---|---|
| | | $V_0$ (−V) | $V_L$ (−V) | Resolution (lines/mm) | $\Delta V_0$ (V) | $\Delta V_0$ (V) |
| 8 | 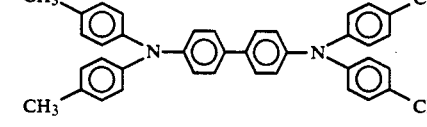 | 490 | 90 | 5.0 | −75 | +45 |
| 9 | 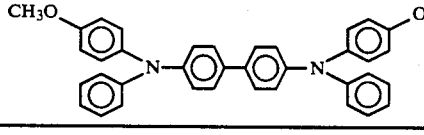 | 480 | 95 | 1.6 | −90 | +50 |

Note)
*, , *: See Table 13.

EXAMPLES 25 TO 27, COMPARATIVE EXAMPLES 10 AND 11

After forming an undercoating layer in the same manner as described in Example 21, a charge generation layer in thickness of 0.3 μm was formed thereon by the benzidine derivative used in Example 21.

Electrophotographic properties and changes of properties after repeated use of these electrophotographic members were measured in the same manner as described in Example 21.

The results are shown in Table 15.

TABLE 15

| Example No. | Charge transport material | Electrophotographic properties* | | | | Initial time** | | | After copying 50,000 sheets** | | | Changing amounts of potentials*** | |
|---|---|---|---|---|---|---|---|---|---|---|---|---|---|
| | | DDR5 (%) | Sensitivity (mJ/m²) | $V_R$ (−V) | $V_0$ (−V) | $V_L$ (−V) | Resolution (lines/mm) | | $V_0$ (−V) | $V_L$ (−V) | Resolution (lines/mm) | $\Delta V_0$ (V) | $\Delta V_0$ (V) |
| Example 25 | 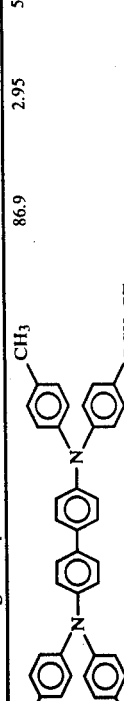 | 86.9 | 2.95 | 51 | 590 | 60 | 12.5 | | 575 | 75 | 16.0 | −15 | +15 |
| Example 26 | 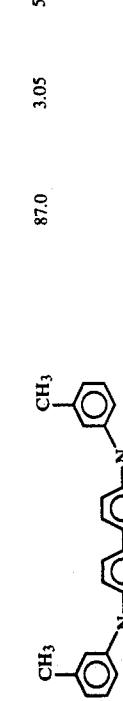 | 87.0 | 3.05 | 54 | 600 | 65 | 16.0 | | 590 | 75 | 16.0 | −10 | +10 |
| Example 27 | 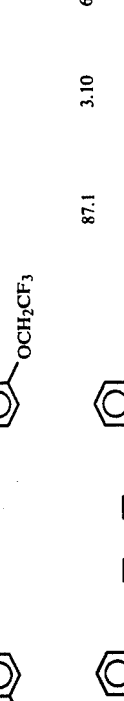 | 87.1 | 3.10 | 63 | 605 | 75 | 16.0 | | 590 | 80 | 16.0 | −15 | +5 |
| Comparative Example 10 | 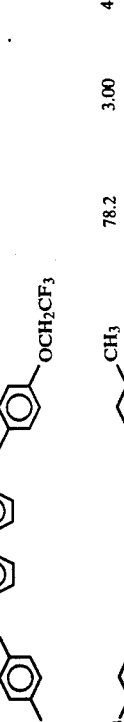 | 78.2 | 3.00 | 47 | 515 | 60 | 12.5 | | 430 | 110 | 4.0 | −85 | +50 |
| Comparative Example 11 | 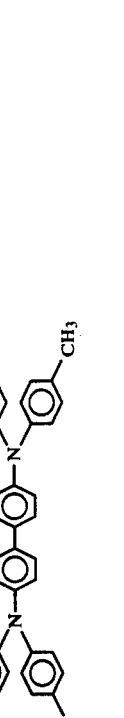 | 76.9 | 2.96 | 42 | 495 | 55 | 12.5 | | 390 | 115 | 1.6 | −105 | +60 |

Note)
*, , *: See Table 13

EXAMPLES 28 TO 30, COMPARATIVE EXAMPLES 12 AND 13

Figure 10:
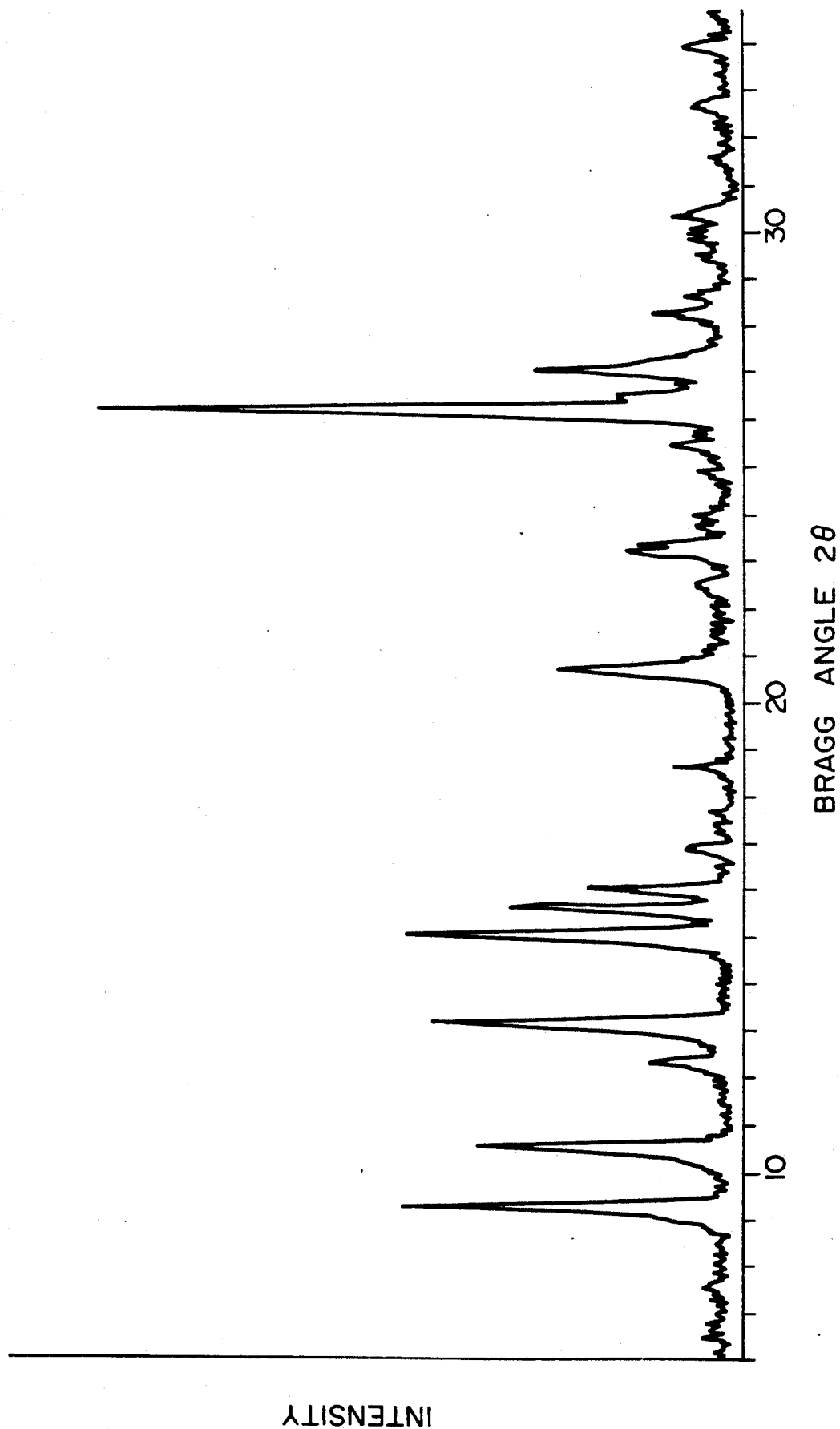
FIG. 10 is an X-ray diffraction pattern of β-form titanyl phthalocyanine used in Examples 28 to 30 and Comparative Examples 12 and 13.

After forming an undercoating layer in the same manner as described in Example 21, a charge generation layer in thickness of 0.2 μm was formed thereon by coating the same dispersion as used in Example 21 except for using β-form titanyl phthalocyanine having X-ray diffraction pattern as shown in FIG. 10 in place of the τ-form non-metal phthalocyanine used in Example 21 by a dipping method and drying at 140° C. for 30 minutes.

Then, electrophotographic members were produced in the same manner as described in Example 21 using the benzidine derivatives shown in Table 16 in place of the benzidine derivative used in Example 21.

Electrophotographic properties and changes of properties after repeated use of these electrophotographic members were measured in the same manner as described in Example 21.

The results are shown in Table 16.

TABLE 16

| Example No. | Charge transport material | Electrophotographic properties* | | | | Initial time** | | | After copying 50,000 sheets** | | | | Changing amounts of potentials*** | |
|---|---|---|---|---|---|---|---|---|---|---|---|---|---|---|
| | | DDR5 (%) | Sensitivity (mJ/m²) | $V_R$ (−V) | | $V_0$ (−V) | $V_L$ (−V) | Resolution (lines/mm) | $V_0$ (−V) | $V_L$ (−V) | Resolution (lines/mm) | | $\Delta V_0$ (V) | $\Delta V_L$ (V) |
| Example 28 | [structure with CH₃, OCH₂CF₃, CF₃CH₂O] | 92.9 | 2.70 | 22 | | 635 | 30 | 16.0 | 620 | 40 | 16.0 | | −15 | +10 |
| Example 29 | [structure with CH₃, OCH₂CF₃, CF₃CH₂O] | 93.0 | 2.79 | 27 | | 640 | 35 | 16.0 | 630 | 40 | 16.0 | | −10 | +5 |
| Example 30 | [structure with OCH₂CF₃, CF₃CH₂O] | 92.8 | 2.84 | 27 | | 615 | 40 | 16.0 | 625 | 40 | 16.0 | | −10 | 0 |
| Comparative Example 12 | [structure with CH₃, CH₃] | 87.8 | 2.94 | 20 | | 600 | 30 | 12.5 | 535 | 70 | 5.0 | | −65 | +40 |
| Comparative Example 13 | [structure with OCH₃, CH₃O] | 87.1 | 2.90 | 21 | | 595 | 30 | 12.5 | 510 | 80 | 1.6 | | −85 | +50 |

Note)
*, , *: See Table 13

EXAMPLES 31, 32, COMPARATIVE EXAMPLE 14

Figure 11:
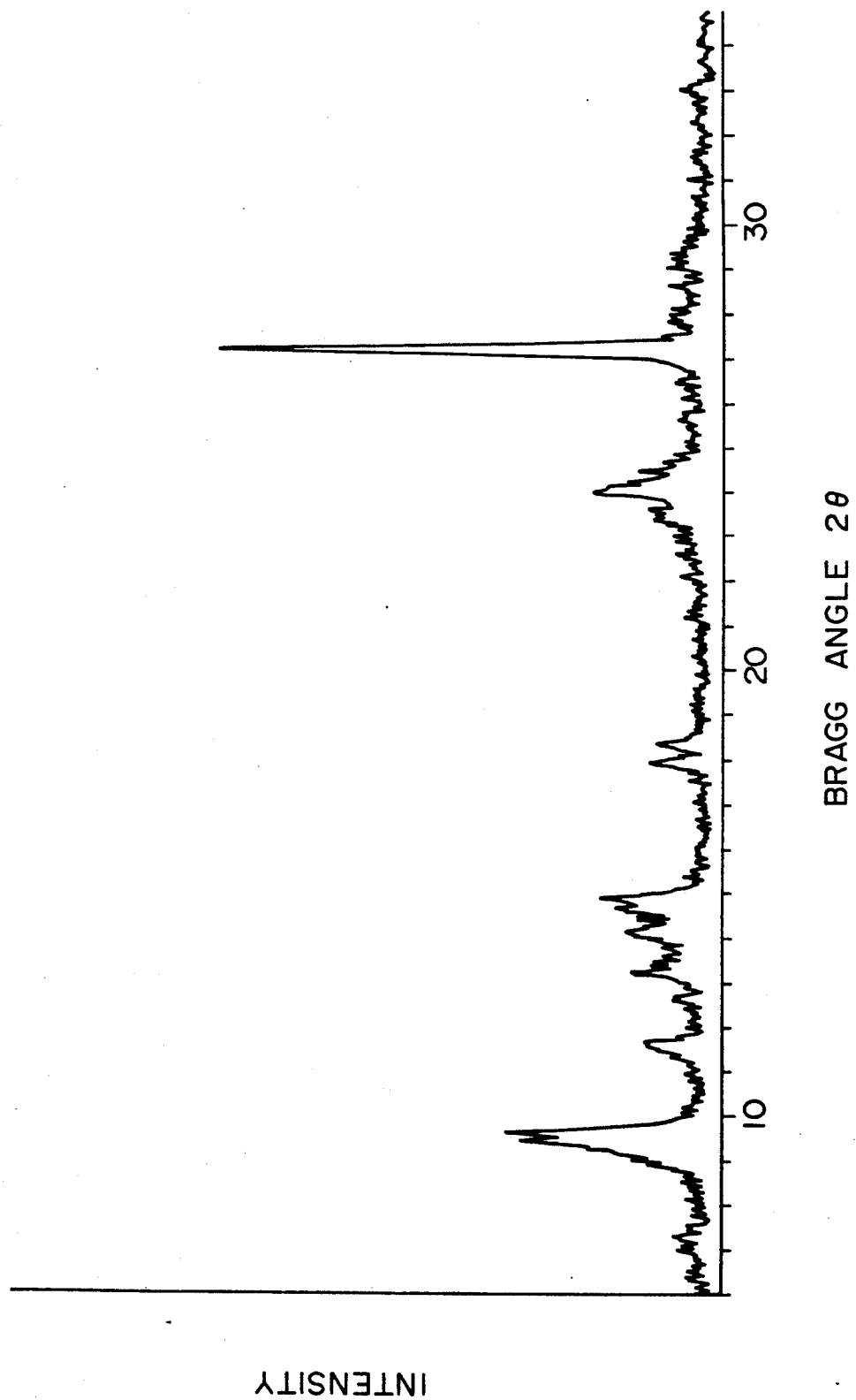
FIG. 11 is an X-ray diffraction pattern of titanyl phthalocyanine used in Examples 31 and 32, and Comparative Example 14.

After forming an undercoating layer in the same manner as described in Example 21, a charge generation layer in thickness of 0.2 μm was formed thereon by coating the same dispersion as used in Example 21 except for using titanyl phthalocyanine having X-ray diffraction pattern as shown in FIG. 11 in place of the τ-form non-metal phthalocyanine used in Example 21 by a dipping method and drying at 140° C. for 30 minutes.

Then, electrophotographic members were produced in the same manner as described in Example 21 using the benzidine derivatives shown in Table 17 in place of the benzidine derivative used in Example 21.

Electrophotographic properties and changes of properties after repeated use of these electrophotographic members were measured in the same manner as described in Example 21.

The results are shown in Table 17.

TABLE 17

| Example No. | Charge transport material | Electrophotographic properties* | | | Initial time** | | | After copying 50,000 sheets** | | | Changing amounts of potentials*** | |
|---|---|---|---|---|---|---|---|---|---|---|---|---|
| | | DDR5 (%) | Sensitivity (mJ/m$^2$) | $V_R$ (−V) | $V_0$ (−V) | $V_L$ (−V) | Resolution (lines/mm) | $V_0$ (−V) | $V_L$ (−V) | Resolution (lines/mm) | $\Delta V_0$ (V) | $\Delta V_L$ (V) |
| Example 31 | [structure with CH$_3$, OCH$_2$CF$_3$, CF$_3$CH$_2$O groups] | 88.7 | 2.69 | 42 | 615 | 50 | 16.0 | 600 | 60 | 16.0 | −15 | +10 |
| Example 32 | [structure with OCH$_2$CF$_3$, CF$_3$CH$_2$O groups] | 89.1 | 2.73 | 47 | 620 | 55 | 16.0 | 605 | 60 | 16.0 | −15 | +5 |
| Comparative Example 14 | [structure with OCH$_3$, CH$_3$O groups] | 84.0 | 2.82 | 35 | 575 | 45 | 16.0 | 515 | 85 | 2.0 | −60 | +40 |

Note)
*, , *: See Table 13.

EXAMPLES 33, 34, COMPARATIVE EXAMPLE 15

Electrophotographic members were produced in the same manner as described in Example 28 except for using the benzidine derivatives as listed in Table 18 and the mixing ratios with the tetraphenyl skeleton-containing polycarbonate TP-Pc as listed in Table 18 in place of the benzidine derivative (8.4 parts) and the tetraphenyl skeleton-containing polycarbonate TP-Pc (12.6 parts) used in Example 28.

Electrophotographic properties and changes of properties after repeated use of these electrophotographic members were measured in the same manner as described in Example 21.

The results are shown in Table 18.

TABLE 18

| | | Electrophotographic properties** | | | Initial time*** | | | After copying 50,000 sheets*** | | | Changing amounts of potentials**** | |
|---|---|---|---|---|---|---|---|---|---|---|---|---|
| Example No. | Charge transport material | Mixing ratio* | DDR5 (%) | Sensitivity (mJ/m²) | $V_R$ (−V) | $V_0$ (−V) | $V_L$ (−V) | Resolution (lines/mm) | $V_0$ (−V) | $V_L$ (−V) | Resolution (lines/mm) | $\Delta V_0$ (V) | $\Delta V_L$ (V) |
| Example 33 | (structure) | 9.45/11.55 | 92.7 | 2.64 | 16 | 630 | 30 | 16.0 | 615 | 40 | 16.0 | −15 | +10 |
| Example 34 | (structure) | 10.5/10.5 | 93.4 | 2.75 | 10 | 635 | 25 | 16.0 | 615 | 30 | 16.0 | −20 | +5 |
| Comparative Example 35 | (structure) | 10.5/10.5 | 86.8 | 2.89 | 10 | 595 | 25 | 10.0 | 505 | 80 | 1.6 | −90 | +55 |

Note)
*: mixing ratio = charge transport material/TP—Pc (parts/parts)
, *, ****: See Table 13.

EXAMPLES 35 TO 37, COMPARATIVE EXAMPLE 16

After forming an undercoating layer in the same manner as described in Example 21, a charge transport layer in thickness of 18 μm was formed by coating thereon a coating solution obtained by dissolving 10.5 parts of a benzidine derivative as listed in Table 19 and 10.5 parts of polyester carbonate resin (APE-50, a trade name, mfd. by Bayer Japan Ltd.) in a mixed solvent of 65 parts of methylene chloride and 65 parts of 1,2-dichloromethane by a dipping method and dried at 90° C. for 30 minutes.

Electrophotographic properties and changes of properties after repeated use of these electrophotographic members were measured in the same manner as described in Example 21.

The results are shown in Table 19.

TABLE 19

| Example No. | Charge transport material | Electrophotographic properties* DDR5 (%) | Sensitivity (mJ/m²) | $V_R$ (−V) | Initial time** $V_0$ (−V) | $V_L$ (−V) | Resolution (lines/mm) | After copying 50,000 sheets** $V_0$ (−V) | $V_L$ (−V) | Resolution (lines/mm) | Changing amounts of potentials*** $\Delta V_0$ (V) | $\Delta V_L$ (V) |
|---|---|---|---|---|---|---|---|---|---|---|---|---|
| Example 35 | | 87.9 | 3.19 | 47 | 600 | 60 | 12.5 | 580 | 75 | 12.5 | −20 | +15 |
| Example 36 | | 87.1 | 3.29 | 52 | 595 | 65 | 16.0 | 580 | 75 | 16.0 | −15 | +10 |
| Example 37 | | 88.1 | 3.30 | 60 | 600 | 70 | 16.0 | 585 | 75 | 16.0 | −15 | +5 |
| Comparative Example 16 | | 83.2 | 3.18 | 35 | 575 | 45 | 16.0 | 500 | 90 | 2.0 | −75 | +45 |

Note) *, , *: See Table 13.

EXAMPLES 38 TO 40, COMPARATIVE EXAMPLE 17

After forming an undercoating layer in the same manner as described in Example 21, a charge transport layer in thickness of 18 μm was formed by coating thereon a coating solution obtained by dissolving 10.5 parts of a benzidine derivative as listed in Table 20 and 10.5 parts of bisphenol A type polycarbonate resin (Panlight C-1400, a trade name, mfd. by Teijin Ltd.) in a mixed solvent of 65 parts of methylene chloride and 65 parts of 1,2-dichloromethane by a dipping method and dried at 90° C. for 30 minutes.

Electrophotographic properties and changes of properties after repeated use of these electrophotographic members were measured in the same manner as described in Example 21.

The results are shown in Table 20.

TABLE 20

| Example No. | Charge transport material | Electrophotographic properties* | | | Initial time** | | | After copying 50,000 sheets** | | | Changing amounts of potentials*** | |
|---|---|---|---|---|---|---|---|---|---|---|---|---|
| | | DDR5 (%) | Sensitivity (mJ/m²) | $V_R$ (-V) | $V_0$ (-V) | $V_L$ (-V) | Resolution (lines/mm) | $V_0$ (-V) | $V_L$ (-V) | Resolution (lines/mm) | $\Delta V_0$ (V) | $\Delta V_L$ (V) |
| Example 38 | [structure with CH₃, OCH₂CF₃, CF₃CH₂O] | 87.4 | 3.21 | 55 | 595 | 70 | 12.5 | 575 | 90 | 12.5 | −20 | +20 |
| Example 39 | [structure with CH₃, OCH₂CF₃, CF₃CH₂O, CH₃] | 86.8 | 3.32 | 63 | 590 | 75 | 16.0 | 575 | 90 | 16.0 | −15 | +15 |
| Example 40 | [structure with OCH₂CF₃, CF₃CH₂O] | 87.8 | 3.35 | 74 | 595 | 85 | 16.0 | 580 | 95 | 16.0 | −15 | +10 |
| Comparative Example 17 | [structure with OCH₃, CH₃O] | 83.4 | 3.22 | 40 | 570 | 50 | 16.0 | 490 | 115 | 1.6 | −80 | +65 |

Note)
*, , *: See Table 13.

SYNTHESIS EXAMPLE 10

Synthesis of
N,N'-bis(3-trifluoromethylphenyl)N,N'-bis(4-methoxyphenyl)-(1,1'-biphenyl)-4,4'-diamine (Compound (I-4) and used in Example 4)

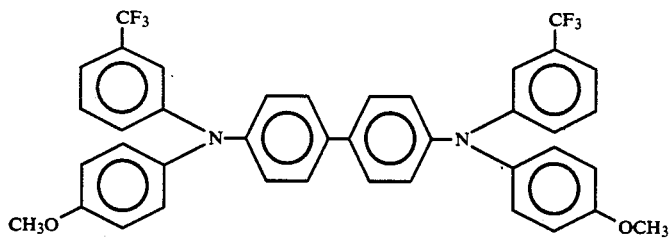

(1) Synthesis of m-trifluoromethylacetanilide

In a 1-liter round bottom glass flask equipped with a thermometer, a condenser and a stirrer, 161.1 g (1 mole) of m-aminobenzotrifluoride and 220 ml of glacial acetic acid were placed and heated to 70° C. Then, 105 ml (1.1 moles) of acetic anhydride was added dropwise to the reaction solution for 2 hours and maintained for additional 1 hour.

After the reaction, the contents were concentrated under reduced pressure and dried to give m-trifluoromethylacetanilide having a melting point of 103.6° C. in an amount of 201.1 g (yield 99%).

(2) Synthesis of N-(3-trifluoromethylphenyl)-p-anisidine

In a 500-ml round bottom glass flask equipped with a thermometer, a condenser and a stirrer, 101.6 g (0.5 mole) of m-trifluoromethylacetanilide, 175.5 g (0.75 mole) of p-methoxyiodobenzene, 103.8 g (0.75 mole) of potassium carbonate and 15 g of a copper powder were placed and heated to 180° C. gradually for 3 hours, followed by gradual temperature rise to 195° C. for 40 hours.

After cooling the contents to 90° C., 100 ml of dimethylsulfoxide and 200 ml of a 40% aqueous solution of potassium hydroxide were added thereto, followed by gradual temperature rise to 80° C. for 2 hours, and gradual temperature rise to 95° C. for 4 hours.

After the reaction, the contents were cooled and poured into 500 ml of toluene, and stirred for 30 minutes. After filtering a solid material, the toluene layer was washed with a 10% aqueous solution of sodium sulfate and water.

After removing the toluene by evaporation under reduced pressure and recovery of a fraction of 145° C./4 Torr by vacuum distillation, the desired N-(3-trifluoromethylphenyl)-p-anisidine having a melting point of 55.5° C. in an amount of 88.2 g (yield 66%).

(3) Synthesis of Compound (I-4)

In a 300-ml round bottom glass flask equipped with a thermometer, a condenser attaching a water separator and a stirrer, 40.6 g (0.1 mole) of 4,4'-diiodobiphenyl in purity of 98.6%, 80.1 g (0.3 mole) of N-3-trifluoromethylphenyl-p-anisidine in purity of 99.6%, 20.7 g of potassium carbonate and 8 g of a copper powder were placed and maintained at a reaction temperature of 190° to 200° C. for 23 hours. The water produced during the reaction was taken out of the reaction system by the water separator.

After the reaction, the contents were diluted with 350 ml of toluene and filtered to remove insoluble materials. The resulting toluene solution was concentrated under reduced pressure to yield a brown oily material.

Then, n-hexane was poured into the brown oily material. After filtering deposited crystalline material, the filtrate was treated with active carbon in a solvent of ethyl acetate, followed by concentration under reduced pressure.

The concentrated material was purified by column chromatography (alumina/toluene), followed by recrystallization from cyclohexane to give white crystals of N,N'-bis(3-trifluoromethylphenyl)-N,N'-bis(4-methoxyphenyl)-[1,1'-biphenyl]-4,4'-diamine in purity of 99.8% having a melting point of 133.7° C. in an amount of 34.7 g (yield 51.2%).

Elementary analysis (for $C_{40}H_{30}F_6N_2O_2$).

|  | C (%) | H (%) | F (%) | N (%) |
|---|---|---|---|---|
| Calcd. | 70.17 | 4.42 | 16.65 | 4.09 |
| Found | 70.30 | 4.48 | 16.50 | 4.17 |

SYNTHESIS EXAMPLE 11

Synthesis of
N,N'-bis(4-methylphenyl)-N,N'-bis[4-(2,2,2-trifluoroethoxyphenyl)]-[1,1'-biphenyl] -4,4'-diamine (Compound (I-36) used in Example 15)

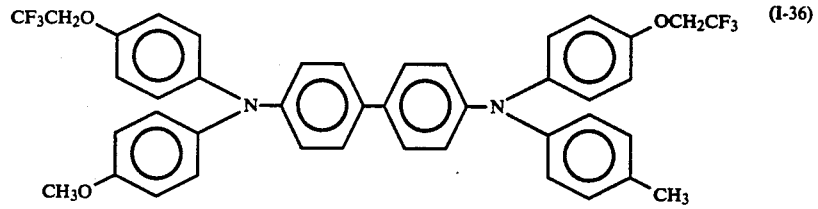

In a 300-ml round bottom glass flask equipped with a thermometer, a condenser attaching a water separator and a stirrer, 100 moles of 4,4'-diiodobiphenyl in purity of 99.0%, 260 mmoles of N-4-(2,2,2-trifluoroethoxyphenyl)-p-toluidine in purity of 99.8%, 20.7 g of potassium carbonate, and 8 g of a copper powder were placed and maintained at 220° to 240° C. for 8 hours. The water produced during the reaction was taken out of the reaction system by the water separator.

After the reaction, the contents were diluted with 350 ml of toluene and filtered to remove insoluble materials. The resulting toluene solution was concentrated under reduced pressure to give a brown oily material.

The brown oily material was purified by column chromatography (alumina/cyclohexane), subjected to treatment with active carbon in an ethanol solvent and recrystallized to give white crystals of N,N'-bis(4-methylphenyl)-N,N'-bis[4-(2,2,2-trifluoroethoxyphenyl)] -[1,1'-biphenyl]-4,4'-diamine in purity of 99.4% having a melting point of 102° to 103° C. in an amount of 33.5 g (yield 46.8%).

Elementary analysis (for $C_{42}H_{34}F_6N_2O_2$).

|  | C (%) | H (%) | F (%) | N (%) |
|---|---|---|---|---|
| Calcd. | 70.78 | 4.81 | 15.99 | 3.93 |
| Found | 70.86 | 4.75 | 16.68 | 3.88 | ment with active carbon, and recrystallized from ethanol to give white crystals of N,N'-bis(3-methylphenyl)-N,N'-bis[4-(2,2,2-trifluoroethoxyphenyl)]-[1,1'-biphenyl]-4,4'-diamine in purity of 98.8% and having a melting point of 88.2° C. in an amount of 31.7 g (yield 43.9%). Elementary analysis (for $C_{42}H_{34}F_6N_2O_2$).

|  | C (%) | H (%) | F (%) | N (%) |
|---|---|---|---|---|
| Calcd. | 70.78 | 4.81 | 15.99 | 3.93 |
| Found | 71.11 | 4.80 | 17.12 | 3.78 |

Figure 13:
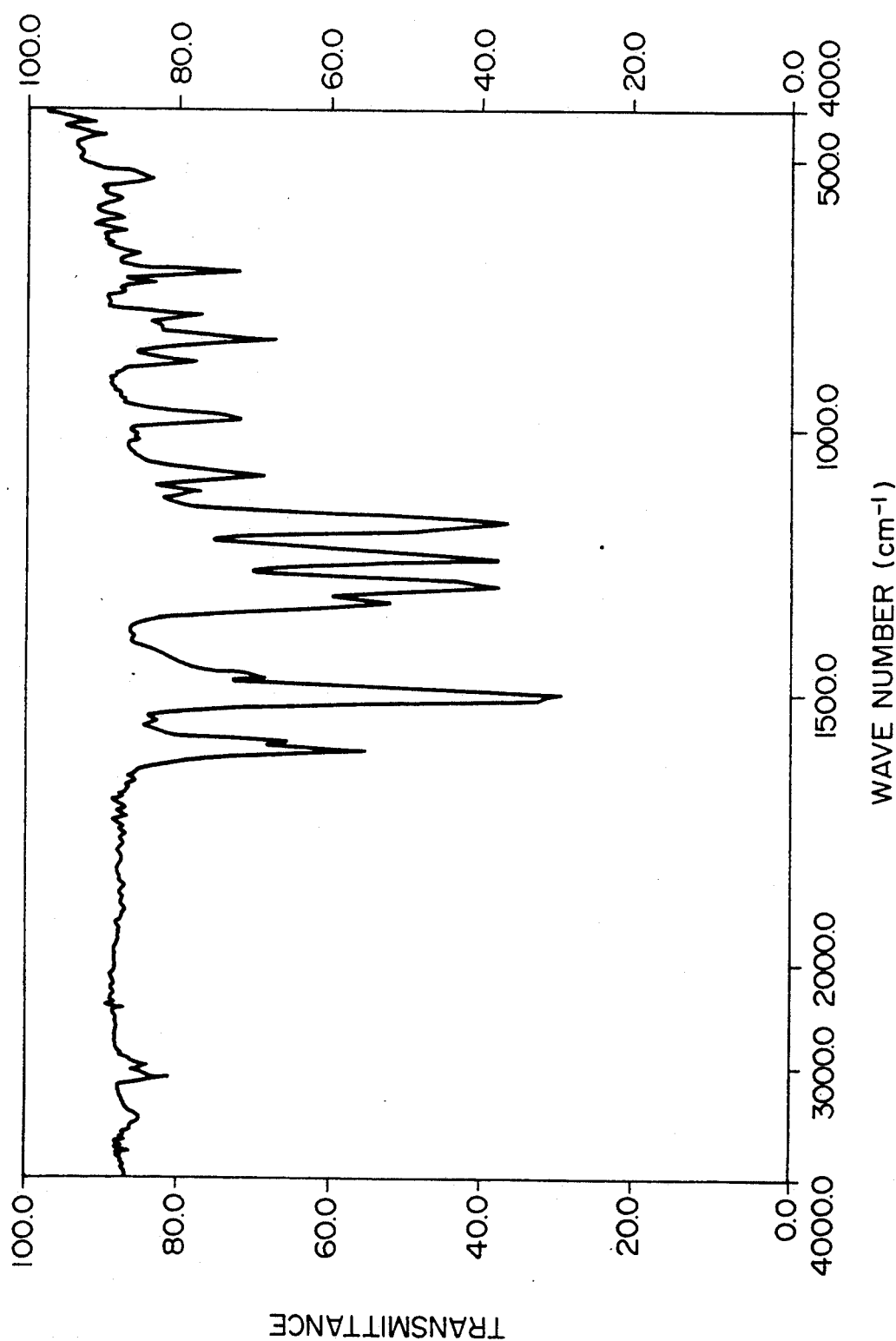

FIG. 13 shows infrared absorption spectrum of N,N'-bis(3-methylphenyl)-N,N'-bis[4-(2,2,2-trifluoroethoxyphenyl)]-[1,1'-biphenyl]-4,4'-diamine.

SYNTHESIS EXAMPLE 13

Synthesis of N,N'-diphenyl-N,N'-bis[4-(2,2,2-trifluoroethoxyphenyl)][1,1'-biphenyl]-4,4'-diamine (Compound (I-56) and used in Example 17)

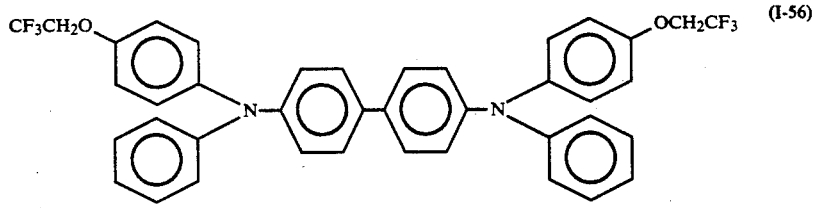

Figure 12:
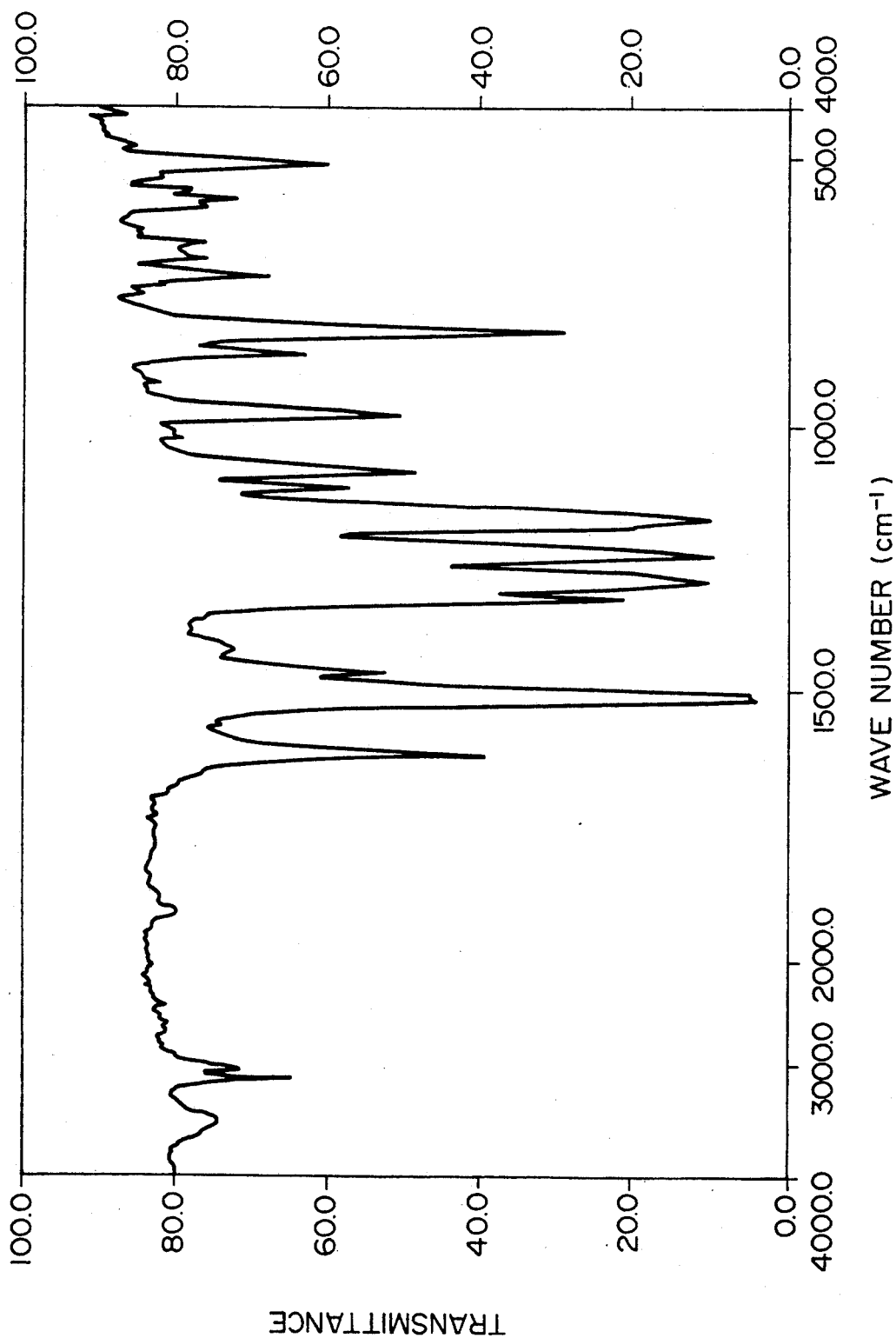

FIG. 12 shows infrared absorption spectrum of N,N'-bis(4-methylphenyl)-N,N'-bis[4-(2,2,2-trifluoroethoxyphenyl)]-[1,1'-biphenyl]-4,4'-diamine.

SYNTHESIS EXAMPLE 12

Synthesis of N,N'-bis(3-methylphenyl)-N,N-bis[4-(2,2,2-trifluoroethoxyphenyl)]-[1,1'-biphenyl]-4,4'-diamine (Compound (I-37) and used in Example 16)

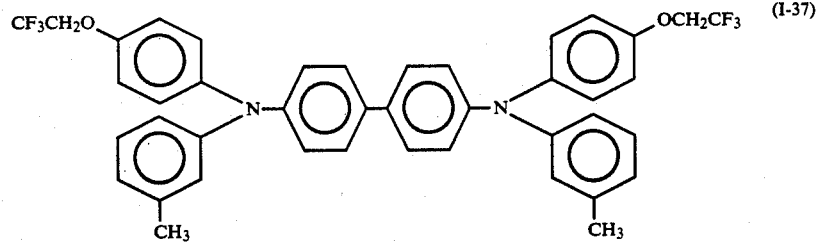

In a 300-ml round bottom glass flask equipped with a thermometer, a condenser attaching a water separator and a stirrer, 100 mmoles of 4,4'-diiodobiphenyl in purity of 99.0%, 260 mmoles of N-4-(2,2,2-trifluoroethoxyphenyl)-m-toluidine in purity of 99.4%, 20.7 g of potassium carbonate and 8 g of a copper powder were placed and maintained at 210° to 230° C. for 12 hours. The water produced during the reaction was taken out of the reaction system by the water separator.

After the reaction, the contents were diluted with 350 ml of toluene and filtered to remove insoluble materials. The resulting toluene solution was concentrated under reduced pressure to give a brown oily material.

The brown oily material was purified by column chromatography (alumina/toluene), subjected to treat- In a 300-ml round bottom glass flask equipped with a thermometer, a condenser attaching a water separator and a stirrer, 100 mmoles of 4,4'-diiodobiphenyl in purity of 99.0%, 260 mmoles of N-4-(2,2,2-trifluoroethoxyphenyl)-aniline in purity of 99.7%, 20.7 g of potassium carbonate, and 8 g of a copper powder were placed and maintained at 210° to 230° C. for 10 hours. The water produced during the reaction was taken out of the reaction system by the water separator.

After the reaction, the contents were diluted with 350 ml of toluene and filtered to remove insoluble materials. The resulting toluene solution was concentrated under reduced pressure to give a brown oily material.

The brown oily material was recrystallized from a mixed solvent of methanol-ethyl acetate to give yellow crystalline material, which was purified by column chromatography (alumina/toluene), subjected to treatment with active carbon in a cyclohexane solvent and finally recrystallized from ethanol-ethyl acetate to give white crystals of N,N'-diphenyl-N,N'-bis[4-(2,2,2-trifluoroethoxyphenyl)]-[1,1'-biphenyl]-4,4'-diamine · in purity of 99.6% and having a melting point of 130.2° C. in an amount of 54.5 g (yield 80.1%).

Elementary analysis (for $C_{40}H_{30}F_6N_2O_2$).

|  | C (%) | H (%) | F (%) | N (%) |
|---|---|---|---|---|
| Calcd. | 70.17 | 4.42 | 16.65 | 4.09 |
| Found | 70.12 | 4.58 | 17.80 | 3.98 |

Figure 14:
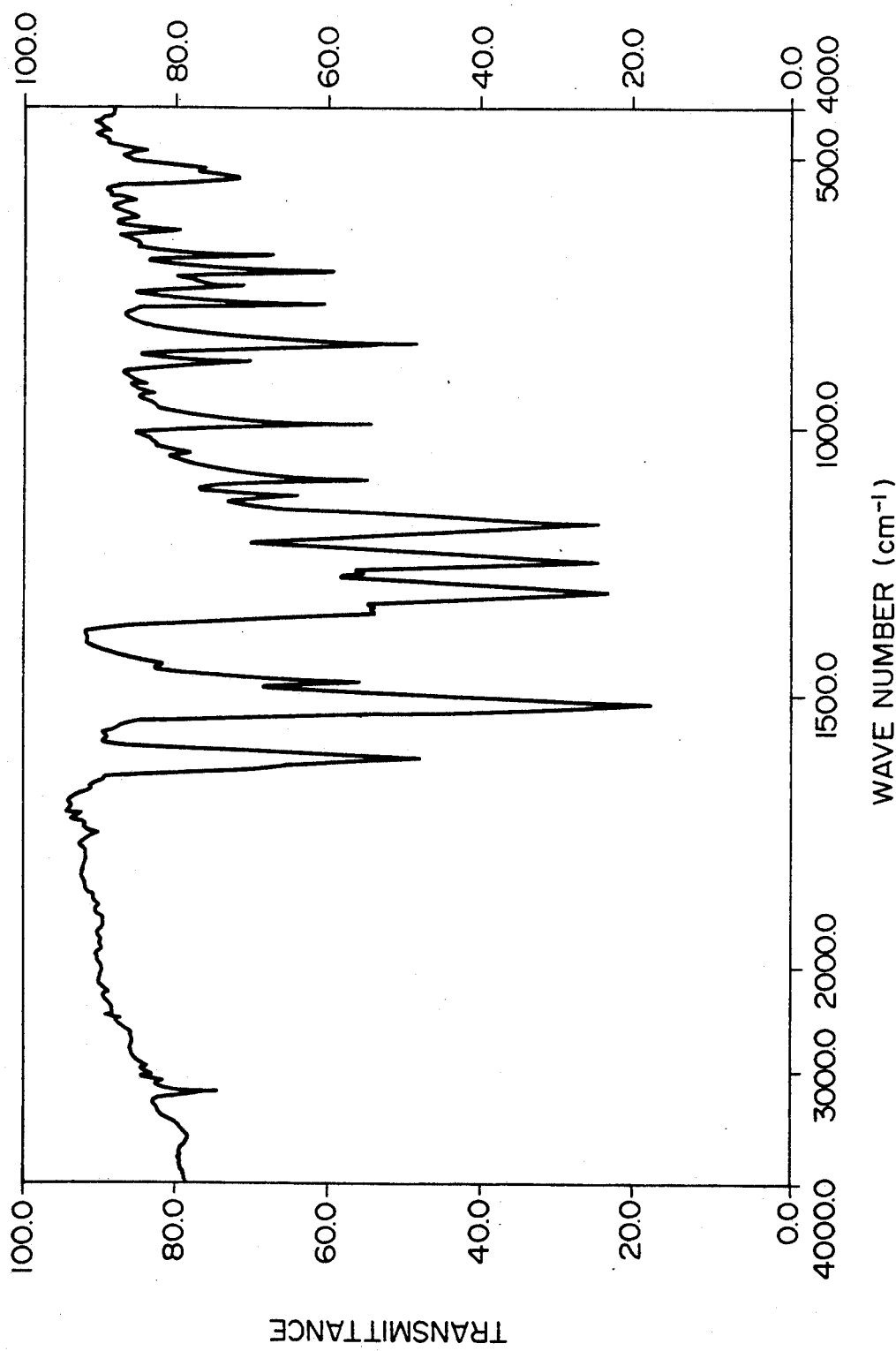

FIG. 14 shows infrared absorption spectrum of N,N'-diphenyl-N,N'-bis[4-(2,2,2-trifluoroethoxyphenyl)]-[1,1'-biphenyl]-4,4'-diamine

SYNTHESIS EXAMPLE 14
Synthesis of N,N'-bis(4-methoxyphenyl)-N,N'-bis[4-(2,2,2-trifluoroethoxyphenyl)]-[1,1'-biphenyl]-4,4'-diamine (Compound (I-38) used in Example 19)

SYNTHESIS EXAMPLE 15
Synthesis of N,N'-bis(1,1'-biphenyl)-N,N'-bis[4-(2,2,2-trifluoroethoxyphenyl)]-[1,1'-biphenyl]-4,4'-diamine (Compound (I-57))

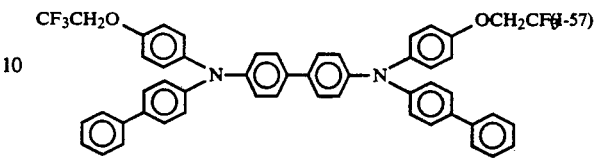

In a 300-ml round bottom glass flask equipped with a thermometer, a condenser attaching a water separator

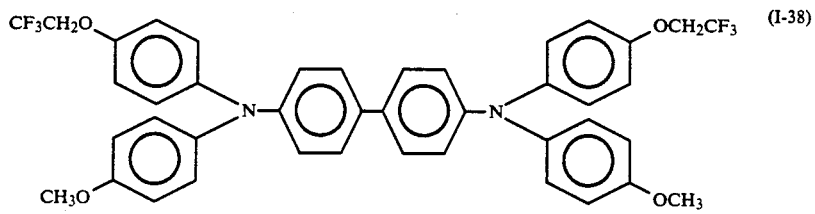

In a 300-ml round bottom glass flask equipped with a thermometer, a condenser attaching a water separator and a stirrer, 100 mmoles of 4,4'-diiodobiphenyl in purity of 99.0%, 260 mmoles of N-4-(2,2,2-trifluoroethoxyphenyl)-p-anisidine in purity of 99.0%, 20.7 g of potassium carbonate, and 8 g of a copper powder were placed and maintained at 220° to 240° C. for 8 hours. The water produced during the reaction was taken out of the reaction system by the water separator.

After the reaction, the contents were diluted with 350 ml of toluene and filtered to remove insoluble materials. The resulting toluene solution was concentrated under reduced pressure to give a brown oily material.

The brown oily material was purified by column chromatography (alumina/toluene), and recrystallized to give white crystals of N,N'-bis(4-methoxyphenyl)-N,N'-bis[4-(2,2,2-trifluoroethoxyphenyl)]-[1,1'-biphenyl]-4,4'-diamine in purity of 99.6% having a melting point of 133.1° C. in an amount of 35.5 g (yield 47.7%).

Elementary analysis (for $C_{42}H_{34}F_6N_2O_4$).

|  | C (%) | H (%) | F (%) | N (%) |
|---|---|---|---|---|
| Calcd. | 67.74 | 4.60 | 15.31 | 3.76 |
| Found | 67.82 | 4.57 | 14.93 | 3.63 |

Figure 15:
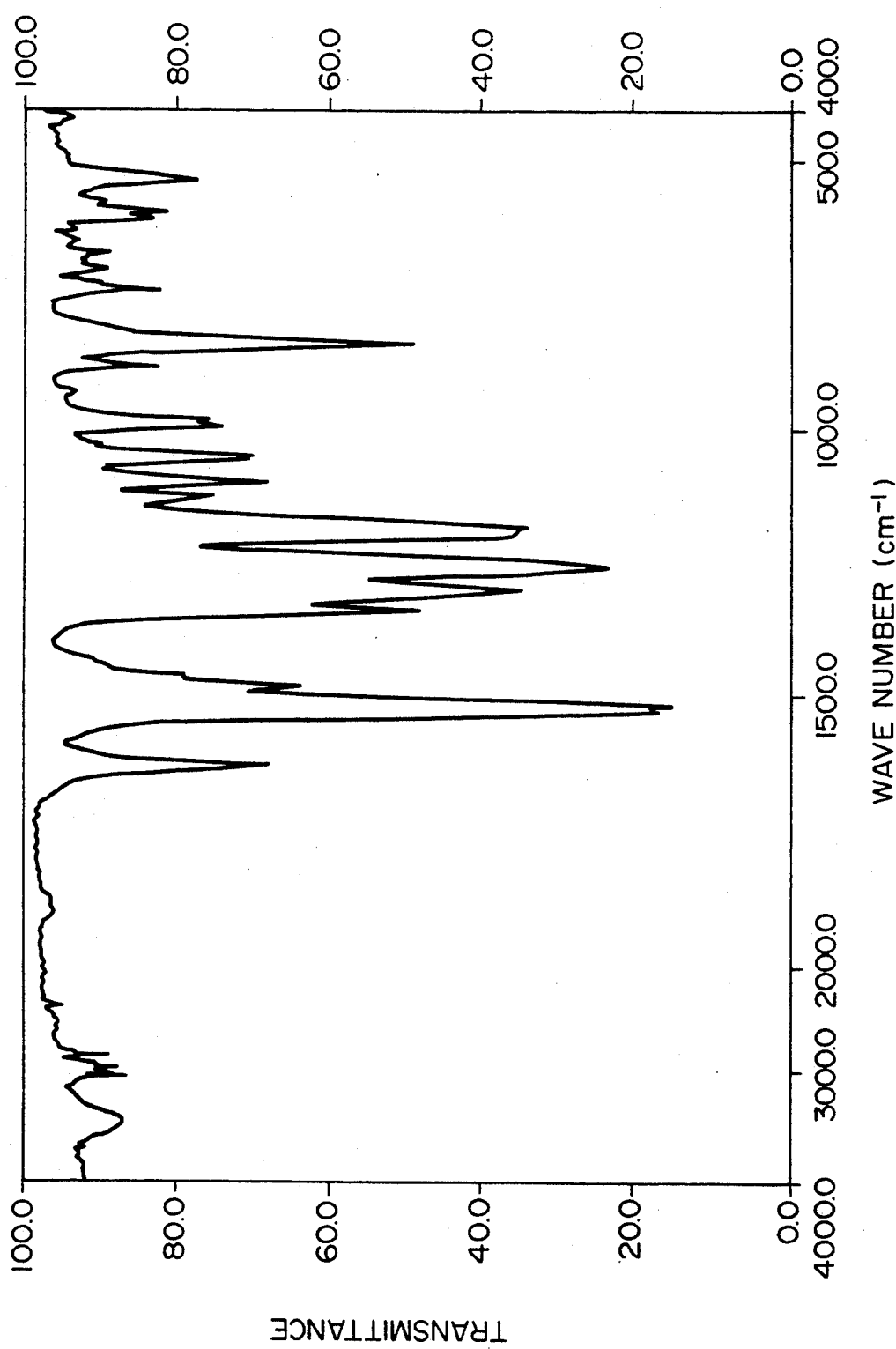

FIG. 15 shows infrared adsorption spectrum of N,N'-bis(4-methoxyphenyl)-N,N'-bis[4-(2,2,2-trifluoroethoxyphenyl)]-[1,1'-biphenyl]-4,4'-diamine.

and a stirrer, 100 mmoles of 4,4'-diiodobiphenyl in purity of 99.0%, 260 mmoles of N-4-(2,2,2-trifluoroethoxyphenyl-4-phenylaniline in purity of 99.6%, 20.7 9 of potassium carbonate and 8 g of a copper powder were placed and maintained at 200° to 210° C. for hours. The water produced during the reaction was taken out of the reaction system by the water separator.

After the reaction, the contents were diluted with 350 ml of toluene and filtered to remove insoluble materials. The resulting toluene solution was concentrated under reduced pressure to give a brown oily material.

The brown oily material was subjected to treatment with active carbon in a ethyl acetate solvent, and purified by column chromatography (alumina/toluene), and recrystallized from toluene to give white crystals of N,N'-bis(1,1'-biphenyl)-N,N'-bis[4-(2,2,2-trifluoroethoxyphenyl)]-[1,1'-biphenyl]-4,4'-diamine in purity of 99.5% and having a melting point of 242.7° C. in an amount of 51.2 g (yield 61.2%).

Elementary analysis (for $C_{52}H_{38}F_6N_2O_2$).

|  | C (%) | H (%) | F (%) | N (%) |
|---|---|---|---|---|
| Calcd. | 74.63 | 4.58 | 13.62 | 3.35 |
| Found | 74.22 | 4.55 | 14.16 | 3.24 |

Figure 16:
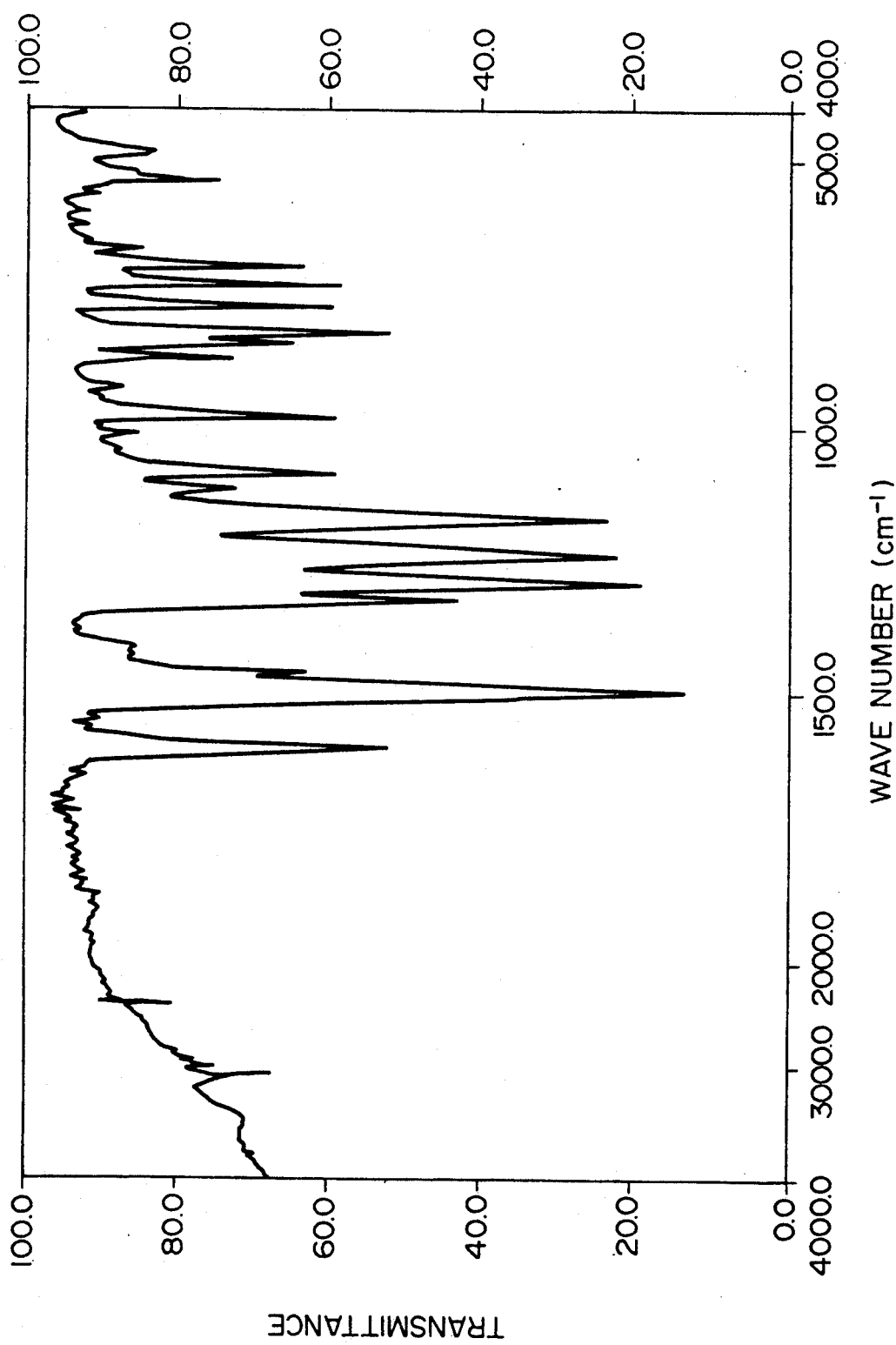

FIG. 16 shows infrared absorption spectrum of N,N'-bis(1,1'-biphenyl)-N,N'-bis[4-(2,2,2-trifluoroethoxyphenyl)]-[1,1'-biphenyl]-4,4'-diamine.

SYNTHESIS EXAMPLE 16

Synthesis of
N,N'-bis(3,4-dimethylphenyl)-N,N'-bis[3-(2,2,2-trifluoroethoxyphenyl)]-[1,1'-biphenyl]-4,4'-diamine
(Compound (I-46) and used in Example 18)

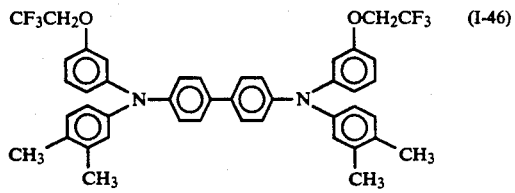

In a 300-ml round bottom glass flask equipped with a thermometer, a condenser attaching a water separator and a stirrer, 100 mmoles of 4,4'-diiodobiphenyl in purity of 99.0%, 260 mmoles of N-3-(2,2,2-trifluoroethoxyphenyl)-3,4-xylidine in purity of 99.3%, 20.7 g of potassium carbonate, and 8 g of a copper powder were placed and maintained at 210° to 220° C. for 9 hours. The water produced during the reaction was taken out of the reaction system by the water separator.

After the reaction, the contents were diluted with 350 ml of toluene and filtered to remove insoluble materials. The resulting toluene solution was concentrated under reduced pressure to give a brown oily material.

The brown oily material was subjected to treatment with active carbon in an ethyl acetate solvent and was purified by column chromatography (alumina/toluene), and finally recrystallized from n-hexane to give white crystals of N,N'-(3,4-dimethylphenyl)-N,N'-bis[3-(2,2,2-trifluoroethoxyphenyl)]-[1,1'-biphenyl]-4,4'-diamine in purity of 99.8% and having a melting point of 147.1° C. in an amount of 34.3 g (yield 46.3%).

Elementary analysis (for $C_{44}H_{38}F_6N_2O_2$).

|  | C (%) | H (%) | F (%) | N (%) |
| --- | --- | --- | --- | --- |
| Calcd. | 71.34 | 5.17 | 15.39 | 3.78 |
| Found | 71.59 | 5.14 | 16.30 | 3.71 |

Figure 17:
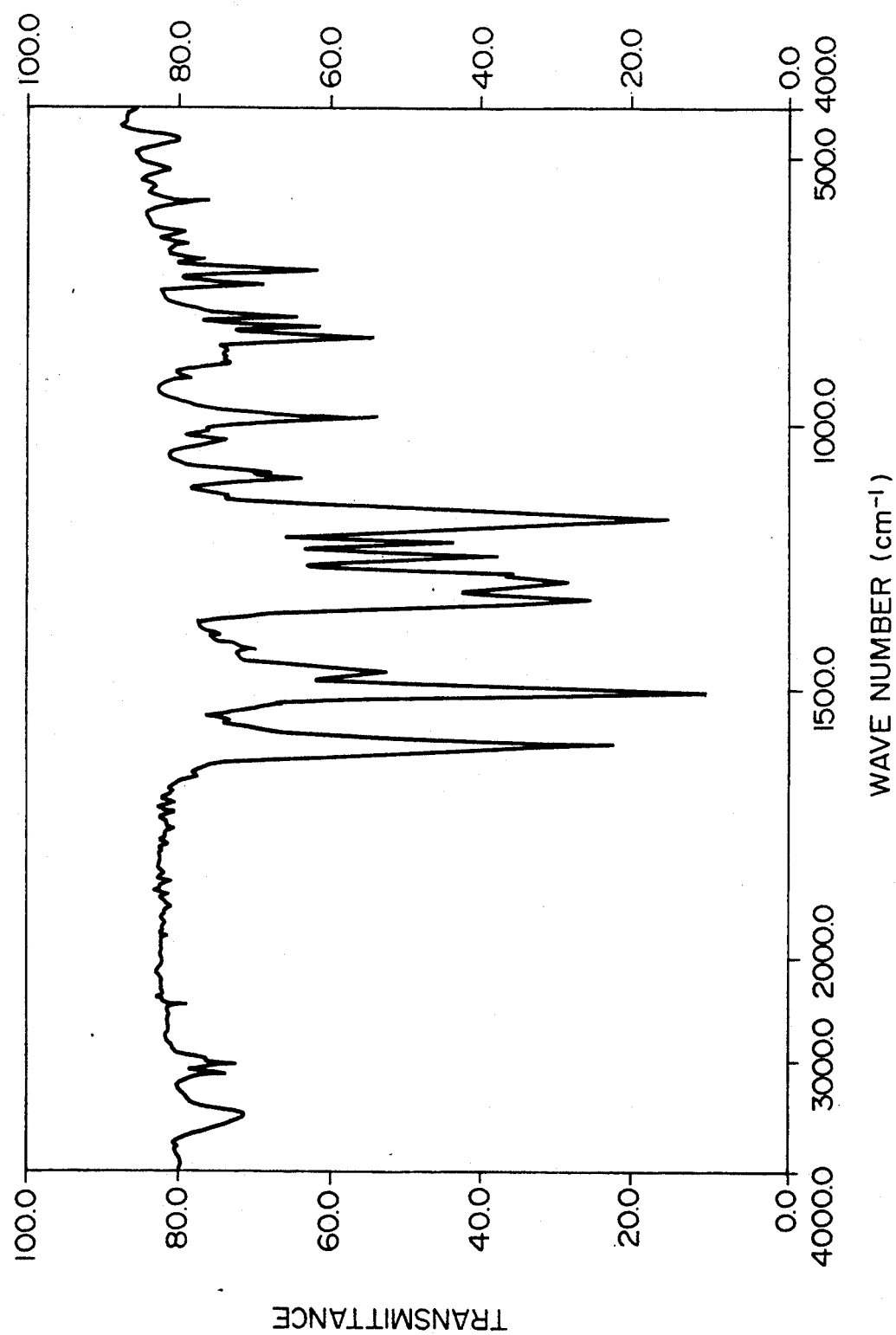

FIG. 17 shows infrared absorption spectrum of N,N'-(3,4-dimethylphenyl)-N,N'-bis[3-(2,2,2-trifluoroethoxyphenyl)]-[1,1'-biphenyl]-4,4'-diamine.

SYNTHESIS EXAMPLE 17

Synthesis of N-4-(2,2,2-trifluoroethoxy)phenylaniline
(Compound (XI-13))

In a 2,000-ml round bottom glass flask equipped with a thermometer, a condenser and a stirrer, 482.1 g of p-(2,2,2-trifluoroethoxy)aniline in purity of 99.1% and 900 ml of glacial acetic acid were placed and heated to 55° C. in the liquid temperature. Then, 260 ml of acetic anhydride was added dropwise for 1 hour, then the temperature was maintained at 70° C. for 1 hour.

After the reaction, the contents were poured into 5,500 ml of water, and filtered deposited crystalline material and dried under reduced pressure to give white crystals of p-(2,2,2-trifluoroethoxy)acetanilide in purity of 99.4% in an amount of 517.9 g (yield 88.3%), having a melting point of 139.2° C.

In the next place, in a 300-ml round bottom glass flask equipped with a thermometer, a condenser attaching a water separator and a stirrer, 82.1 g of p-(2,2,2-trifluoroethoxy)acetanilide, 78.8 g of iodobenzene in purity of 99.0%, 36.4 g of potassium carbonate and 6.6 g of a copper powder were placed and maintained at 200° C. for 9 hours. The water generated by the reaction was taken out of the reaction system by the water separator.

After the reaction, the contents were cooled and added with 50 ml of dimethylsulfoxide and 50 ml of 40% aqueous solution of potassium hydroxide, followed by gradual heating to 70° to 12.5° C. for 6 hours.

After the reaction, the contents were diluted with 150 ml of toluene and extracted, and filtered to remove insoluble materials. The resulting toluene layer was washed with a 10% aqueous solution of sodium sulfate and water in this order.

Finally, the toluene was removed by evaporation under reduced pressure to recover a fraction of about 165° C./3 Torr by vacuum distillation. As a result, white crystals of N-4-(2,2,2-trifluoroethoxy)phenylaniline in purity of 99.7% were obtained in an amount of 77.4 g (yield 82.6%). Melting point was 53.6° C.

Elementary analysis (for $C_{14}H_{12}F_3NO$).

|  | C (%) | H (%) | F (%) | N (%) |
| --- | --- | --- | --- | --- |
| Calcd. | 62.92 | 4.52 | 21.33 | 5.24 |
| Found | 63.60 | 4.51 | 19.52 | 5.15 |

Figure 18:
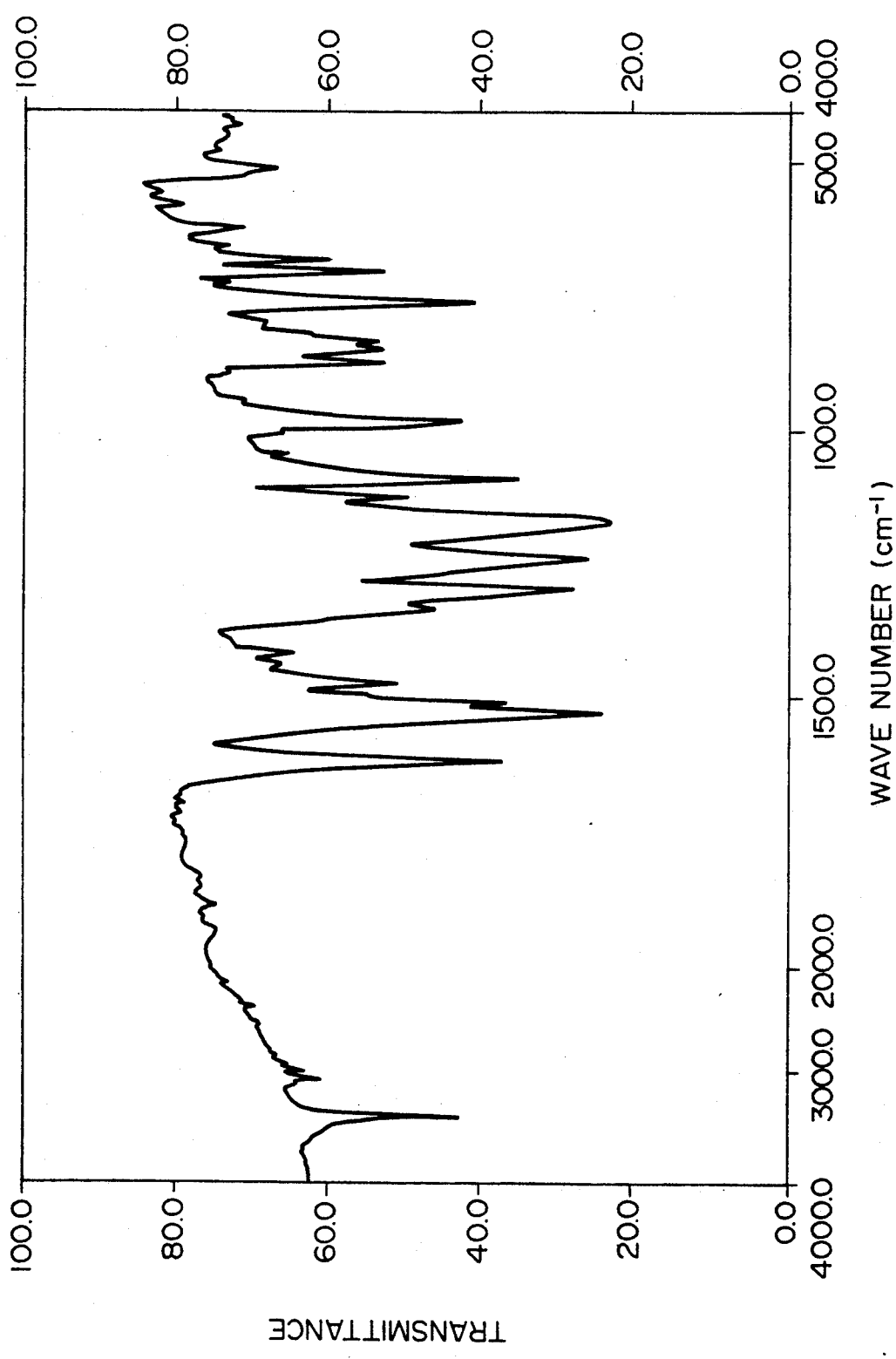

FIG. 18 shows an infrared absorption spectrum of N-4-(2,2,2-trifluoroethoxy)phenyl-aniline (KBr tablet method).

SYNTHESIS EXAMPLE 18

Synthesis of
N-4-(2,2,2-trifluoroethoxy)phenyl-m-toluidine
(Compound (XI-14))

Reaction was conducted in the same manner as Synthesis Example 17 except for using 84.3 g of m-iodobenzene in purity of 99.7% in place of iodobenzene used in Synthesis Example 17 and reacting for 6 hours.

After the reaction, the hydrolysis reaction, extraction with toluene, filtration and washing procedure were conducted in the same manner as described in Synthesis Example 17.

Finally, the toluene was removed by evaporation under reduced pressure to recover a fraction of about 175° C./3 Torr by vacuum distillation. As a result, white crystals of N-4-(2,2,2-trifluoroethoxy)phenyl-m-toluidine in purity of 99.4% were obtained in an amount of 79.4 g (yield 80.1%). Melting point was 44.4° C.

Elementary analysis (for $C_{15}H_{14}F_3NO$).

|  | C (%) | H (%) | F (%) | N (%) |
| --- | --- | --- | --- | --- |
| Calcd. | 64.05 | 5.02 | 20.26 | 4.98 |
| Found | 64.74 | 4.98 | 20.20 | 4.78 |

Figure 19:
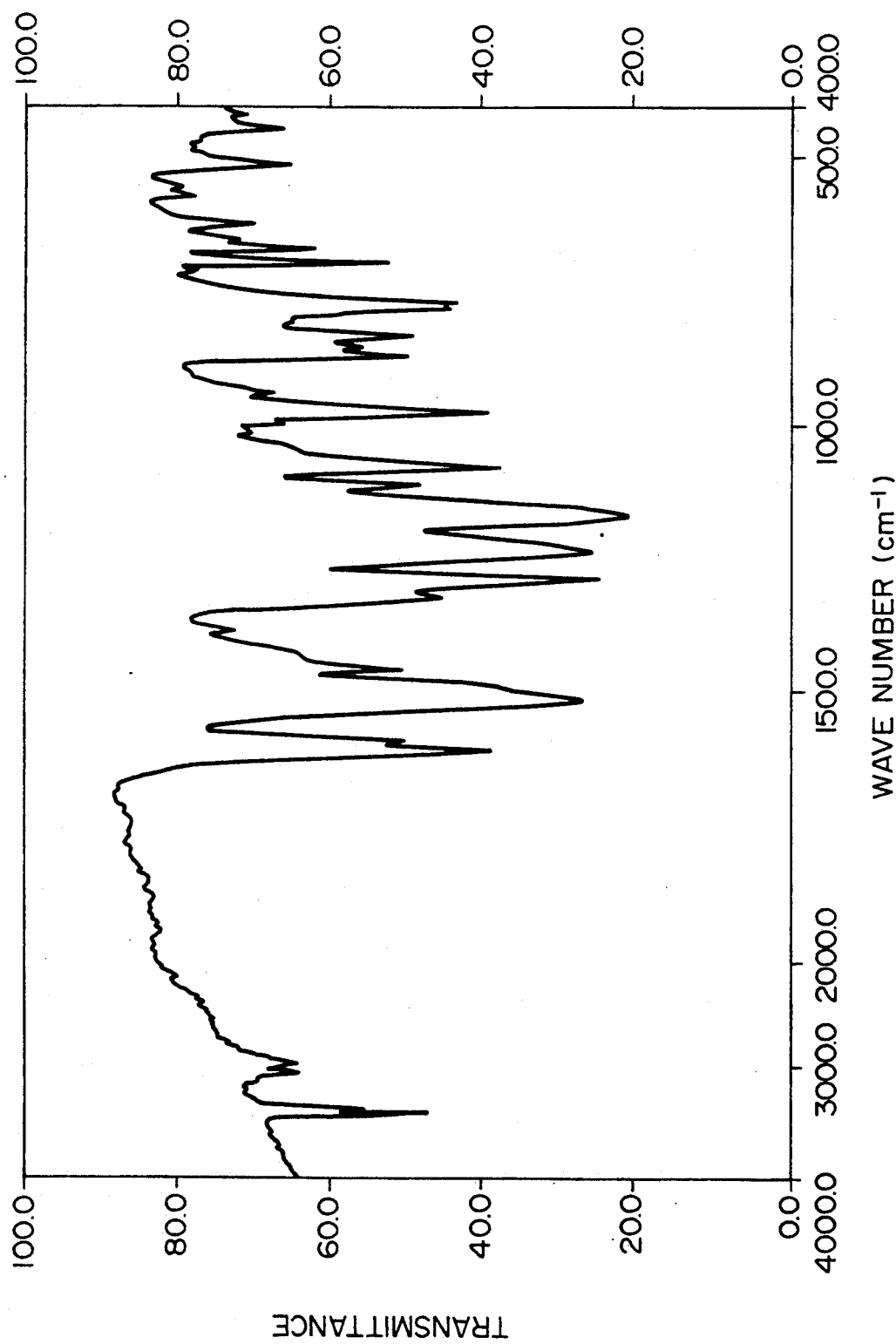

FIG. 19 shows an infrared absorption spectrum of N-4-(2,2,2-trifluoroethoxy)phenyl-m-toluidine (KBr tablet method).

SYNTHESIS EXAMPLE 19

Synthesis of
N-4-(2,2,2-trifluoroethoxy)phenyl-p-toluidine
(Compound (XI-15))

Reaction was conducted in the same manner as Synthesis Example 17 except for using 84.3 g of p-iodobenzene in purity of 99.8% in place of iodobenzene used in Synthesis Example 17 and reacting at 220° C. for 5 hours.

After the reaction, the hydrolysis reaction, extraction with toluene, filtration and washing procedure were conducted in the same manner as described in Synthesis Example 17.

Finally, the toluene was removed by evaporation under reduced pressure to recover a fraction of about 200° C./10 Torr by vacuum distillation. As a result, white crystals of N-4-(2,2,2-trifluoroethoxy)phenyl-p-toluidine in purity of 99.8% were obtained in an amount of 83.8 g (yield 85.0%). Melting point was 76.1° C.

Elementary analysis (for $C_{15}H_{14}F_3NO$).

|  | C (%) | H (%) | F (%) | N (%) |
|---|---|---|---|---|
| Calcd. | 64.05 | 5.02 | 20.26 | 4.98 |
| Found | 64.35 | 4.95 | 21.05 | 4.72 |

Figure 20:
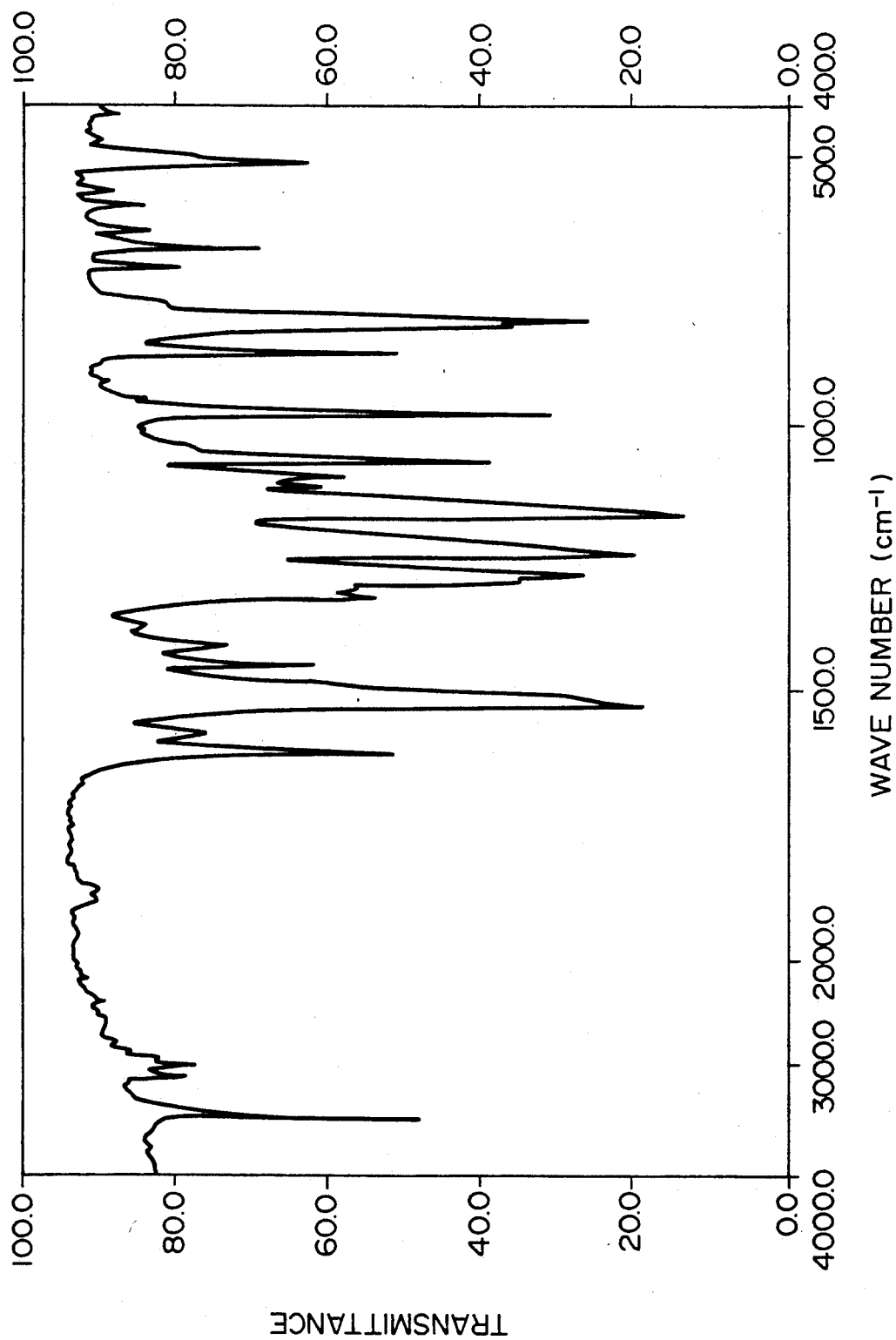

FIG. 20 shows an infrared absorption spectrum of N-4-(2,2,2-trifluoroethoxy)phenyl-m-toluidine (KBr tablet method).

SYNTHESIS EXAMPLE 20

Synthesis of N-4-(2,2,2-trifluoroethoxy)phenyl-p-anisidine (Compound (XI-20))

Reaction was conducted in the same manner as Synthesis Example 17 except for using 99.4 g of p-iodoanisole in purity of 99.5% in place of iodobenzene used in Synthesis Example 17 and reacting at 220° C. for 7 hours.

After the reaction, the hydrolysis reaction, extraction with toluene (toluene 200 ml), filtration and washing procedure were conducted in the same manner as described in Synthesis Example 17.

Finally, the toluene was removed by evaporation under reduced pressure to recover a fraction of about 180° C./10 Torr by vacuum distillation. As a result, white crystals of N-4-(2,2,2-trifluoroethoxy)phenyl-p-anisidine in purity of 99.6% were obtained in an amount of 77.0 g (yield 73.7%). Melting point was 62.8° C.

Elementary analysis (for $C_{15}H_{14}F_3NO_2$).

|  | C (%) | H (%) | F (%) | N (%) |
|---|---|---|---|---|
| Calcd. | 60.61 | 4.75 | 19.17 | 4.71 |
| Found | 60.93 | 4.72 | 20.38 | 4.63 |

Figure 21:
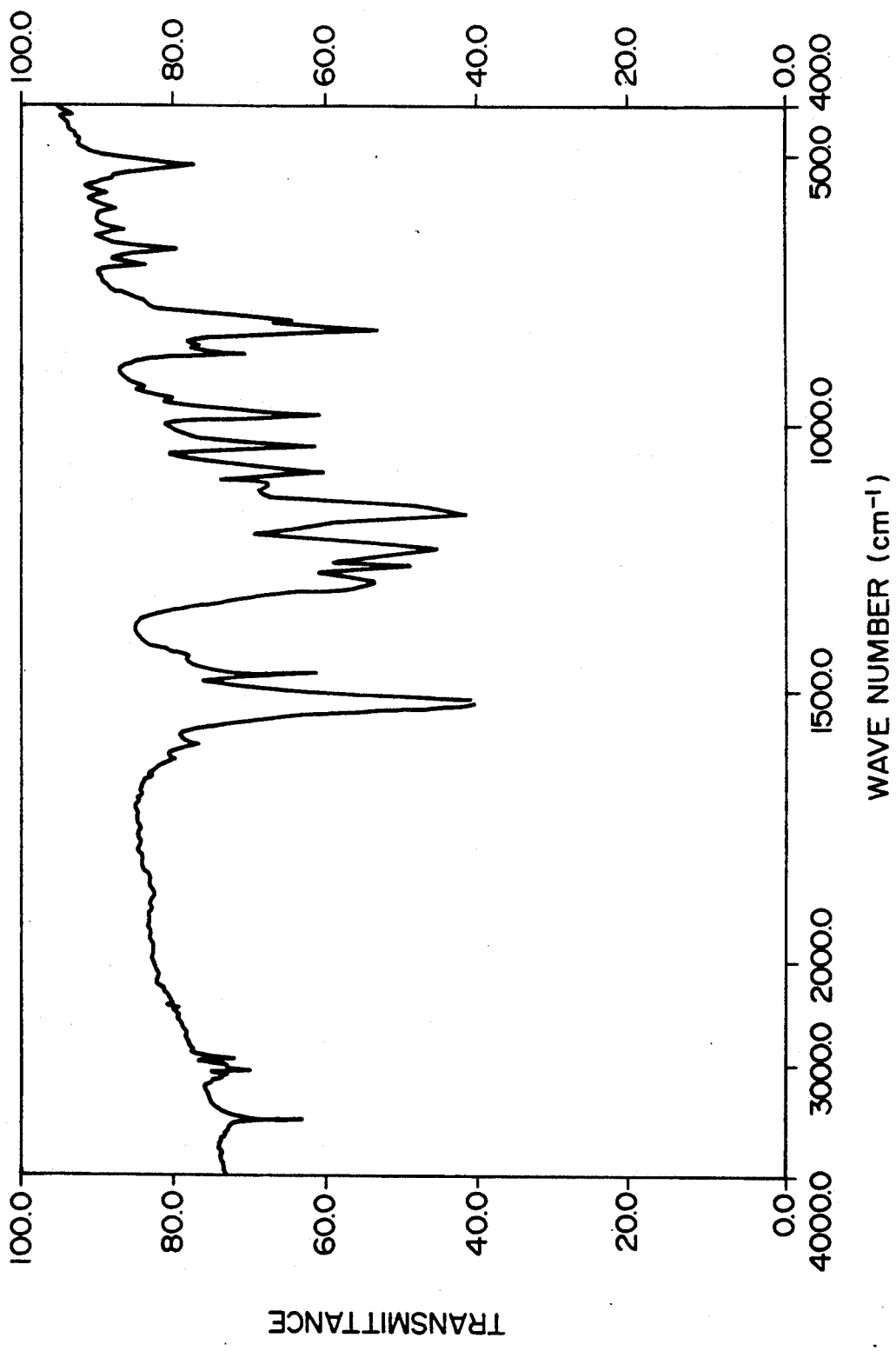

FIG. 21 shows an infrared absorption spectrum of N-4-(2,2,2-trifluoroethoxy)phenyl-p-anisidine (KBr tablet method).

SYNTHESIS EXAMPLE 21

Synthesis of N-4-(2,2,2-trifluoroethoxy)phenyl-4-phenylaniline (Compound (XI-23))

Reaction was conducted in the same manner as Synthesis Example 17 except for using 91.3 g of 4-iodobiphenyl in purity of 99.4% in place of iodobenzene used in Synthesis Example 17 and reacting at 210° C. for 10 hours.

After the reaction, the hydrolysis reaction, extraction with toluene (toluene 500 ml), filtration and washing procedure were conducted in the same manner as described in Synthesis Example 17.

Finally, the toluene solution was condensed to 250 ml by evaporation under reduced pressure and poured into 900 ml of n-hexane, and filtered deposited crystalline material and dried. As a result, white crystals of N-4-(2,2,2-trifluoroethoxy)phenyl-4-phenylaniline in purity of 99.6% were obtained in an amount of 83.0 g (yield 68.8%). Melting point was 117.0° C.

Elementary analysis (for $C_{20}H_{16}F_3NO$).

|  | C (%) | H (%) | F (%) | N (%) |
|---|---|---|---|---|
| Calcd. | 69.96 | 4.70 | 16.60 | 4.08 |
| Found | 70.32 | 4.68 | 17.37 | 4.13 |

Figure 22:
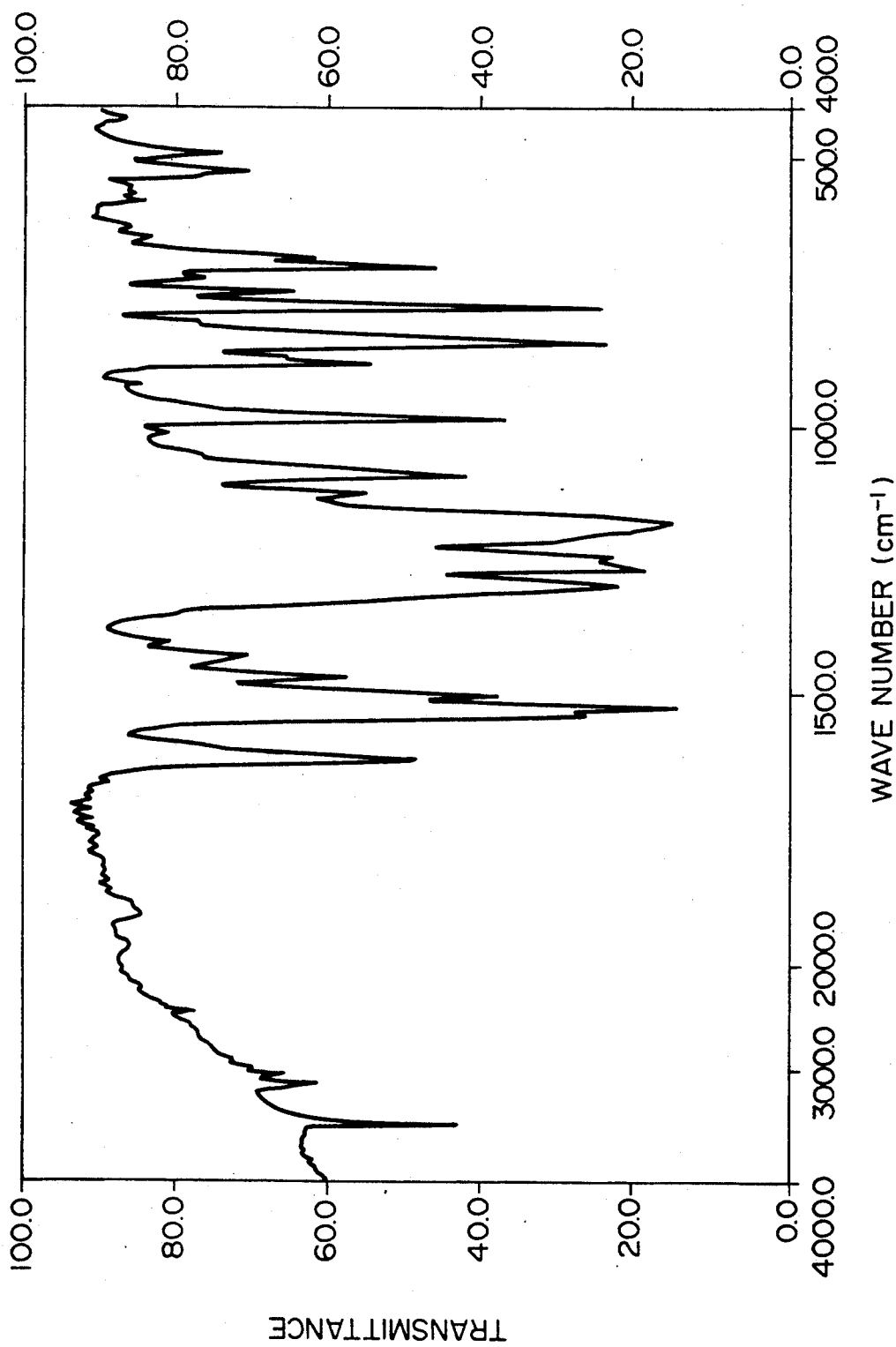

FIG. 22 shows an infrared absorption spectrum of N-4-(2,2,2-trifluoroethoxy)phenyl-4-phenylaniline (KBr tablet method).

As mentioned above, since the electrophotographic member of the present invention contains as a charge transport material a fluorine-containing N,N,N',N'-tetraarylbenzidine derivative remarkably excellent in solubility in an organic solvent and/or a binder such as polycarbonate resin, etc., there can be obtained very excellent electrophotographic properties such as high sensitivity, low residual potential, high durability, etc.

What is claimed is:

1. An electrophotographic member containing as a charge transport material a fluorine-containing N,N,N',N'-tetraarylbenzidine derivative represented by the formula:

$$\begin{array}{c}R_1\\ \diagdown\\ Ar^1\\ \diagdown\\ N-\phi-\phi-N\\ \diagup\\ Ar^2\\ \diagup\\ R_2\end{array}\begin{array}{c}Ar^1\\ \diagup\\ \\ \diagdown\\ Ar^2\\ \diagdown\\ R_2\end{array}\quad (I)$$

wherein $R_1$ and $R_2$ are independently a hydrogen atom, an alkyl group, an alkoxy group, a fluoroalkyl group or a fluoroalkoxy group, at least one of $R_1$ and $R_2$ is a fluoroalkyl group or a fluoroalkoxy group; and $Ar^1$ and $Ar^2$ are independently an aryl group which may have one or more substituents other than $R_1$ and $R_2$.

2. An electrophotographic member according to claim 1, wherein the fluorine-containing N,N,N',N'-tetraarylbenzidine derivative of the formula (I) is contained in a photoconductive layer formed on an electroconductive support together with a charge generation material.

3. An electrophotographic member according to claim 1, wherein the fluorine-containing N,N,N',N'-tetraarylbenzidine derivative of the formula (I) is contained in a charge transport layer, which is formed on a charge generation layer containing a charge generation material and formed on an electroconductive support, or between the charge generation layer and the electroconductive support.

4. An electrophotographic member according to claim 2, wherein an undercoating layer is present between the photoconductive layer and the electroconductive support.

5. An electrophotographic member according to claim 3, wherein an undercoating layer is present between the charge transport layer and the electroconductive support, or between the charge generation layer and the electroconductive support.

6. An electrophotographic member according to claim 1, which further comprises as a binder a polycarbonate resin having a molecular weight of 20,000 to 150,000 and represented by the formula:

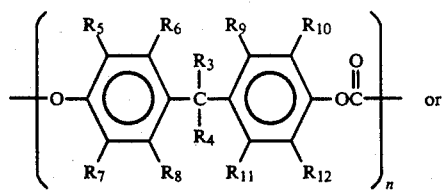
(II)

or

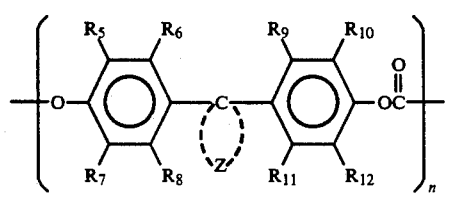
(III)

wherein $R_3$ and $R_4$ are independently a hydrogen atom, an alkyl group or an aryl group; $R_5$ through $R_{12}$ are independently a hydrogen atom, a halogen atom, an alkyl group or an aryl group; Z is a residue for forming a carbon ring which may have one or more substituents or a heterocyclic ring which may have one or more substituents; and n is an integer for meeting the molecular weight.

7. An electrophotographic member according to claim 1, which further comprises as a binder a polycarbonate copolymer having a molecular weight of 20,000 to 120,000 and represented by the formula:

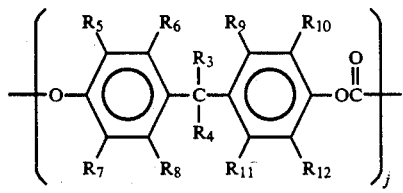
(IV)

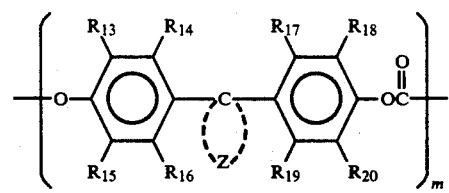

wherein $R_3$ and $R_4$ are independently a hydrogen atom, an alkyl group or an aryl group; $R_5$ through $R_{20}$ are independently a hydrogen atom, a halogen atom, an alkyl group or an aryl group; Z is a residue for forming a carbon ring which may have one or more substituents or a heterocyclic ring which may have one or more substituents; a copolymerization ratio $j/m = 1/10$ to $10/1$.

8. An electrophotographic member according to claim 1, which further comprises as a binder a polyester carbonate having a molecular weight of 20,000 to 120,000 and represented by the formula:

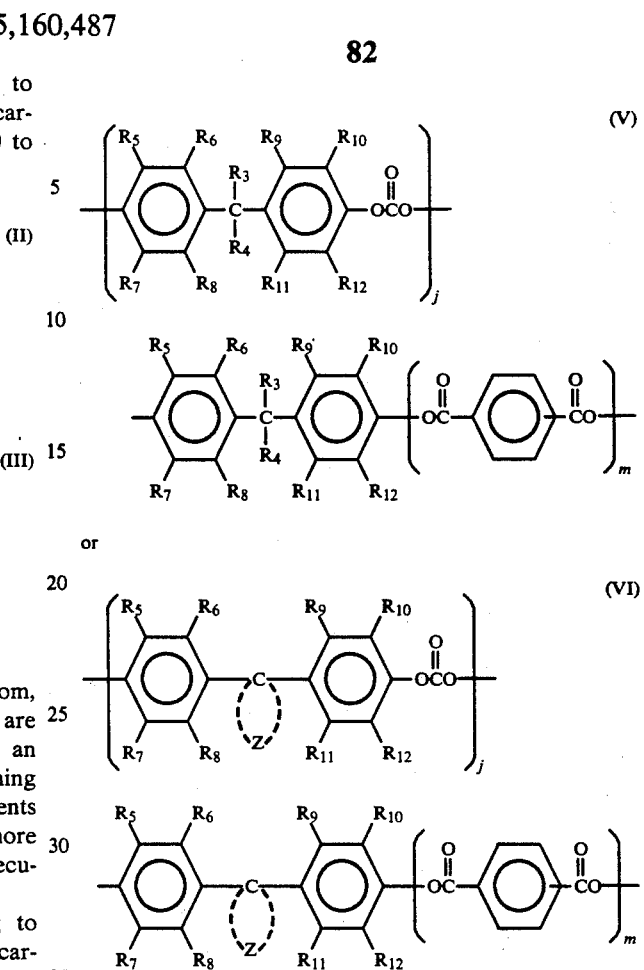
(V)

or (VI)

wherein $R_3$ and $R_4$ are independently a hydrogen atom, an alkyl group or an aryl group; $R_5$ through $R_{12}$ are independently a hydrogen atom, a halogen atom, an alkyl group or an aryl group; Z is a residue for forming a carbon ring which may have one or more substituents or a heterocyclic ring which may have one or more substituents; and a copolymerization ratio $j/m = 1/1$ to $10/1$.

9. An electrophotographic member according to claim 2, wherein the charge generation material is a phthalocyanine represented by the formula:

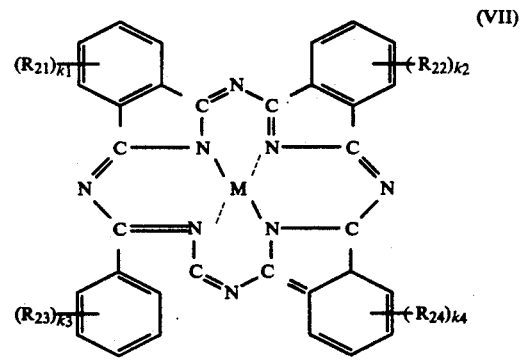
(VII)

wherein M is $H_2$ and/or TiO; $R_{21}$ through $R_{24}$ are independently a hydrogen atom, a halogen atom, an alkyl group or an alkoxy group; and $k_1$ through $k_4$ are independently an integer of 1 to 4.

10. An electrophotographic member according to claim 3, wherein the charge generation material is a photolocyanine represented by the formula:

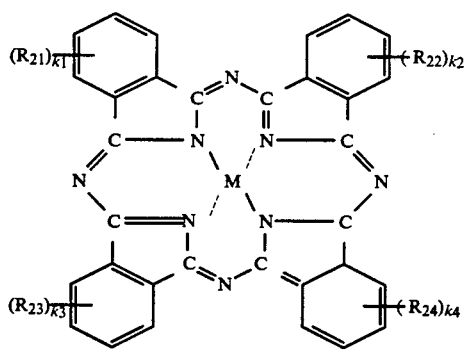

(VII)

wherein M is $H_2$ and/or TiO; $R_{21}$ through $R_{24}$ are independently a hydrogen atom, a halogen atom, an alkyl group or an alkoxy group; and $k_1$ and through $k_4$ are independently an integer of 1 to 4.

11. An electrophotographic member according to claim 10, which further comprises as a charge generation material a polyester resin.

12. An electrophotographic member according to claim 10, which further comprises as a charge generation material a polyvinyl acetal resin.

13. An electrophotographic member according to claim 3, wherein the charge generation material is β-form titanyl phtalocyanine which shows strong diffraction peaks at Bragg angles (2θ±0.2°) of 9.3°, 10.6°, 13.2°, 15.1°, 15.7°, 16.1°, 20.8°, 23.3°, 26.3° and 27.1° in X-ray diffraction pattern.

14. An electrophotographic member according to claim 13, which further comprises as a binder a polycarbonate resin having a molecular weight of 20,000 to 150,000 and represented by the formula (II) or (III).

* * * * *